(12) United States Patent
Connor

(10) Patent No.: US 9,891,718 B2
(45) Date of Patent: Feb. 13, 2018

(54) DEVICES FOR MEASURING FINGER MOTION AND RECOGNIZING HAND GESTURES

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 0 days.

(21) Appl. No.: 15/130,995

(22) Filed: Apr. 17, 2016

(65) Prior Publication Data

US 2016/0313798 A1 Oct. 27, 2016

Related U.S. Application Data

(60) Provisional application No. 62/150,886, filed on Apr. 22, 2015.

(51) Int. Cl.
| | | |
|---|---|---|
| G06F 3/01 | (2006.01) |
| A61B 5/00 | (2006.01) |
| A61B 5/11 | (2006.01) |
| A61B 5/0488 | (2006.01) |
| A61B 5/0476 | (2006.01) |
| G06F 3/03 | (2006.01) |

(52) U.S. Cl.
CPC ............ *G06F 3/017* (2013.01); *A61B 5/0059* (2013.01); *A61B 5/0476* (2013.01); *A61B 5/0488* (2013.01); *A61B 5/1125* (2013.01); *A61B 5/6826* (2013.01); *G06F 3/014* (2013.01); *G06F 3/0325* (2013.01); *A61B 2503/12* (2013.01); *A61B 2562/0266* (2013.01); *G06F 2203/0331* (2013.01)

(58) Field of Classification Search
CPC ..... G06F 3/017; A61B 5/0059; A61B 5/0476; A61B 5/1125
See application file for complete search history.

(56) References Cited

U.S. PATENT DOCUMENTS

| | | | |
|---|---|---|---|
| 3,972,038 A | 7/1976 | Fletcher et al. | |
| 4,414,537 A | 11/1983 | Grimes | |
| 5,316,017 A | 5/1994 | Edwards et al. | |
| 5,581,484 A | 12/1996 | Prince | |
| 5,610,528 A | 3/1997 | Neely et al. | |
| 5,964,701 A | 10/1999 | Asada et al. | |
| 5,980,472 A | 11/1999 | Seyl | |
| 6,049,327 A | 4/2000 | Walker et al. | |
| 6,094,747 A * | 8/2000 | Malick ................ | A41D 13/087 2/159 |
| 6,104,379 A | 8/2000 | Petrich et al. | |
| 6,110,130 A | 8/2000 | Kramer | |
| 6,128,004 A | 10/2000 | McDowall et al. | |
| 6,141,643 A | 10/2000 | Harmon | |

(Continued)

*Primary Examiner* — Sejoon Ahn

(57) ABSTRACT

This invention can be embodied in a wearable device or system for measuring finger motion and recognizing hand gestures comprising a distal loop which encircles the intermediate phalanx of a finger, a proximal loop which encircles the proximal phalanx of the finger, a joint-spanning strip which connects these two loops, and a bend sensor which is part of the joint-spanning strip. Changes in energy transmitted through, or generated by, the bend sensor are used to measure the motion and/or configuration of the proximal interphalangeal joint.

14 Claims, 27 Drawing Sheets

(56) References Cited

U.S. PATENT DOCUMENTS

| | | | |
|---|---|---|---|
| 6,162,190 A | 12/2000 | Kramer | |
| 6,239,784 B1 | 5/2001 | Holmes | |
| 6,304,840 B1 | 10/2001 | Vance et al. | |
| 6,325,768 B1 | 12/2001 | Williams et al. | |
| 6,334,852 B1 | 1/2002 | Seyl | |
| 6,380,923 B1 | 4/2002 | Fukumoto et al. | |
| 6,402,690 B1 | 6/2002 | Rhee et al. | |
| 6,452,584 B1 | 9/2002 | Walker et al. | |
| 6,526,669 B2 | 3/2003 | Nagata | |
| 6,622,575 B1 | 9/2003 | Nagata | |
| 6,651,352 B2 | 11/2003 | McGorry et al. | |
| 6,870,526 B2 | 3/2005 | Zngf et al. | |
| 6,940,062 B2 | 9/2005 | Kwon et al. | |
| 7,498,956 B2 | 3/2009 | Baier et al. | |
| 7,565,295 B1 | 7/2009 | Hernandez-Rebollar | |
| 7,662,113 B2 | 2/2010 | Pearl et al. | |
| 7,917,235 B2 | 3/2011 | Miller | |
| 8,140,339 B2 | 3/2012 | Fernandez-Rebollar | |
| 8,170,656 B2 | 5/2012 | Tan et al. | |
| 8,292,833 B2 | 10/2012 | Son et al. | |
| 8,373,656 B2 | 2/2013 | Hou et al. | |
| 8,386,060 B2 | 2/2013 | Miller | |
| 8,395,109 B2 | 3/2013 | Muraysky | |
| 8,421,448 B1 | 4/2013 | Tran et al. | |
| 8,447,704 B2 | 5/2013 | Tan et al. | |
| 8,466,811 B2 | 6/2013 | Kang et al. | |
| 8,493,174 B2 | 7/2013 | Agrawal | |
| 8,502,769 B2 | 8/2013 | Kim | |
| 8,581,856 B2 | 11/2013 | Benko et al. | |
| 8,681,101 B1 | 3/2014 | Haney et al. | |
| 8,686,947 B2 | 4/2014 | Wine | |
| 8,708,825 B2 | 4/2014 | Crisco | |
| 8,743,052 B1 | 6/2014 | Keller et al. | |
| 8,755,912 B2 | 6/2014 | Miller | |
| 8,892,479 B2 | 11/2014 | Tan et al. | |
| 8,917,202 B2 | 12/2014 | Grosinger et al. | |
| 9,008,973 B2 | 4/2015 | French | |
| 9,037,530 B2 | 5/2015 | Tan et al. | |
| 9,104,271 B1 | 8/2015 | Adams et al. | |
| 9,218,058 B2 | 12/2015 | Bress et al. | |
| 9,261,983 B2 | 2/2016 | Bailen | |
| 9,278,453 B2 | 3/2016 | Assad | |
| 9,299,248 B2 | 3/2016 | Lake et al. | |
| 2001/0001883 A1* | 5/2001 | Wanzenried | A41D 13/087 2/21 |
| 2001/0025917 A1* | 10/2001 | Asada | G01L 1/248 250/221 |
| 2001/0034947 A1 | 11/2001 | Nagata | |
| 2001/0045216 A1* | 11/2001 | Gardiner | A45D 29/00 132/73 |
| 2002/0024656 A1 | 2/2002 | Kwon et al. | |
| 2003/0009087 A1* | 1/2003 | Keirsbilck | A61B 5/01 600/300 |
| 2003/0011567 A1* | 1/2003 | Villet | G06F 3/014 345/157 |
| 2003/0071046 A1* | 4/2003 | Ribeiro | G06F 1/181 220/787 |
| 2003/0142065 A1 | 7/2003 | Pahlavan | |
| 2003/0214481 A1* | 11/2003 | Xiong | G06F 3/017 345/157 |
| 2004/0020815 A1* | 2/2004 | Panella | A41D 13/081 206/440 |
| 2004/0032346 A1 | 2/2004 | Kim et al. | |
| 2004/0169636 A1* | 9/2004 | Park | G06F 3/011 345/156 |
| 2004/0210166 A1 | 10/2004 | Soh et al. | |
| 2005/0035942 A1* | 2/2005 | Ruiz | G06F 3/03543 345/156 |
| 2005/0178213 A1 | 8/2005 | Skowronski | |
| 2006/0129068 A1* | 6/2006 | Makosinski | A61B 5/00 600/587 |
| 2006/0129070 A1* | 6/2006 | Pearl | A61B 5/0057 600/595 |
| 2006/0214912 A1 | 9/2006 | Miller | |
| 2006/0278468 A1* | 12/2006 | Bruck | A61F 11/08 181/135 |
| 2007/0132722 A1 | 6/2007 | Kim et al. | |
| 2007/0244377 A1* | 10/2007 | Cozad | A61B 5/14552 600/323 |
| 2008/0058622 A1* | 3/2008 | Baker | A61B 5/14552 600/344 |
| 2008/0136775 A1* | 6/2008 | Conant | G06F 3/014 345/156 |
| 2009/0095094 A1 | 4/2009 | Helmer et al. | |
| 2009/0153499 A1* | 6/2009 | Kim | G06F 3/011 345/173 |
| 2009/0212979 A1 | 8/2009 | Catchings et al. | |
| 2009/0278798 A1 | 11/2009 | Kim et al. | |
| 2009/0326406 A1 | 12/2009 | Tan et al. | |
| 2010/0023314 A1 | 1/2010 | Hernandez-Rebollar | |
| 2010/0063794 A1 | 3/2010 | Hernandez-Rebollar | |
| 2010/0083974 A1* | 4/2010 | Milican | A45D 29/007 132/73 |
| 2010/0090949 A1 | 4/2010 | Tianqiao et al. | |
| 2010/0127967 A1* | 5/2010 | Graumann | H02N 2/183 345/156 |
| 2010/0168531 A1* | 7/2010 | Shaltis | A61B 5/02241 600/301 |
| 2010/0207881 A1 | 8/2010 | Miller | |
| 2010/0302137 A1 | 12/2010 | Benko et al. | |
| 2011/0007035 A1* | 1/2011 | Shai | G06F 3/014 345/179 |
| 2011/0054360 A1 | 3/2011 | Son et al. | |
| 2011/0112771 A1 | 5/2011 | French | |
| 2011/0234384 A1 | 9/2011 | Agrawal | |
| 2011/0234483 A1 | 9/2011 | Lan et al. | |
| 2011/0257928 A1* | 10/2011 | Cunningham | A61B 5/1116 702/150 |
| 2011/0260963 A1 | 10/2011 | Timmons | |
| 2012/0029399 A1* | 2/2012 | Sankai | A61B 5/04888 601/40 |
| 2012/0139708 A1* | 6/2012 | Paradiso | G06F 3/014 340/10.1 |
| 2012/0188158 A1 | 7/2012 | Tan et al. | |
| 2012/0218184 A1 | 8/2012 | Wissmar | |
| 2012/0319940 A1 | 12/2012 | Bress et al. | |
| 2013/0135240 A1 | 5/2013 | Miller | |
| 2013/0147722 A1 | 6/2013 | Lin et al. | |
| 2013/0232095 A1 | 9/2013 | Tan et al. | |
| 2013/0317648 A1 | 11/2013 | Assad | |
| 2014/0031698 A1 | 1/2014 | Moon et al. | |
| 2014/0055338 A1 | 2/2014 | Ryan | |
| 2014/0098018 A1 | 4/2014 | Kim et al. | |
| 2014/0176439 A1 | 6/2014 | Keller et al. | |
| 2014/0238153 A1 | 8/2014 | Wood et al. | |
| 2014/0240103 A1 | 8/2014 | Lake et al. | |
| 2014/0240214 A1 | 8/2014 | Liu et al. | |
| 2014/0257143 A1 | 9/2014 | Friedman et al. | |
| 2014/0267024 A1 | 9/2014 | Keller et al. | |
| 2015/0065090 A1 | 3/2015 | Yeh | |
| 2015/0169074 A1 | 6/2015 | Ataee et al. | |
| 2015/0185971 A1 | 7/2015 | Gomez et al. | |
| 2015/0233779 A1 | 8/2015 | Chen et al. | |
| 2015/0241976 A1 | 8/2015 | Zhao et al. | |
| 2015/0309563 A1 | 10/2015 | Connor | |
| 2015/0338916 A1 | 11/2015 | Priyantha et al. | |
| 2015/0366504 A1 | 12/2015 | Connor | |
| 2015/0370320 A1 | 12/2015 | Connor | |
| 2016/0091965 A1* | 3/2016 | Wang | G06F 3/011 345/156 |

\* cited by examiner

DEVICES FOR MEASURING FINGER MOTION AND RECOGNIZING HAND GESTURES

CROSS-REFERENCE TO RELATED APPLICATIONS

This patent application claims the priority benefit of U.S. Provisional Patent Application No. 62/150,886 entitled "Nerd of the Rings: Devices for Measuring Finger Motion and Recognizing Hand Gestures" by Robert A. Connor filed on Apr. 22, 2015. The entire contents of this related application is incorporated herein by reference.

FEDERALLY SPONSORED RESEARCH

Not Applicable

SEQUENCE LISTING OR PROGRAM

Not Applicable

BACKGROUND

Field of Invention

This invention relates to devices for measuring finger motion and recognizing hand gestures.

INTRODUCTION

There has been considerable progress in the development of novel devices for measuring finger motion and recognizing hand gestures during the past two decades. Such devices can serve as a Human-to-Computer Interface (HCI) and can be especially useful for: communication from a human to a small-scale computing device wherein touch-based communication is challenging; human-to-computer communication in a noisy environment wherein voice-based communication is difficult; human-to-computer communication in a public environment wherein voice-based communication is neither private nor considerate; and human-to-computer communication involving complex manipulation of objects in three-dimensional space.

Despite this progress, there are limitations to devices in the prior art. It is challenging to create a device that measures the full range of hand motion without being obtrusive. The hand is a very prominent and flexibly-used part of the human body. Gloves, exoskeletons, and finger-tip covers in the prior art tend to be obtrusive and can interfere with flexible hand use. Motion-sensing rings are useful, but hard to locate near the ends of fingers for full-finger motion capture. Camera-based motion capture is also useful, but not very mobile. There remains a need for a wearable device or system that measures the full range of finger and hand motion without being too obtrusive. That is the goal of this invention.

Review of the Prior Art

It can be challenging trying to classify relevant art into discrete categories. However, classification of relevant art into categories, even if imperfect, can be an invaluable tool for reviewing a large body of relevant art. Towards this end, I have identified 23 categories of relevant art and provide examples of relevant art in each category (including patent or patent application number, inventor, publication date, and title). Some examples of relevant art disclose multiple concepts and thus appear in more than one category.

The 23 categories of relevant art herein are as follows: inertial sensor ring embodiment; inertial sensor fingertip/thimble embodiment; inertial sensor glove embodiment; inertial sensor wrist/armband embodiment; electromagnetic bend sensor glove embodiment; electromagnetic bend sensor exoskeleton embodiment; electromagnetic bend sensor clothing embodiment; electromagnetic bend sensor artificial skin embodiment; electromagnetic bend sensor general/other; optical bend sensor glove embodiment; optical bend sensor adhesion embodiment; optical bend sensor general/other; pressure sensor exoskeleton embodiment; pressure sensor glove embodiment; pressure sensor fingertip/thimble embodiment; touchpad glove embodiment; touchpad finger sleeve embodiment; touchpad clothing embodiment; EMG sensor wrist/armband embodiment; EMG sensor clothing embodiment; other electromagnetic sensor embodiment; RFID embodiment; and other relevant art.

Art in the first category comprises at least one inertial sensor in a ring embodiment. Prior art which appears to be in this category includes the following U.S. patents: U.S. Pat. No. 3,972,038 (Fletcher et al., Jul. 27, 1976, "Accelerometer Telemetry System"); U.S. Pat. No. 6,162,190 (Kramer, Dec. 19, 2000, "Determination of Kinematically Constrained Multi-Articulated Structures"); U.S. Pat. No. 7,662,113 (Pearl et al., Feb. 16, 2010, "Fingertip Tracker"); U.S. Pat. No. 8,502,769 (Kim, Aug. 6, 2013, "Universal Input Device"); U.S. Pat. No. 8,743,052 (Keller et al., Jun. 3, 2014, "Computing Interface System"); U.S. Pat. No. 9,008,973 (French, Apr. 15, 2015, "Wearable Sensor System with Gesture Recognition for Measuring Physical Performance"); and U.S. Pat. No. 9,218,058 (Bress et al., Dec. 22, 2015, "Wearable Digital Input Device for Multipoint Free Space Data Collection and Analysis"). Prior art which appears to be in this category also includes the following U.S. patent applications: 20030142065 (Pahlavan, Jul. 31, 2003, "Ring Pointer Device with Inertial Sensors"); 20040032346 (Kim et al., Feb. 19, 2004, "Information Input Device, Information Processing Device and Information Input Method"); 20060129070 (Pearl et al., Jun. 15, 2006, "Fingertip Tracker"); 20110112771 (French, May 12, 2011, "Wearable Sensor System with Gesture Recognition for Measuring Physical Performance"); 20120218184 (Wissmar, Aug. 30, 2012, "Electronic Finger Ring and the Fabrication Thereof"); 20120319940 (Bress et al., Dec. 20, 2012, "Wearable Digital Input Device for Multipoint Free Space Data Collection and Analysis"); and 20130147722 (Lin et al., Jun. 13, 2013, "Distant Multipoint Remote Control Device and System"). Prior art which appears to be in this category also includes the following U.S. patent applications: 20140098018 (Kim et al., Apr. 10, 2014, "Wearable Sensor for Tracking Articulated Body-Parts"); 20140176439 (Keller et al., Jun. 26, 2014, "Computing Interface System"); 20140257143 (Friedman et al., Sep. 11, 2014, "Systems and Methods for Monitoring Hand and Wrist Movement"); 20140267024 (Keller et al., Sep. 18, 2014, "Computing Interface System"); 20150065090 (Yeh, Mar. 5, 2015, "Wearable Ring-Shaped Electronic Device and the Controlling Method Thereof"); 20150241976 (Zhao et al., Aug. 27, 2015, "Wearable Finger Ring Input Device and Controller"); and 20150338916 (Priyantha et al., Nov. 25, 2015, "Finger Tracking").

Art in this next category comprises at least one inertial sensor in a fingertip or thimble embodiment. Prior art which appears to be in this category includes the following U.S. patents: U.S. Pat. No. 8,466,811 (Kang et al., Jun. 18, 2013, "Thimble-Type Intermediation Device and Method for Recognizing Finger Gesture Using the Same"); and U.S. Pat. No. 8,493,174 (Agrawal, Jul. 23, 2013, "Apparatus for Instantaneous Translation of Sign Language"). Prior art which appears to be in this category also includes the following U.S. patent applications: 20060129070 (Pearl et al., Jun. 15, 2006, "Fingertip Tracker"); 20090278798 (Kim et al., Nov. 12, 2009, "Active Fingertip-Mounted Object Digitizer"); and 20110234384 (Agrawal, Sep. 29, 2011, "Apparatus for Instantaneous Translation of Sign Language").

Art in this next category comprises at least one inertial sensor in a glove embodiment. Prior art which appears to be in this category includes the following U.S. patents: U.S. Pat. No. 5,581,484 (Prince, Dec. 3, 1996, "Finger Mounted Computer Input Device"); U.S. Pat. No. 6,162,190 (Kramer, Dec. 19, 2000, "Determination of Kinematically Constrained Multi-Articulated Structures"); U.S. Pat. No. 6,870,526 (Zngf et al., Mar. 22, 2005, "Glove Mouse with Virtual Tracking Ball"); U.S. Pat. No. 7,565,295 (Hernandez-Rebollar, Jul. 21, 2009, "Method and Apparatus for Translating Hand Gestures"); U.S. Pat. No. 8,140,339 (Hernandez-Rebollar, Mar. 20, 2012, "Method and Apparatus for Translating Hand Gestures"); and U.S. Pat. No. 9,218,058 (Bress et al., Dec. 22, 2015, "Wearable Digital Input Device for Multipoint Free Space Data Collection and Analysis"). Prior art which appears to be in this category also includes the following U.S. patent applications: 20090212979 (Catchings et al., Aug. 27, 2009, "Glove-Based Input Device"); 20100023314 (Hernandez-Rebollar, Jan. 28, 2010, "ASL Glove with 3-Axis Accelerometers"); 20100063794 (Hernandez-Rebollar, Mar. 11, 2010, "Method and Apparatus for Translating Hand Gestures"); 20100090949 (Tianqiao et al., Apr. 15, 2010, "Method and Apparatus for Input Device"); 20120319940 (Bress et al., Dec. 20, 2012, "Wearable Digital Input Device for Multipoint Free Space Data Collection and Analysis"); and 20150233779 (Chen et al., Aug. 20, 2015, "Gloves with Pressure Sensors").

Art in this next category comprises at least one inertial sensor in a wrist or armband embodiment. Prior art which appears to be in this category includes the following U.S. patents: U.S. Pat. No. 8,292,833 (Son et al., Oct. 23, 2012, "Finger Motion Detecting Apparatus and Method"); U.S. Pat. No. 8,743,052 (Keller et al., Jun. 3, 2014, "Computing Interface System"); U.S. Pat. No. 9,278,453 (Assad, Mar. 8, 2016, "Biosleeve Human-Machine Interface"); and U.S. Pat. No. 9,299,248 (Lake et al., Mar. 29, 2016, "Method and Apparatus for Analyzing Capacitive EMG and IMU Sensor Signals for Gesture Control"). Prior art which appears to be in this category also includes the following U.S. patent applications: 20110054360 (Son et al., Mar. 3, 2011, "Finger Motion Detecting Apparatus and Method"); 20130317648 (Assad, Nov. 28, 2013, "Biosleeve Human-Machine Interface"); 20140176439 (Keller et al., Jun. 26, 2014, "Computing Interface System"); 20140240103 (Lake et al., Aug. 28, 2014, "Methods and Devices for Combining Muscle Activity Sensor Signals and Inertial Sensor Signals for Gesture-Based Control"); 20140267024 (Keller et al., Sep. 18, 2014, "Computing Interface System"); and 20150366504 (Connor, Dec. 24, 2015, "Electromyographic Clothing").

Art in this next category comprises at least one electromagnetic bend sensor in a glove embodiment. Prior art which appears to be in this category includes the following U.S. patents: U.S. Pat. No. 5,316,017 (Edwards et al., May 31, 1994, "Man-Machine Interface for a Joint Measurement System"); U.S. Pat. No. 6,049,327 (Walker et al., Apr. 11, 2000, "System for Data Management Based Onhand Gestures"); U.S. Pat. No. 6,162,190 (Kramer, Dec. 19, 2000, "Determination of Kinematically Constrained Multi-Articulated Structures"); U.S. Pat. No. 6,325,768 (Williams et al., Dec. 4, 2001, "Glove for Making Goniometric Measures"); U.S. Pat. No. 6,452,584 (Walker et al., Sep. 17, 2002, "System for Data Management Based on Hand Gestures"); and U.S. Pat. No. 8,421,448 (Tran et al., Apr. 16, 2013, "Hall-Effect Sensor System for Gesture Recognition, Information Coding, and Processing"). Prior art which appears to be in this category also includes the following U.S. patent applications: 20050178213 (Skowronski, Aug. 18, 2005, "Device for Determining Finger Rotation Using a Displacement Sensor"); 20070132722 (Kim et al., Jun. 14, 2007, "Hand Interface Glove Using Miniaturized Absolute Position Sensors and Hand Interface System Using the Same"); 20110234483 (Lan et al., Sep. 29, 2011, "Game Controller Glove"); 20140055338 (Ryan, Feb. 27, 2014, "Glove-Based User Interface Device"); and 20160054798 (Messingher et al., Feb. 25, 2016, "Glove Interface Object").

Art in this next category comprises at least one electromagnetic bend sensor in an exoskeleton embodiment. Prior art which appears to be in this category includes the following U.S. patents: U.S. Pat. No. 6,104,379 (Petrich et al., Aug. 15, 2000, "Forearm-Supported Exoskeleton Hand-Tracking Device"); U.S. Pat. No. 6,110,130 (Kramer, Aug. 29, 2000, "Exoskeleton Device for Directly Measuring Fingertip Position and Inferring Finger Joint Angle"); U.S. Pat. No. 6,239,784 (Holmes, May 29, 2001, "Exo-Skeletal Haptic Computer Human/Computer Interface Device"); U.S. Pat. No. 6,526,669 (Nagata, Mar. 4, 2003, "Apparatus for Acquiring Human Finger Manipulation Data"); U.S. Pat. No. 6,651,352 (McGorry et al., Nov. 25, 2003, "Wrist Motion Measurement Device"); U.S. Pat. No. 8,708,825 (Crisco, Apr. 29, 2014, "Device Controller with Conformable Fitting System"). Prior art which appears to be in this category also includes U.S. patent application 20010034947 (Nagata, Nov. 1, 2001, "Apparatus for Acquiring Human Finger Manipulation Data").

Art in this next category comprises at least one electromagnetic bend sensor in a clothing embodiment. Prior art which appears to be in this category includes the following U.S. patent applications: 20090095094 (Helmer et al., Apr. 16, 2009, "System and Garment for Detecting Movement"); and 20150309563 (Connor, Oct. 29, 2015, "Motion Recognition Clothing™ with Flexible Electromagnetic, Light, or Sonic Energy Pathways").

Art in this next category comprises at least one electromagnetic bend sensor in an artificial skin embodiment. Prior art which appears to be in this category includes U.S. patent application 20140238153 (Wood et al., Aug. 28, 2014, "Artificial Skin and Elastic Strain Sensor").

Art in this next category comprises at least one electromagnetic bend sensor in a general manner. Prior art which appears to be in this category includes the following U.S. patents: U.S. Pat. No. 5,610,528 (Neely et al., Mar. 11, 1997, "Capacitive Bend Sensor"); and U.S. Pat. No. 8,917,202 (Grosinger et al., Dec. 23, 2014, "Backscatter RFID Sensor with a Bend Transducer").

Art in this next category comprises at least one optical bend sensor in a glove embodiment. Prior art which appears to be in this category includes the following U.S. patents: U.S. Pat. No. 6,304,840 (Vance et al., Oct. 16, 2001, "Fingerless Glove for Interacting with Data Processing System"); and U.S. Pat. No. 8,395,109 (Muraysky, Mar. 12, 2013, "Motion Sensor for Detecting Bending or Pivoting").

Art in this next category comprises at least one optical bend sensor in an adhesive embodiment. Prior art which appears to be in this category includes U.S. patent application 20140031698 (Moon et al., Jan. 30, 2014, "Apparatus and Method for Sensing Bone Position and Motion").

Art in this next category comprises at least one optical bend sensor in a general manner. Prior art which appears to be in this category includes U.S. Pat. No. 6,940,062 (Kwon et al., Sep. 6, 2005, "Optical Fiber Curvature Sensor for Measuring Body Motion and Its Adhesive Method"). Prior art which appears to be in this category also includes U.S. patent application 20020024656 (Kwon et al., Feb. 28, 2002, "Optical Fiber Curvature Sensor for Measuring Body Motion and Its Adhesive Method").

Art in this next category comprises at least one pressure sensor in an exoskeleton embodiment. Prior art which appears to be in this category includes U.S. Pat. No. 6,526,669 (Nagata, Mar. 4, 2003, "Apparatus for Acquiring Human Finger Manipulation Data"). Prior art which appears to be in this category also includes U.S. patent application 20010034947 (Nagata, Nov. 1, 2001, "Apparatus for Acquiring Human Finger Manipulation Data").

Art in this next category comprises at least one pressure sensor in a glove embodiment. Prior art which appears to be in this category includes the following U.S. patents: U.S. Pat. No. 5,581,484 (Prince, Dec. 3, 1996, "Finger Mounted Computer Input Device"); and U.S. Pat. No. 9,104,271 (Adams et al., Aug. 11, 2015, "Gloved Human-Machine Interface"). Prior art which appears to be in this category also includes U.S. patent application 20150233779 (Chen et al., Aug. 20, 2015, "Gloves with Pressure Sensors").

Art in this next category comprises at least one pressure sensor in a fingertip or thimble embodiment. Prior art which appears to be in this category includes the following U.S. patents: U.S. Pat. No. 6,380,923 (Fukumoto et al., Apr. 30, 2002, "Full-Time Wearable Information Managing Device and Method for the Same"); U.S. Pat. No. 6,622,575 (Nagata, Sep. 23, 2003, "Fingertip-Mounted Six-Axis Force Sensor"); and U.S. Pat. No. 8,373,656 (Hou et al., Feb. 12, 2013, "Finger Pointing Apparatus"). Prior art which appears to be in this category also includes U.S. patent application 20090278798 (Kim et al., Nov. 12, 2009, "Active Fingertip-Mounted Object Digitizer").

Art in this next category comprises at least one touchpad in a glove embodiment. Prior art which appears to be in this category includes the following U.S. patents: U.S. Pat. No. 4,414,537 (Grimes, Nov. 8, 1983, "Digital Data Entry Glove Interface Device"); U.S. Pat. No. 6,128,004 (McDowall et al., Oct. 3, 2000, "Virtual Reality Glove System with Fabric Conductors"); U.S. Pat. No. 6,141,643 (Harmon, Oct. 31, 2000, "Data Input Glove Having Conductive Finger Pads and Thumb Pad, and Uses Therefor"); U.S. Pat. No. 7,498,956 (Baier et al., Mar. 3, 2009, "Apparatus and Method for Inputting Information"); U.S. Pat. No. 7,917,235 (Miller, Mar. 29, 2011, "Apparatus for Remotely Controlling Computers and Other Electronic Appliances/Devices using a Combination of Voice Commands and Finger Movements"); U.S. Pat. No. 8,386,060 (Miller, Feb. 26, 2013, "Apparatus for Remotely Controlling Computers and Other Electronic Appliances/Devices using a Combination of Voice Commands and Finger Movements"); U.S. Pat. No. 8,686,947 (Wine, Apr. 1, 2014, "Finger Keypad System and Method"); and U.S. Pat. No. 8,755,912 (Miller, Jun. 17, 2014, "Apparatus for Remotely Controlling Computers and Other Electronic Appliances/Devices Using a Combination of Voice Commands and Finger Movements"). Prior art which appears to be in this category also includes the following U.S. patent applications: 20060214912 (Miller, Sep. 28, 2006, "Apparatus for Remotely Controlling Computers and Other Electronic Appliances/Devices Using a Combination of Voice Commands and Finger Movements"); 20100207881 (Miller, Aug. 19, 2010, "Apparatus for Remotely Controlling Computers and Other Electronic Appliances/Devices Using a Combination of Voice Commands and Finger Movements"); 20110260963 (Timmons, Oct. 27, 2011, "Symbolic Input Via Mid-Air Finger/Thumb Motions"); 20130135240 (Miller, Aug. 19, 2010, "Apparatus for Remotely Controlling Computers and Other Electronic Appliances/Devices Using a Combination of Voice Commands and Finger Movements"); and 20140240214 (Liu et al., Aug. 28, 2014, "Glove Interface Apparatus for Computer-Based Devices").

Art in this next category comprises at least one touchpad in a finger sleeve embodiment. Prior art which appears to be in this category includes U.S. Pat. No. 8,681,101 (Haney et al., Mar. 25, 2014, "Finger Mounted Input Device").

Art in this next category comprises at least one touchpad in a clothing embodiment. Prior art which appears to be in this category includes U.S. patent application 20150370320 (Connor, Dec. 24, 2015, "Smart Clothing with Human-To-Computer Textile Interface").

Art in this next category comprises at least one EMG sensor in a wrist or armband embodiment. Prior art which appears to be in this category includes the following U.S. patents: U.S. Pat. No. 8,170,656 (Tan et al., May 1, 2012, "Wearable Electromyography-Based Controllers for Human-Computer Interface"); U.S. Pat. No. 8,447,704 (Tan et al., May 31, 2013, "Recognizing Gestures from Forearm EMG Signals"); U.S. Pat. No. 8,581,856 (Benko et al., Nov. 12, 2013, "Touch Sensitive Display Apparatus Using Sensor Input"); U.S. Pat. No. 8,892,479 (Tan et al., Nov. 18, 2014, "Recognizing Finger Gestures from Forearm EMG Signals"); U.S. Pat. No. 9,037,530 (Tan et al., May 19, 2015, "Wearable Electromyography-Based Human-Computer Interface"); and U.S. Pat. No. 9,299,248 (Lake et al., Mar. 29, 2016, "Method and Apparatus for Analyzing Capacitive EMG and IMU Sensor Signals for Gesture Control"). Prior art which appears to be in this category also includes the following U.S. patent applications: 20090326406 (Tan et al., Dec. 31, 2009, "Wearable Electromyography-Based Controllers for Human-Computer Interface"); 20100302137 (Benko et al., Dec. 2, 2010, "Touch Sensitive Display Apparatus Using Sensor Input"); 20120188158 (Tan et al., Jul. 26, 2012, "Wearable Electromyography-Based Human-Computer Interface"); 20130232095 (Tan et al., Sep. 5, 2013, "Recognizing Finger Gestures from Forearm EMG Signals"); 20140240103 (Lake et al., Aug. 28, 2014, "Methods and Devices for Combining Muscle Activity Sensor Signals and Inertial Sensor Signals for Gesture-Based Control"); and 20150169074 (Ataee et al., Jun. 18, 2015, "Systems, Articles, and Methods for Gesture Identification in Wearable Electromyography Devices").

Art in this next category comprises at least one EMG sensor in a clothing embodiment. Prior art which appears to be in this category includes U.S. Pat. No. 9,278,453 (Assad, Mar. 8, 2016, "Biosleeve Human-Machine Interface"). Prior art which appears to be in this category also includes the following U.S. patent applications: 20130317648 (Assad, Nov. 28, 2013, "Biosleeve Human-Machine Interface"); and 20150366504 (Connor, Dec. 24, 2015, "Electromyographic Clothing").

Art in this next category comprises at least one other electromagnetic sensor embodiment. Prior art which appears to be in this category includes the following U.S. patents:

U.S. Pat. No. 5,980,472~D=Seyl, Nov. 9, 1999, "Joint Movement Monitoring System"); and U.S. Pat. No. 6,334,852 (Seyl, Jan. 1, 2002, "Joint Movement Monitoring System").

Art in this next category comprises at least one RFID embodiment. Prior art which appears to be in this category includes U.S. Pat. No. 8,493,174 (Agrawal, Jul. 23, 2013, "Apparatus for Instantaneous Translation of Sign Language"). Prior art which appears to be in this category also includes the following U.S. patent applications: 20040210166 (Soh et al., Oct. 21, 2004, "Apparatus and Method for Detecting Finger-Motion"); and 20110234384 (Agrawal, Sep. 29, 2011, "Apparatus for Instantaneous Translation of Sign Language").

Art in this next category include other potentially relevant art that does not fit into one of the above categories. Prior art which appears to be in this category includes the following U.S. patents: U.S. Pat. No. 5,964,701 (Asada et al., Oct. 12, 1999, "Patient Monitoring Finger Ring Sensor"); U.S. Pat. No. 6,402,690 (Rhee et al., Jun. 11, 2002, "Isolating Ring Sensor Design"); and U.S. Pat. No. 9,261,983 (Bailen, Feb. 16, 2016, "Fingertip Mouse and Base"). Prior art which appears to be in this category also includes the following U.S. patent applications: 20110007035 (Shai, Jan. 13, 2011, "Finger-Worn Devices and Related Methods of Use"); and 20150185971 (Gomez et al., Jul. 2, 2015, "Ring-Based User-Interface").

SUMMARY OF THIS INVENTION

This invention is a wearable device or system for measuring finger motion and recognizing hand gestures. In an example, this wearable device or system for measuring finger motion and recognizing hand gestures can serve as a Human-to-Computer Interface (HCI). In an example, such a wearable device or system can be especially useful for: communication from a human to a small-scale computing device wherein touch-based communication is challenging; human-to-computer communication in a noisy environment wherein voice-based communication is difficult; human-to-computer communication in a public environment wherein voice-based communication is neither private nor considerate; and human-to-computer communication involving complex manipulation of objects in three-dimensional space.

In an example, this invention can be embodied in a distal loop which encircles the intermediate phalanx of a finger, a proximal loop which encircles the proximal phalanx of the finger, a joint-spanning strip which connects these two loops, and a bend sensor which is part of the joint-spanning strip. Changes in energy transmitted through, or generated by, the bend sensor are used to measure the motion and/or configuration of the proximal interphalangeal joint.

In an example, this invention can be embodied in one or more inertial motion sensors which are removably attached to one or more finger nails. In an example, an inertial motion sensor can be directly attached to a finger nail by adhesion. In an example, an inertial motion sensor can be removably attached to a base member, wherein the base member is attached to a finger nail. In an example, an inertial motion sensor can be attached to a base member by insertion into a groove, opening, or hole in the base member. In an example, an inertial motion sensor can be attached to base member by a snap, clip, clasp, hook, pin, button, plug, or magnet.

BRIEF INTRODUCTION TO THE FIGURES

FIG. 1 shows two finger rings with inertial motion sensors.

FIG. 54 shows a holey elastic band with a wider dorsal portion and a motion sensor.

DETAILED DESCRIPTION OF THE FIGURES

Figure 1:
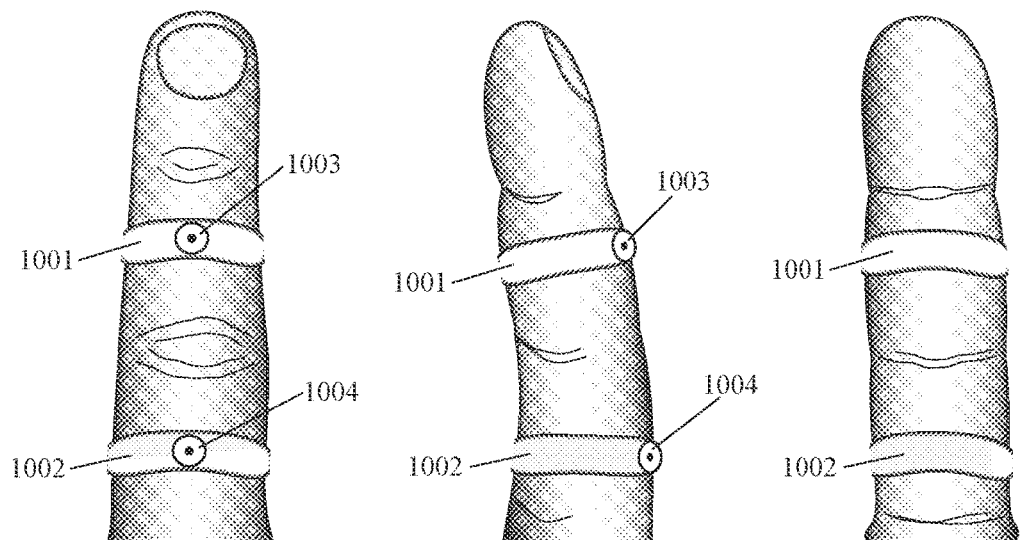
FIGS. 1 through 54 show examples of how this invention can be embodied in a wearable device or system for measuring finger motion and recognizing hand gestures, but they do not limit the full generalizability of the claims.
Figure 54:
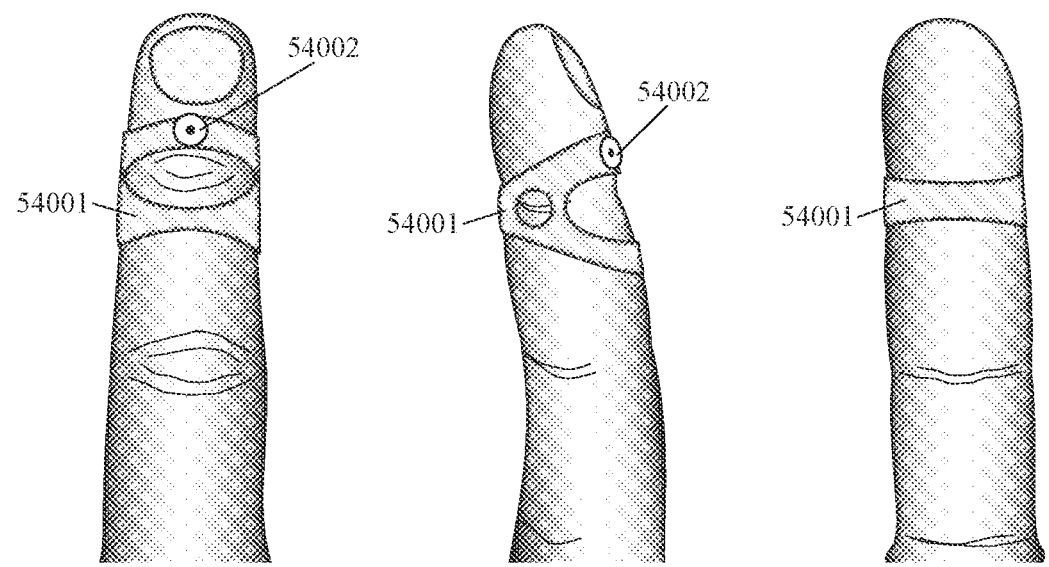

FIGS. 1 through 54 show examples of how this invention can be embodied in a wearable device or system for measuring finger motion and recognizing hand gestures, but they do not limit the full generalizability of the claims.

The terms "distal" and "proximal" have established meanings in the medical field when they are used for the names of specific bones (e.g. the "distal phalanx" and the "proximal phalanx") and joints (e.g. the "distal interphalangeal joint" and the "proximal interphalangeal joint") of the human hand. In this disclosure, when the terms "distal" and "proximal" are used for the names of these bones and joints, they have their established meanings from the medical field. In this disclosure, when the terms "distal" and "proximal" are used more generally: the term "distal" refers to locations in (or on) the person's body which are further from the person's mass centroid or from the person's heart; and the term "proximal" refers to locations in (or on) the person's body which are closer to the person's mass centroid or to the person's heart.

FIG. 1 shows a first example of how this invention can be embodied in a wearable device for measuring finger motion and recognizing hand gestures. The left third of FIG. 1 shows this device from a top-down perspective, looking at the upper (dorsal) surface of a person's finger. The middle third of FIG. 1 shows this same device from a side perspective, with the finger having been rotated 90 degrees clockwise. The right third of FIG. 1 shows this same device from a bottom-up perspective, looking at the lower (ventral) surface of the finger.

Looking at components in detail, FIG. 1 shows a wearable device for measuring finger motion and recognizing gestures comprising: a first finger ring 1001 which is configured to be worn around the intermediate phalanx of a finger; a second finger ring 1002 which is configured to be worn around the proximal phalanx of the finger; a first inertial motion sensor 1003 which is part of the first finger ring 1001; and a second inertial motion sensor 1004 which is part of the second finger ring 1002.

In an example, a finger ring can be made of metal or polymer. In an example, the shape of a finger ring can be circular, cylindrical, elliptical, and/or toroidal. In an example, a finger ring can have a bulge, protrusion, and/or ornamental member on its upper (dorsal) portion. In an example, an inertial motion sensor can be selected from the group consisting of: multi-axial accelerometer, gyroscope, and inclinometer. In an example, there can be multiple inertial motion sensors and/or different types of inertial motion sensors on a single finger ring. In an example, an inertial motion sensor can be inside the main volume of a finger ring. In an example, an inertial motion sensor can be attached to the surface of a finger ring. In an example, an inertial motion sensor can be modular and removably attached to the surface of a finger ring.

In an example, the device shown in FIG. 1 can be part of a system for measuring the motions and configurations of multiple fingers and for recognizing multi-finger hand gestures. In an example, there can be one such device on each of a person's fingers and thumb. In another example, such devices can be worn on a subset of a person's fingers and thumb. In an example, one such device can be worn on a person's index finger and one such device can be worn on the person's thumb. In an example, such a device can be worn on a person's index finger. In an example, such a device can be only on a person's ring finger.

In the example shown in FIG. 1, an inertial motion sensor is part of the upper (dorsal) portion of a finger ring. In another example, an inertial motion sensor can be located on the lateral side of a finger ring. In an example, an inertial motion sensor can be part of the lower (ventral) portion of a finger ring. In this example, first and second finger rings 1001 and 1002 are worn around the intermediate phalanx and the proximal phalanx of a finger, respectively. In another example, first and second finger rings can be worn around the distal phalanx and the proximal phalanx, respectively, of a finger or a thumb. In an alternative example, first and second finger rings can be worn on the distal phalanx and the intermediate phalanx of a finger, respectively. In an example, there can be three rings—one each on the distal phalanx, the intermediate phalanx, and the proximal phalanx of a finger.

In an example, a finger ring can further comprise one or more components selected from the group consisting of: power source; energy transducer; data processing unit; wireless data transmitter; wireless data receiver; computer-to-human interface; microphone; camera; compass; pressure sensor; electromagnetic sensor; and GPS component. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger rings are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger rings are in wireless communication with a handheld computing device. A handhand computing device can be selected from the group consisting of: smart phone or other mobile phone; electronic pad or tablet, and other portable computer.

In an example, differences in the motion of a first inertial motion sensor versus the motion of a second inertial motion sensor can be analyzed in order to estimate the bending motion of a proximal interphalangeal joint and/or a distal interphalangeal joint. In an example, similarities in the motions of a first inertial motion sensor and a second inertial motion sensor can be analyzed in order to estimate the overall motion of (the centroid of) a person's finger. In an example, differences in the three-dimensional angular orientations or configurations of a first inertial motion sensor versus a second inertial motion sensor can be analyzed in order to estimate the bend angle of an interphalangeal joint and to recognize finger configuration.

In an example, differences in the motion of inertial motion sensors on a first finger versus inertial motion sensors on a second finger can be analyzed in order to estimate the bending motion of meta-carpophalageal joints. In an example, similarities in the motions of inertial motion sensors on a first finger and inertial motion sensors on a second finger can be analyzed in order to estimate the overall motion of (the centroid of) a person's hand. In an example, differences in the three-dimensional angular orientations of inertial motion sensors on a first finger versus inertial motion sensors on a second finger can be analyzed in order to estimate the bend angles of meta-carpophalageal joints and to recognize hand configuration.

In an example, data from multiple inertial motion sensors on multiple fingers can be received and analyzed by a data processing unit in order to recognize hand gestures. In an example, this data processing unit can be part of a finger ring. In an example, this data processing unit can be part of a separate wearable or handheld device with which finger rings are in wireless communication. In an example, this data processing unit can be in a remote computer which is accessible via a data network.

In an example, hand gestures can be recognized based on one or more factors selected from the group consisting of: estimated joint angles for the distal interphalangeal, intermediate interphalangeal, and meta-carpophalageal joints; estimated roll, pitch, and yaw of the hand centroid; estimated three-dimensional orientation the hand centroid; modeled three-dimensional configuration of the distal, intermediate, and proximal phalanges; movement directions and speeds for the finger rings; roll, pitch, and yaw of the finger rings; three-dimensional orientations of finger rings; and three-dimensional orientations of the distal, intermediate, and proximal phalanges.

In various examples, this wearable device or a system comprising multiple such wearable devices can recognize one or more hand gestures selected from the group consisting of: "finger tap" (palm facing down with index tip moving down and up once); "finger double tap" (palm facing down with index tip moving down and up twice quickly); "finger press" (palm facing down with index tip pressing down for extended time); "finger slide right" (palm facing down with index or middle tip moving right and arcing left); "finger slide left" (palm facing down with index or middle tip moving left and arcing right); "finger rub" (palm facing down with index or middle tip moving back and forth); "finger scroll down" (palm facing down with index or middle tip moving down and arcing up); "finger scroll up" (palm facing down with index or middle tip moving up and arcing down); "finger clockwise" (index or middle tip moving in a clockwise circle or arc of a circle); "finger counter-clockwise" (index or middle tip moving in a counter-clockwise circle or arc of a circle); "finger figure eight" (index or middle tip moving in a figure eight); "finger pinch" (thumb and index or middle tip moving closer); "finger spread" (thumb and index or middle tip moving apart); "finger merge" (index tips from both hands moving together); "finger divide" (index tips from both hands moving apart); "grasp" (thumb and aligned fingers touch to form a "C"); "drink" (thumb and aligned fingers form a "C" and hand rotating toward person); "grab" (thumb and four fingers contracting simultaneously); "move down" (palm facing down with hand pivoting downward from wrist and/or elbow); "move up" (palm facing up with hand pivoting upward from wrist and/or elbow); "move right" (palm facing sideways with hand pivoting rightward from wrist); "move left" (palm facing sideways with hand pivoting leftward from wrist); "hand rotation clockwise" (flat hand rotating clockwise); "hand rotation counter-clockwise" (flat hand rotating counter-clockwise); "hold and turn clockwise" (first with thumb and index extended and rotating clockwise); "hold and turn counter-clockwise" (first with thumb and index extended and rotating counter-clockwise); "outward palm" (flat hand with palm outward and thumb and all fingers extended); "hand wave" (flat hand with palm outward and side-to-side motion); "chop" (flat hand with palm downward and side-to-side motion); "fist" (thumb and all fingers contracted); "fist pump" (upright first moving up and down); "fist bang or first bump" (extended first moving down and up); "knock" (first pivoting downward from wrist); "thumbs down" (first with thumb extended downwards); "thumbs up" (first with thumb extended upward); "point" (first with index tip extended outward); "gun" (vertical first with index and middle extended outward together); "V" or "peace sign" (outward-facing first with index and middle extended upwards apart); "scissors" (first with index and middle apart and then together); "Vulcan salute" (outward-facing palm with fingers up and separated between middle and ring); "cuckold/horns" (hand vertical with index and pithy upward); "middle finger" (upward first with middle extended upward); "call me" (vertical first with thumb and pinky extended); "hang loose" (horizontal palm with thumb and pinky extended); "I Love You" (thumb, index, and pinky extended while middle and ring touch palm); "OK" (thumb and index form a circle); "loser" (first with thumb and index finger extended at a right angle); "no" (first with raised extended index moving side to side); "finger cross" (thumb and middle fingers crossed); "finger snap" (middle sliding quickly from tip to base of thumb); "money" (tips of middle and thumb rubbing back and forth on each other); "come here" (upward or sideways facing first with index tip extended and moving inward); "blah blah" (thumb and horizontal extended fingers opening and closing together); "I think you are a troll" (index of one hand touching palm of other hand); "world's smallest violin" (first with thumb and index extended and rubbing); "writing" (first with thumb and index touching and moving together); "thumb to index" (thumb tip touching index finger tip); "thumb to middle" (thumb tip touching middle finger tip); "thumb to ring" (thumb tip touching ring finger tip); "thumb to pinky" (thumb tip touching pinky tip); a gesture indicating a selected letter in sign language; and a gesture indicating a selected word in sign language. Other relevant design variations discussed with respect to other examples in this description can also apply to the example shown here in FIG. 1.

Figure 2:
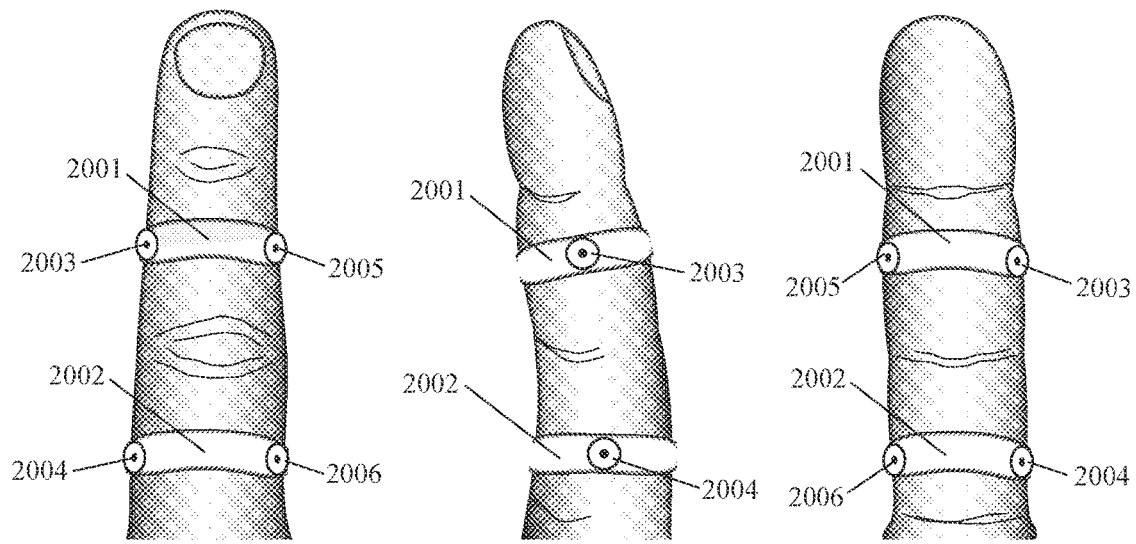
FIG. 2 shows two finger rings with multiple inertial motion sensors.

FIG. 2 shows another example of how this invention can be embodied in a wearable device for measuring finger motion and recognizing hand gestures. The example shown in FIG. 2 is like the one shown in FIG. 1 except that there are multiple inertial motion sensors on each finger ring. Specifically, FIG. 2 shows a wearable device for measuring finger motion and recognizing gestures comprising: a first finger ring 2001 which is configured to be worn around the intermediate phalanx of a finger; a second finger ring 2002 which is configured to be worn around the proximal phalanx of the finger; first and second inertial motion sensors 2003 and 2005 which are part of first finger ring 2001; and third and fourth inertial motion sensors 2004 and 2006 which are part of second finger ring 2002.

In this example, each finger ring has two inertial motion sensors—one inertial motion sensor on its upper (dorsal) portion and one inertial motion sensor on its lateral side. In an example, there can be one motion sensor on the upper (dorsal) portion of a ring and one motion sensor on the lower (ventral) portion of a ring. In an example, there can be three or more inertial motion sensors on a finger ring. In an example, motion data from multiple motion sensors on the same ring can be averaged to achieve more accurate motion information. In an example, a second sensor may only be activated when a first sensor appears to be malfunctioning. Other relevant design variations discussed with respect to other examples in this description can also apply to the example shown here in FIG. 2.

Figure 3:
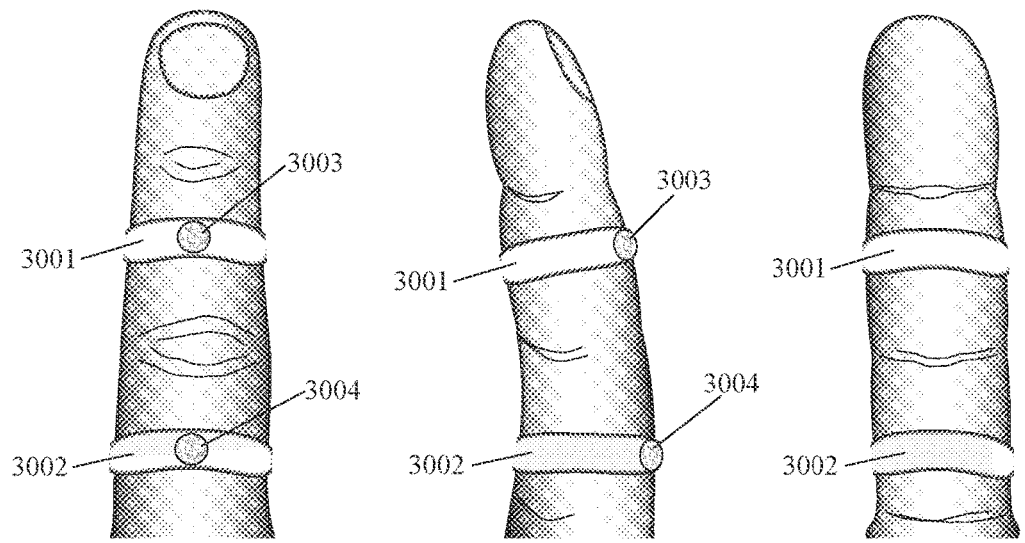
FIG. 3 shows two finger rings with light reflectors.

FIG. 3 shows another example of how this invention can be embodied in a wearable device for measuring finger motion and recognizing hand gestures. This example is similar to the one shown in FIG. 1 except that it has light-energy reflectors instead of inertial motion sensors. The left third of FIG. 3 shows this device from a top-down perspective, looking at the upper (dorsal) surface of a person's finger. The middle third of FIG. 3 shows this same device from a side perspective, with the finger having been rotated 90 degrees clockwise. The right third of FIG. 3 shows this same device from a bottom-up perspective, looking at the lower (ventral) surface of the finger.

Looking at device components in more detail, FIG. 3 shows a wearable device for measuring finger motion and recognizing gestures comprising: a first finger ring 3001 which is configured to be worn around the intermediate phalanx of a finger; a second finger ring 3002 which is configured to be worn around the proximal phalanx of the finger; a first light-energy reflector 3003 which is part of first finger ring 3001; and a second light-energy reflector 3004 which is part of second finger ring 3002.

In an example, a finger ring can be a band made of metal or polymer. In an example, a finger ring can be generally cylindrical or toroidal. In an example, a finger ring can have a bulge, protrusion, and/or ornamental member on its upper (dorsal) portion. In an example, a light-energy reflector can have a reflective and/or shiny surface which reflects light energy hitting it from an external source. In an example, the external light source can be an environmental light source, such as the sun or nearby artificial lighting in the environment. In an example, the external light source can be part of a separate wearable device. In an example, the light source can be a source of infrared or near-infrared light source. In an example, the light source can be a source of polarized or coherent light.

In an example, a light-energy reflector can have a unique reflective color, wavelength, spectrum, polarization, light pattern, and/or shape which enables it to be differentiated from other light-energy reflectors and/or uniquely identified. In an example, this device can be part of a system for measuring finger motion and recognizing gestures which further comprises a camera which tracks the locations of light-energy reflectors worn on the fingers. In an example, this camera can be incorporated into smart glasses or other electronically-functional eyewear, an EEG monitor, a hat, cap, or visor, a smart necklace, a wearable button, and/or an upper body garment. In an example, analysis of images captured by the camera can identify the locations of light-energy reflectors based on their unique reflective colors, wavelengths, spectrums, polarizations, light patterns, and/or shapes.

In the example shown in FIG. 3, light-energy members are passive light-energy reflectors. In an alternative example, light-energy members can be active light-energy emitters, such as LEDs. In an example, each finger ring can have one or more light-energy emitters, such as LEDs, whose locations are tracked by a camera. In an example, this camera can be part of smart glasses or other electronically-functional eyewear in order to measure finger motion and recognize hand gestures. In an example, a specific light-energy emitter can emit light with a unique color, wavelength, polarization, or pattern which enables it to be differentiated from other light-energy emitters in a finger-worn device or a system of finger-worn devices.

In an example, the example shown in FIG. 3 can be part of a system for measuring finger motion and recognizing gestures comprising: a plurality of finger rings worn on a person's fingers; a plurality of light-energy reflectors which are part of the finger rings; electronically-functional eyewear; and a camera which is part of the eyewear, wherein analysis of images captured by the camera is used to identify the locations of the light-energy reflectors and to recognize hand gestures based on the relative locations of the light-energy reflectors. In an example, each of the light-energy reflectors has a unique color, wavelength, spectrum, polarization, pattern, or shape which is identified in the images captured by the camera. In an example, this system can function as a gesture-based human-to-computer interface.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In this example, light-energy reflectors 3003 and 3004 are parts of the upper (dorsal) portions of the finger rings. In another example, inertial motion sensors can be parts of the side portions of finger rings. In this example, first and second finger rings 3001 and 3002 are worn around the intermediate phalanx and the proximal phalanx of a finger, respectively. In another example, first and second finger rings can be worn around the distal phalanx and the proximal phalanx, respectively, of a finger or a thumb. In an alternative example, first and second finger rings can be worn on the distal phalanx and the intermediate phalanx of a finger, respectively. In an example, there can be three rings, one each on the distal phalanx, the intermediate phalanx, and the proximal phalanx of a finger.

In an example, a finger ring can further comprise one or more components selected from the group consisting of: power source; energy transducer; data processing unit; wireless data transmitter; wireless data receiver; computer-to-human interface; microphone; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger rings are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger rings are in wireless communication with a handheld computing device. A handhand computing device can be selected from the group consisting of: smart phone or other mobile phone; electronic pad or tablet, and other portable computer.

In an example, differences in the motion of a first light-energy reflector versus the motion of a second light-energy reflector can be analyzed in order to estimate the bending motion of a proximal interphalangeal joint and/or a distal interphalangeal joint. In an example, similarities in the motions of a first light-energy reflector and a second light-energy reflector can be analyzed in order to estimate the overall motion of (the centroid of) a person's finger. In an example, differences in the angular orientations of a first light-energy reflector versus a second light-energy reflector can be analyzed in order to estimate the bend angle of a proximal interphalangeal joint and to recognize finger configuration.

In an example, differences in the motion of light-energy reflectors on a first finger versus light-energy reflectors on a second finger can be analyzed in order to estimate the bending motion of meta-carpophalageal joints. In an example, similarities in the motions of light-energy reflectors on a first finger and light-energy reflectors on a second finger can be analyzed in order to estimate the overall motion of (the centroid of) a person's hand. In an example, data from multiple light-energy reflectors on multiple fingers can be received and analyzed by a data processing unit in order to recognize hand gestures. In an example, this data processing unit can be part of a finger ring. In an example, this data processing unit can be part of a separate wearable or handheld device with which finger rings are in wireless communication. Other relevant design variations discussed with respect to other examples in this description can also apply to the example shown here in FIG. 3.

Figure 4:
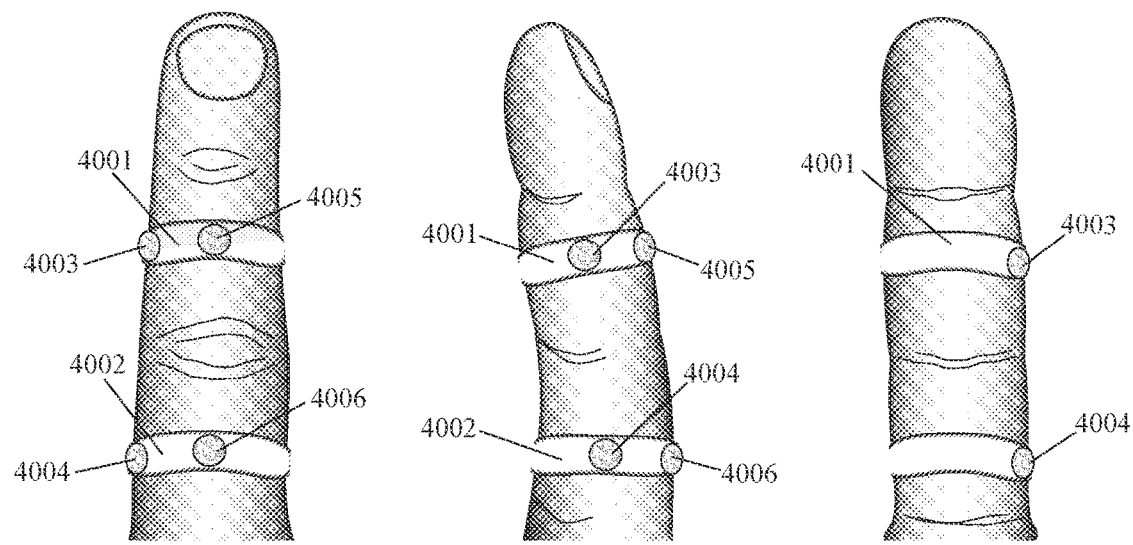
FIG. 4 shows two finger rings with multiple light reflectors.

FIG. 4 shows another example of how this invention can be embodied in a wearable device for measuring finger motion and recognizing hand gestures. The example shown in FIG. 4 is like the one shown in FIG. 3 except that there are multiple light-energy reflectors on each finger ring. Specifically, FIG. 4 shows a wearable device for measuring finger motion and recognizing gestures comprising: a first finger ring 4001 which is configured to be worn around the intermediate phalanx of a finger; a second finger ring 4002 which is configured to be worn around the proximal phalanx of the finger; first and second light-energy reflectors 4003 and 4005 which are part of first finger ring 4001; and third and fourth light-energy reflectors 4004 and 4006 which are part of second finger ring 4002. Other relevant design variations discussed with respect to other examples in this description can also apply to the example shown here in FIG. 4.

Figure 5:
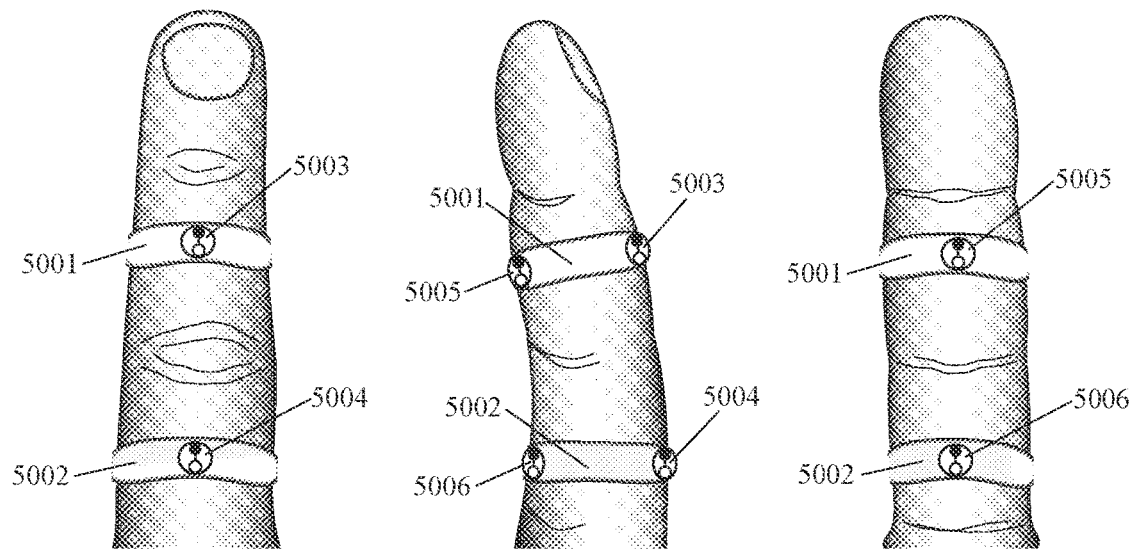
FIG. 5 shows two finger rings with electromyographic (EMG) sensors.

FIG. 5 shows another example of how this invention can be embodied in a wearable device for measuring finger motion and recognizing hand gestures. This example is similar to the one shown in FIG. 1 except that it has electromagnetic energy sensors. The left third of FIG. 5 shows this device from a top-down perspective, looking at the upper (dorsal) surface of a person's finger. The middle third of FIG. 5 shows this same device from a side perspective, with the finger having been rotated 90 degrees clockwise. The right third of FIG. 5 shows this same device from a bottom-up perspective, looking at the lower (ventral) surface of the finger.

Although a finger is moved by muscles which are proximal to a phalanx, electromagnetic energy patterns from the relevant muscles may still be detectable by an electromagnetic energy sensor on a finger ring. Electromyography (EMG) is a method of measuring changes in electromagnetic energy which are produced by the activity of muscles and/or the nerves which innervate those muscles. These changes in electromagnetic energy are called electromyographic signals ("EMG signals"). Muscles are controlled by motor neurons. Electrical signals transmitted by these motor neurons cause innervated muscles to contract. The electrical signals transmitted by nerves are called action potentials. These action potentials are particularly active during muscle fiber contraction. The electrical potential associated with muscle contraction is generally proportional to the strength of contraction. Accordingly, EMG signals are generally stronger during more-rigorous muscle contraction.

Electromyographic sensors ("EMG sensors") are electromagnetic energy sensors which are placed in proximity to one or more muscles and/or nerves in order to measure the electromagnetic energy created by these muscles and/or nerves during muscle activation. The combination of a motor neuron and the muscle fibers which that neuron innervates is called a motor unit. An EMG sensor at a particular location can measure the accumulated electromagnetic energy from multiple nearby motor units, especially if the EMG sensor is a surface EMG sensor that does not penetrate the person's skin. In an example, an EMG signal can be a composite of action potentials from multiple motor units. Decomposing a composite EMG signal to infer the action potentials (and motions) or individual motor units can be challenging, but can be possible because different motor units can have different electromagnetic signal patterns.

In an example, an EMG sensor can be a bipolar EMG sensor. A bipolar EMG sensor comprises a ground electrode and a sensor electrode. In an example, multiple mono-pole EMGs can share a common ground (or reference) electrode. In an example, two electrodes can be coupled with an amplifier which increases the voltage difference between them. In an example, the output of the amplifier can be sent to an analog-to-digital converter. In an example, changes in electromagnetic energy can be measured by one or more parameters selected from the group consisting of: voltage, resistance, impedance, amperage, current, phase, and wave pattern.

In an example, an EMG sensor can be a surface EMG sensor ("sEMG") which is in direct contact with a person's skin in proximity to the muscles and/or nerves being measured. A surface EMG sensor measures the combined electromagnetic energy which reaches a person's skin from underlying electrical potentials that travel along one or more nearby contracting muscles. As contraction of muscle fibers increases and/or more muscle fibers contract, the resulting electrical potential increases and can be measure from the surface of the person's skin. Contraction of a muscle fiber is followed by relaxation of that fiber. The sequential contraction and relation of a muscle fiber comprises a muscle "twitch." Muscles include fast twitch fibers and slow twitch fibers with different force dynamics.

In an example, an EMG sensor can be a contactless EMG sensor which is close to the person's skin but not in direct contact. In an example, electromagnetic current can be created within an EMG sensor by conduction. In an example, electromagnetic current can be created within an EMG sensor by induction. In an example, electromagnetic current can be created with an EMG sensor by capacitance.

We now apply this discussion of electromyography to the example shown in FIG. 5. FIG. 5 shows an example of a wearable device for measuring finger motion and recognizing gestures comprising: a first finger ring 5001 which is configured to be worn around the intermediate phalanx of a finger; a second finger ring 5002 which is configured to be worn around the proximal phalanx of the finger; a first electromagnetic energy sensor 5003 which is part of the dorsal portion of first finger ring 5001; a second electromagnetic energy sensor 5004 which is part of the dorsal portion of second finger ring 5002; a third electromagnetic energy sensor 5005 which is part of the ventral portion of first finger ring 5001; and a fourth electromagnetic energy sensor 5006 which is part of the ventral portion of second finger ring 5002. In an example, an electromagnetic energy sensor can be an EMG sensor. In an example, electromagnetic energy sensors can be bipolar. In an example, the two poles can be generally aligned with the longitudinal axis of a phalanx—with one pole of the sensor being more distal and the other pole being more proximal.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In this example, first and second finger rings 5001 and 5002 are worn around the intermediate phalanx and the proximal phalanx of a finger, respectively. In another example, first and second finger rings can be worn around the distal phalanx and the proximal phalanx of a finger or a thumb. In an alternative example, first and second finger rings can be worn on the distal phalanx and the intermediate phalanx of a finger, respectively. In an example, there can be three rings, one each on the distal phalanx, the intermediate phalanx, and the proximal phalanx of a finger.

In an example, a finger ring can further comprise one or more components selected from the group consisting of: power source; energy transducer; data processing unit; wireless data transmitter; wireless data receiver; computer-to-human interface; microphone; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger rings are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger rings are in wireless communication with a handheld computing device. A handhand computing device can be selected from the group consisting of: smart phone or other mobile phone; electronic pad or tablet, and other portable computer.

In an example, patterns of electromagnetic energy measured by electromagnetic energy sensors can be analyzed in order to estimate the bending motion of a distal interphalangeal joint, a proximal interphalangeal joint, and/or a meta-carpophalageal joint. In an example, data from multiple electromagnetic energy sensors on multiple fingers can be received and analyzed by a data processing unit in order to recognize hand gestures. In an example, this data processing unit can be part of a finger ring. In an example, this data processing unit can be part of a separate wearable or handheld device with which finger rings are in wireless communication. Other relevant design variations discussed with respect to other examples in this description can also apply to the example shown here in FIG. 5.

Figure 6:
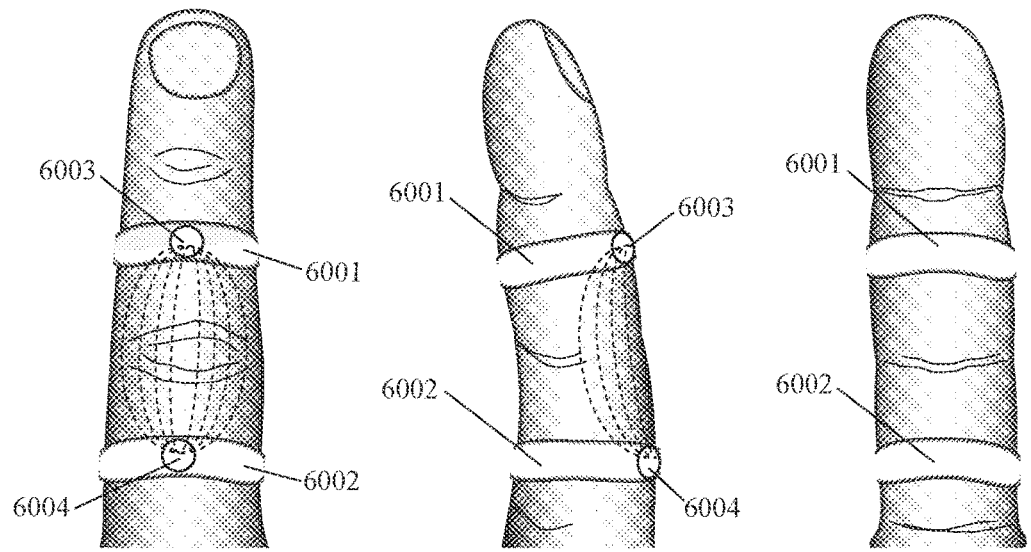
FIG. 6 shows two finger rings with electromagnetic energy transmitter and receiver.

FIG. 6 shows another example of how this invention can be embodied in a wearable device for measuring finger motion and recognizing hand gestures. Like the one shown in FIG. 5, the example shown in FIG. 6 also has an electromagnetic energy sensor, but this sensor measures electromagnetic energy signals that are created by the device instead of electromagnetic energy signals which are created naturally by muscles and/or nerves. The left third of FIG. 6 shows this device from a top-down perspective, looking at the upper (dorsal) surface of a person's finger. The middle third of FIG. 6 shows this same device from a side perspective, with the finger having been rotated 90 degrees clockwise. The right third of FIG. 6 shows this same device from a bottom-up perspective, looking at the lower (ventral) surface of the finger.

More specifically, FIG. 6 shows an example of a wearable device for measuring finger motion and recognizing gestures comprising: a first finger ring 6001 which is configured to be worn around the intermediate phalanx of a finger; a second finger ring 6002 which is configured to be worn around the proximal phalanx of the finger; an electromagnetic energy emitter 6003 which is part of first finger ring 6001; and an electromagnetic energy sensor 6004 which is part of second finger ring 6002.

In an example, electromagnetic energy sensor 6004 detects the relative proximity and/or orientation of electromagnetic energy emitter 6003 and, thus, the proximity and/or orientation of finger ring 6002 relative to finger ring 6001. In an example, electromagnetic energy emitted from emitter 6003 can be conducted through finger tissue to sensor 6004. In an example, electromagnetic energy emitted from emitter 6003 can be transmitted through the air to sensor 6004. In an example, electromagnetic energy emitter 6003 can create an electromagnetic energy field which is detected by electromagnetic energy sensor 6004. In an example, changes in the proximity of electromagnetic energy emitter 6003 to sensor 6004 can be estimated by measuring changes in the strength of the electromagnetic field as measured by sensor 6004. In an example, changes in the orientation of electromagnetic energy emitter 6003 relative to sensor 6004 can be estimated by measuring changes in the electromagnetic field as measured by sensor 6004.

In this example, electromagnetic energy sensor 6004 is distal relative to electromagnetic energy emitter 6003. In another example, an electromagnetic energy sensor can be proximal relative to electromagnetic energy emitter. In an example, an electromagnetic energy sensor can be bipolar. In an example, an electromagnetic energy emitter can be bipolar. In an example, an electromagnetic energy sensor can be shaped like a torus. In an example, an electromagnetic energy emitter can shaped like a torus. In an example, an electromagnetic energy sensor can be helical in shape. In an example, an electromagnetic energy emitter can be helical in shape. In an example, an electromagnetic energy sensor can be a solenoid. In an example, an electromagnetic energy emitter can be a solenoid.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, different electromagnetic energy emitters worn on different fingers can emit electromagnetic energy with different patterns including variation in power, amplitude, frequency, wavelength, and/or waveform. In an example, electromagnetic energy measured by sensors worn on different fingers can be analyzed to model the locations and/or orientations of phalanges relative to each other. In an example, an electromagnetic energy emitter and an electromagnetic energy sensor can be parts, respectively, of the upper (distal) portions of finger rings.

In an example, the device is FIG. 6 can also comprise accelerometers. In an example, in order to conserve energy use, electromagnetic energy emitters may only be activated to emit energy when an accelerometer indicates that a finger is moving. In an example, measuring finger movement using paired electromagnetic energy emitters and sensors may be more accurate than using paired accelerometers, but also require more energy. Using a lower-energy sensor (e.g. an accelerometer) to selectively activate a higher-energy sensor (e.g. paired electromagnetic energy emitter and sensor) when there is motion can achieve higher measurement accuracy while conserving energy use.

In this example, first and second finger rings 6001 and 6002 are worn around the intermediate phalanx and the proximal phalanx of a finger, respectively. In another example, first and second finger rings can be worn around the distal phalanx and the proximal phalanx of a finger or a thumb. In an alternative example, first and second finger rings can be worn on the distal phalanx and the intermediate phalanx of a finger, respectively. In an example, there can be three rings, one each on the distal phalanx, the intermediate phalanx, and the proximal phalanx of a finger.

In an example, a finger ring can further comprise one or more components selected from the group consisting of: power source; energy transducer; data processing unit; wireless data transmitter; wireless data receiver; computer-to-human interface; microphone; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger rings are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger rings are in wireless communication with a handheld computing device. A handhand computing device can be selected from the group consisting of: smart phone or other mobile phone; electronic pad or tablet, and other portable computer.

In an example, electromagnetic energy from electromagnetic energy emitter 6003 which is measured by electromagnetic energy sensor 6004 can be analyzed in order to estimate the bending motion of a distal interphalangeal joint, a proximal interphalangeal joint, and/or a meta-carpophalageal joint. In an example, data from multiple electromagnetic energy sensors on multiple fingers can be received and analyzed by a data processing unit in order to recognize hand gestures. In an example, this data processing unit can be part of a finger ring. In an example, this data processing unit can be part of a separate wearable or handheld device with which finger rings are in wireless communication. Other relevant design variations discussed with respect to other examples in this description can also apply to the example shown here in FIG. 6.

Figure 7:
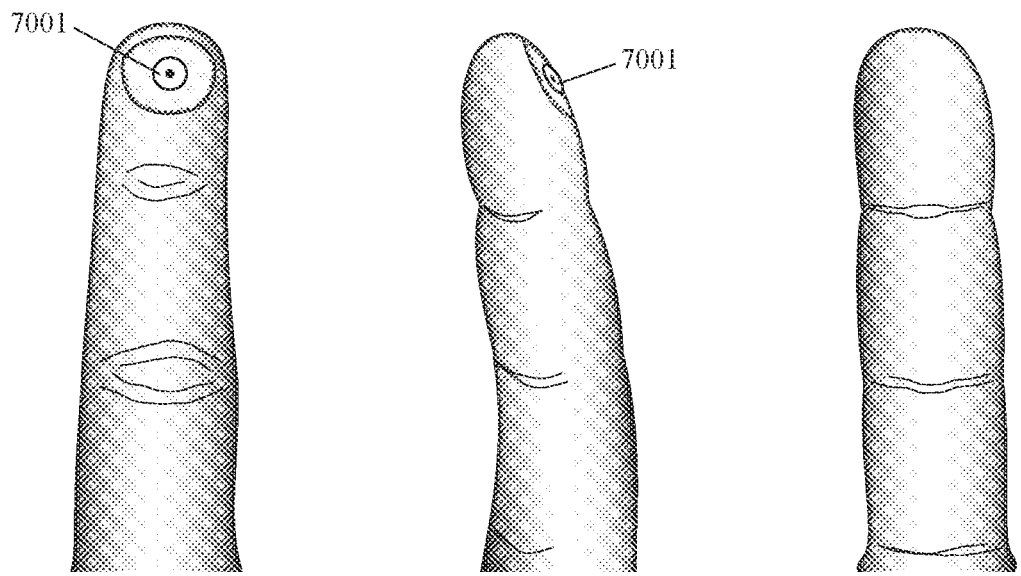
FIG. 7 shows an inertial motion sensor attached to a finger nail.

FIG. 7 shows another example of how this invention can be embodied in a wearable device for measuring finger motion and recognizing hand gestures. This device comprises an inertial motion sensor 7001 which is attached to a finger nail. The left third of FIG. 7 shows this device from a top-down perspective, looking at the upper (dorsal) surface of a person's finger. The middle third of FIG. 7 shows this same device from a side perspective, with the finger having been rotated 90 degrees clockwise. The right third of FIG. 7 shows this same device from a bottom-up perspective, looking at the lower (ventral) surface of the finger.

In an example, inertial motion sensor 7001 can be attached to a finger nail by adhesion. In an example, inertial motion sensor 7001 can be integrated into a sticker. In an example, a layer can be removed from a sticker to expose an adhesive side which then is pressed against a finger nail in order to attach the sensor to the finger nail. In an example, inertial motion sensor 7001 can be adhered to a finger nail using glue. In an example, an inertial motion sensor can be integrated into an artificial finger nail which is then adhered to a natural finger nail. In an example, an inertial motion sensor can be selected from the group consisting of: accelerometer, gyroscope, and inclinometer. In an example, there can be multiple inertial motion sensors and/or different types of inertial motion sensors attached to the same finger nail.

In an example, the motion of an inertial motion sensor which is attached to a finger nail can be analyzed in order to estimate the bending motion of a proximal interphalangeal joint, a distal interphalangeal joint, and/or a meta-carpophalageal joint. When there is only one motion measurement location on a finger, a single sensor on a distal phalanx (as in this device) can provide more accurate estimation of the movement of the entire finger than is possible with a single sensor on a proximal phalanx (as with a conventionally-located finger ring). Even though there is only one motion measurement location on a finger (i.e. on the finger nail), knowledge of joint biomechanics can be used to extrapolate the most-likely angles of all three finger joints and the most-likely positions of all three finger bones.

In an example, differences in the motion of an inertial motion sensor on a first finger versus the motion of an inertial motion sensor on a second finger can be analyzed in order to estimate the bending motion of interphalangeal and meta-carpophalageal joints. In an example, similarities in the motions of an inertial motion sensor on a first finger and an inertial motion sensor on a second finger can be analyzed in order to estimate the overall motion of (the centroid of) a person's hand. In an example, data from inertial motion sensors on multiple fingers can be received and analyzed by a data processing unit in order to recognize hand gestures.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, this device can further comprise one or more additional components which are also attached to a finger nail and/or in electronic communication with the inertial motion sensor. These additional components can be selected from the group consisting of: power source; energy transducer; data processing unit; wireless data transmitter; wireless data receiver; computer-to-human interface; microphone; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 7.

In various examples, this wearable device or a system comprising multiple such wearable devices can recognize one or more hand gestures selected from the group consisting of: "finger tap" (palm facing down with index tip moving down and up once); "finger double tap" (palm facing down with index tip moving down and up twice quickly); "finger press" (palm facing down with index tip pressing down for extended time); "finger slide right" (palm facing down with index or middle tip moving right and arcing left); "finger slide left" (palm facing down with index or middle tip moving left and arcing right); "finger rub" (palm facing down with index or middle tip moving back and forth); "finger scroll down" (palm facing down with index or middle tip moving down and arcing up); "finger scroll up" (palm facing down with index or middle tip moving up and arcing down); "finger clockwise" (index or middle tip moving in a clockwise circle or arc of a circle); "finger counter-clockwise" (index or middle tip moving in a counter-clockwise circle or arc of a circle); "finger figure eight" (index or middle tip moving in a figure eight); "finger pinch" (thumb and index or middle tip moving closer); "finger spread" (thumb and index or middle tip moving apart); "finger merge" (index tips from both hands moving together); "finger divide" (index tips from both hands moving apart); "grasp" (thumb and aligned fingers touch to form a "C"); "drink" (thumb and aligned fingers form a "C" and hand rotating toward person); "grab" (thumb and four fingers contracting simultaneously); "move down" (palm facing down with hand pivoting downward from wrist and/or elbow); "move up" (palm facing up with hand pivoting upward from wrist and/or elbow); "move right" (palm facing sideways with hand pivoting rightward from wrist); "move left" (palm facing sideways with hand pivoting leftward from wrist); "hand rotation clockwise" (flat hand rotating clockwise); "hand rotation counter-clockwise" (flat hand rotating counter-clockwise); "hold and turn clockwise" (first with thumb and index extended and rotating clockwise); "hold and turn counter-clockwise" (first with thumb and index extended and rotating counter-clockwise); "outward palm" (flat hand with palm outward and thumb and all fingers extended); "hand wave" (flat hand with palm outward and side-to-side motion); "chop" (flat hand with palm downward and side-to-side motion); "fist" (thumb and all fingers contracted); "fist pump" (upright first moving up and down); "fist bang or first bump" (extended first moving down and up); "knock" (first pivoting downward from wrist); "thumbs down" (first with thumb extended downwards); "thumbs up" (first with thumb extended upward); "point" (first with index tip extended outward); "gun" (vertical first with index and middle extended outward together); "V" or "peace sign" (outward-facing first with index and middle extended upwards apart); "scissors" (first with index and middle apart and then together); "Vulcan salute" (outward-facing palm with fingers up and separated between middle and ring); "cuckold/horns" (hand vertical with index and pithy upward); "middle finger" (upward first with middle extended upward); "call me" (vertical first with thumb and pinky extended); "hang loose" (horizontal palm with thumb and pinky extended); "I Love You" (thumb, index, and pinky extended while middle and ring touch palm); "OK" (thumb and index form a circle); "loser" (first with thumb and index finger extended at a right angle); "no" (first with raised extended index moving side to side); "finger cross" (thumb and middle fingers crossed); "finger snap" (middle sliding quickly from tip to base of thumb); "money" (tips of middle and thumb rubbing back and forth on each other); "come here" (upward or sideways facing first with index tip extended and moving inward); "blah blah" (thumb and horizontal extended fingers opening and closing together); "I think you are a troll" (index of one hand touching palm of other hand); "world's smallest violin" (first with thumb and index extended and rubbing); "writing" (first with thumb and index touching and moving together); "thumb to index" (thumb tip touching index finger tip); "thumb to middle" (thumb tip touching middle finger tip); "thumb to ring" (thumb tip touching ring finger tip); "thumb to pinky" (thumb tip touching pinky tip); a gesture indicating a selected letter in sign language; and a gesture indicating a selected word in sign language.

Figure 8:
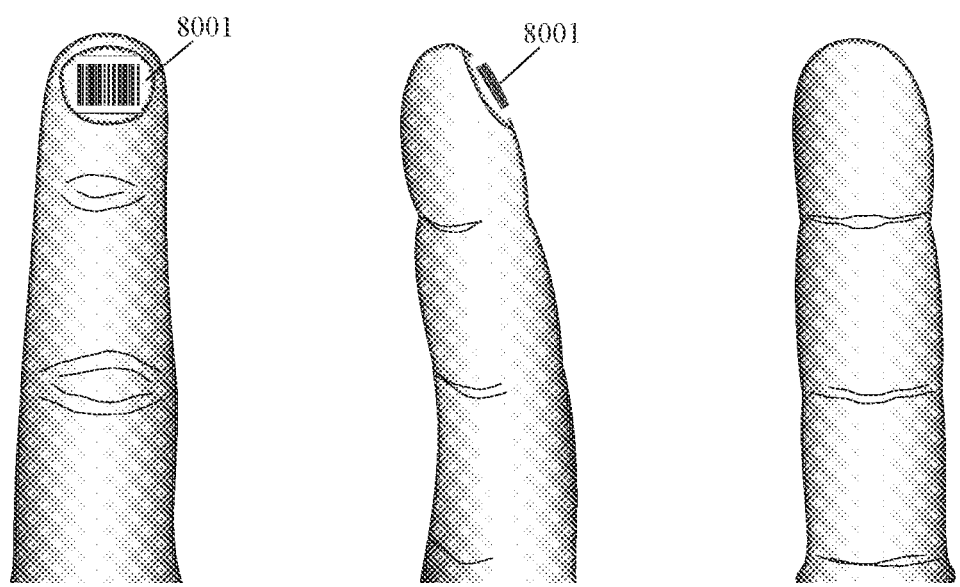
FIG. 8 shows a machine-readable optical pattern attached to a finger nail.

FIG. 8 shows another example of how this invention can be embodied in a wearable device for measuring finger motion and recognizing hand gestures. This device comprises a light-energy reflector and/or machine-readable optical pattern 8001 which is attached to a finger nail. The left third of FIG. 8 shows this device from a top-down perspective, looking at the upper (dorsal) surface of a person's finger. The middle third of FIG. 8 shows this same device from a side perspective, with the finger having been rotated 90 degrees clockwise. The right third of FIG. 8 shows this same device from a bottom-up perspective, looking at the lower (ventral) surface of the finger.

In an example, a light-energy reflector and/or machine-readable optical pattern can be attached to a finger nail by adhesion. In an example a light-energy reflector and/or machine-readable optical pattern can be integrated into a sticker. In an example, a layer can be removed from a sticker to expose an adhesive side which is pressed against a finger nail in order to attach a light-energy reflector and/or machine-readable optical pattern to the finger nail. In an example, a light-energy reflector and/or machine-readable optical pattern can be adhered to a finger nail using glue. In an example, a light-energy reflector and/or machine-readable optical pattern can be integrated into an artificial finger nail which is then adhered to a natural finger nail. In an example, a light-energy reflector and/or machine-readable optical pattern can be a bar code or QR code.

In an example, a light-energy reflector can have a surface which reflects light energy hitting it from an external source. In an example, an external light source can be an environmental light source (such as the sun) or an artificial light in the environment. In an example, an external light source can be part of a separate wearable device. In an example, a light source can be an infrared or near-infrared light source. In an example, a light source can be a polarized or coherent light source.

In an example, a light-energy reflector can have a unique reflective color, wavelength, spectrum, polarization, light pattern, and/or shape which enables it to be differentiated from other light-energy reflectors. In an example, this device can be part of a system for measuring finger motion and recognizing gestures which further comprises a camera to track the locations of light-energy reflectors worn on the fingers. In an example, this camera can be incorporated into smart glasses or other electronically-functional eyewear, an EEG monitor, a hat, cap, or visor, a smart necklace, a wearable button, and/or an upper body garment. In an example, analysis of images captured by a camera can identify and track light-energy reflectors based on their unique reflective colors, wavelengths, spectrums, polarizations, light patterns, and/or shapes.

The device shown in FIG. 8 can be part of a system for measuring finger motion and recognizing hand gestures comprising: a plurality of light-energy reflectors and/or machine-readable optical patterns which are attached to a person's finger nails; electronically-functional eyewear; and a camera which is part of the eyewear, wherein analysis of images captured by the camera is used to identify the locations of the light-energy reflectors and/or machine-readable optical patterns to recognize hand gestures. In an example, each light-energy reflector can have a unique color, wavelength, spectrum, polarization, pattern, or shape. In an example, each machine-readable optical pattern can be unique. In an example, this system can function as a gesture-based human-to-computer interface.

In an example, the motion of a light-energy reflector and/or machine-readable optical pattern which is attached to a finger nail can be analyzed in order to estimate the bending motion of a proximal interphalangeal joint, a distal interphalangeal joint, and/or a meta-carpophalageal joint. When there is only one motion measurement location on a finger, a single reflector on a distal phalanx (as in this device) can provide more accurate estimation of the movement of the entire finger than is possible with a single reflector on a proximal phalanx (as with a conventionally-located finger ring). Even though there is only one motion measurement location on a finger (i.e. on the finger nail), knowledge of joint biomechanics can be used to extrapolate the most-likely angles of all three finger joints and the most-likely positions of all three finger bones.

In an example, differences in the motion of a light-energy reflector and/or machine-readable optical pattern on a first finger versus the motion of a light-energy reflector and/or machine-readable optical pattern on a second finger can be analyzed in order to estimate the bending motion of interphalangeal and meta-carpophalageal joints. In an example, similarities in the motions of a light-energy reflector and/or machine-readable optical pattern on a first finger and a light-energy reflector and/or machine-readable optical pattern on a second finger can be analyzed in order to estimate the overall motion of (the centroid of) a person's hand. In an example, data from light-energy reflectors and/or machine-readable optical patterns on multiple fingers can be received and analyzed by a data processing unit in order to recognize hand gestures.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, this device can further comprise one or more additional components which are also attached to a finger nail and/or in electronic communication with the light-energy reflector and/or machine-readable optical pattern. These additional components can be selected from the group consisting of: power source; energy transducer; data processing unit; wireless data transmitter; wireless data receiver; computer-to-human interface; microphone; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 8.

Figure 9:
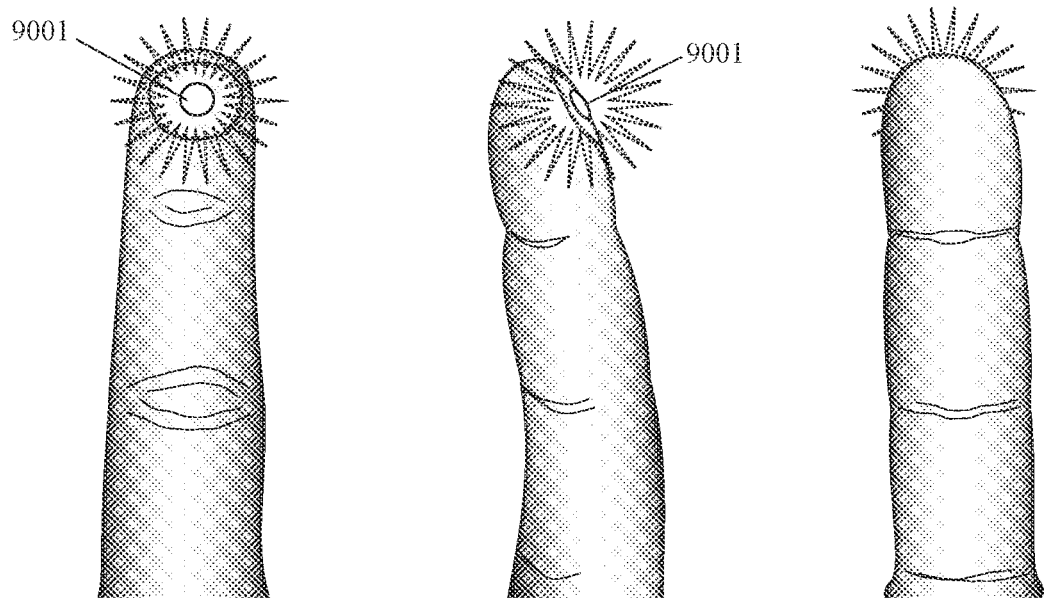
FIG. 9 shows a diffuse light energy emitter attached to a finger nail.

FIG. 9 shows another example of how this invention can be embodied in a wearable device for measuring finger motion and recognizing hand gestures. This example is similar to the example shown in FIG. 8 except that an active light-energy emitter (such as an LED) 9001 is attached to a finger nail. The left third of FIG. 9 shows this device from a top-down perspective, looking at the upper (dorsal) surface of a person's finger. The middle third of FIG. 9 shows this same device from a side perspective, with the finger having been rotated 90 degrees clockwise. The right third of FIG. 9 shows this same device from a bottom-up perspective, looking at the lower (ventral) surface of the finger.

In an example, an active light-energy emitter (such as an LED) which is attached to a finger nail can be tracked by a wearable camera in order measure finger motion and recognize hand gestures. In an example, a wearable camera can be part of smart glasses or other electronically-functional eyewear. In an example, a specific light-energy emitter can emit light with a unique color, wavelength, polarization, or pattern which enables it to be differentiated from other light-energy emitters in a finger-worn device or a system of finger-worn devices. Other relevant design variations discussed with respect to other examples in this description can also apply to the example shown here in FIG. 9.

Figure 10:
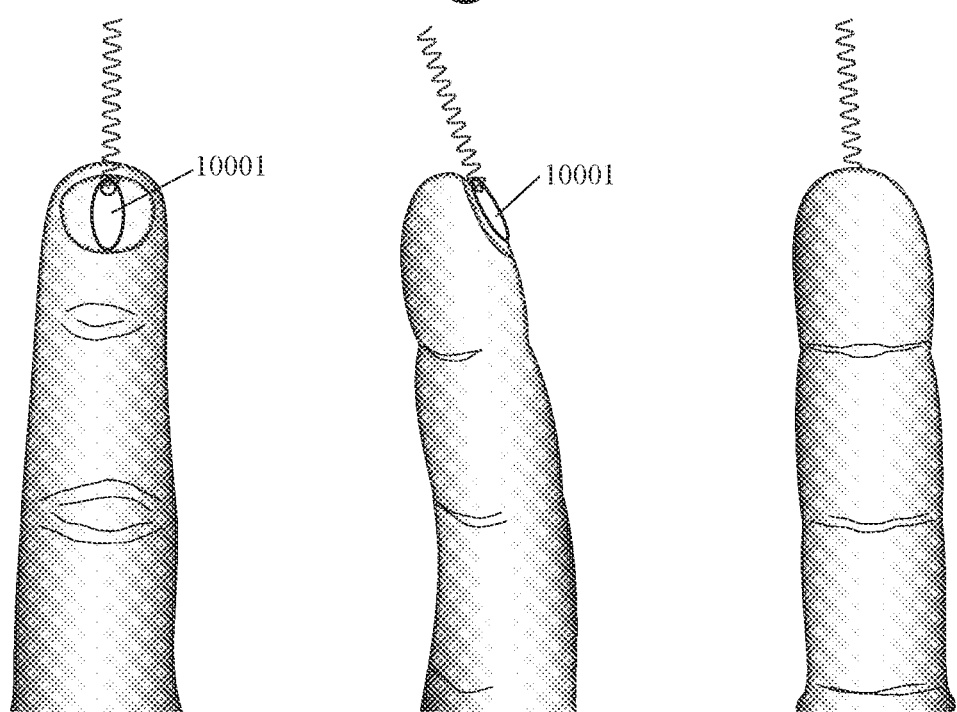
FIG. 10 shows a focused light energy emitter attached to a finger nail.

FIG. 10 shows another example of how this invention can be embodied in a wearable device for measuring finger motion and recognizing hand gestures. This example is similar to the example shown in FIG. 9 except that light-energy emitter 10001 emits a focused beam of light outward from a finger nail. In an example, this focused beam of light has an emission vector which is generally parallel to the longitudinal axis of the distal phalanx so that the beam of light is directed where the finger "points". In an example, the beam of light can be a beam of coherent light. In an example, light-energy emitter 10001 can be a laser.

In an example, a wearable camera can track movement of a beam of light by tracking its place of emission on a finger nail. In an alternative example, a wearable camera can track movement of a beam of light by tracking its focal and/or reflective destination. In an example, movement of this beam of light can be used to measure finger motion and recognize hand gestures. In an example, movement of the focal and/or reflective destinations of multiple beams of light on an environmental surface can be analyzed to infer movements of the finger tips (and fingers). In an example, such a system can turn any (flat) environmental surface into a virtual touch screen. Such a system can also give new meaning to the phrase "point and click." Other relevant design variations discussed with respect to other examples in this description can also apply to the example shown here in FIG. 10.

Figure 11:
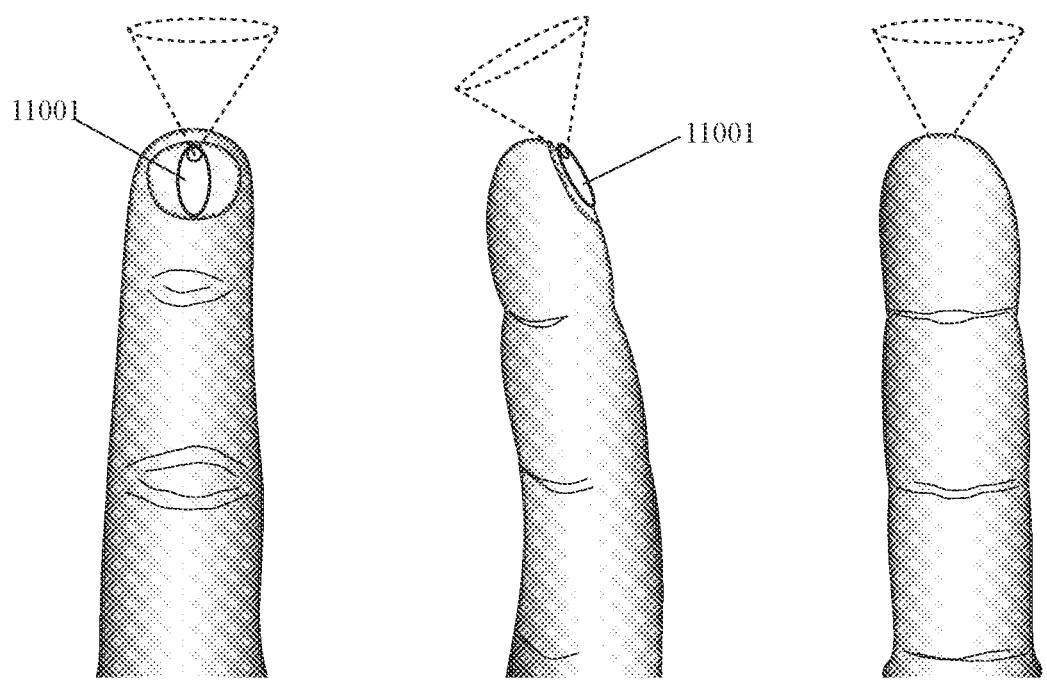
FIG. 11 shows a camera attached to a finger nail.

FIG. 11 shows another example of how this invention can be embodied in a wearable device for measuring finger motion and recognizing hand gestures. This device comprises a small camera 11001 which is attached to a finger nail. The left third of FIG. 11 shows this device from a top-down perspective, looking at the upper (dorsal) surface of a person's finger. The middle third of FIG. 11 shows this same device from a side perspective, with the finger having been rotated 90 degrees clockwise. The right third of FIG. 11 shows this same device from a bottom-up perspective, looking at the lower (ventral) surface of the finger.

In an example, a camera can be attached to a finger nail by adhesion. In an example, a camera can be integrated into a sticker; a layer can be removed from the sticker to expose an adhesive side which is pressed against a finger nail in order to attach the camera to the finger nail. In an example, a camera can be adhered to a finger nail using glue. In an example, a camera can be integrated into an artificial finger nail which is then adhered to a natural finger nail.

In an example, the focal direction of a camera attached to a finger nail can be outwards and generally parallel to the longitudinal axis of the distal phalanx or to the linear approximation of the longitudinal axis of the combined three phalanges of the finger. In an example, the focal direction of a camera can be oriented toward an object at which a person points their finger. In an example, movement of a finger can be estimated by analyzing the apparent relative motion of environmental objects in images captured by a camera attached to a finger nail. For example, if an environmental object which is assumed to be stationary appears to move upwards, then the finger is probably moving downwards. For example, if an environmental object which is assumed to be stationary appears to move to the right, then the finger is probably moving to the left.

Assumptions concerning whether an environmental object is actually stationary or not can be made more accurately using a plurality of cameras attached to different finger nails. In a system with a plurality of cameras attached to different finger nails, the apparent motion of environmental objects can be compared across images captured by different cameras. For example, if an environmental object appears to be moving to the left in images from a camera on a first finger and the same environmental object appears to be moving to the right in images from a camera on a second finger, then the two fingers are probably moving relative to each other. In an example, hand gestures can be recognized by analyzing the relative movements of environmental objects in images captured by cameras on different fingers.

In an example, the relative configurations of different fingers can be modeled by identifying commonalities in images captured by cameras on different fingers. For example, if the same object appears in images captured by first and second cameras on first and second fingers, but in different locations within the cameras' fields of vision, then the relative angles and/or configurations of the first and second fingers can be estimated. In an example, hand gestures can be recognized by analyzing the relative locations of environmental objects which appear in images captured by two or more cameras on two or more different fingers.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, this device can further comprise one or more additional components which are also attached to a finger nail and/or in electronic communication with the camera. These additional components can be selected from the group consisting of: power source; energy transducer; data processing unit; wireless data transmitter; wireless data receiver; computer-to-human interface; microphone; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet; and other portable computer. Other relevant design variations discussed with respect to other examples in this description can also apply to the example shown here in FIG. 11.

In an example, such a hardware configuration (e.g. having one or more cameras attached to finger nails) can also be used as "real world mouse" to direct a computer's focus to a particular location in the real world in a manner which is analogous to how a traditional "computer mouse" directs a computer's focus to a particular location (e.g. a cursor) on a computer screen. For example, a person with a finger nail camera can move their finger along a printed page in order to focus a selected computer function on a selected location on that page. For example, this function may comprise reading a text character or identifying an object in a photo at the selected location on that printed page.

In this manner, a "real world mouse" can operate on a text character, photo, or other object on a real world (non-electronic) surface in the same way that a "computer mouse" operates on text character, photo, or other object on a computer (electronic) screen. For example, one can imagine such a device being applied in the following sequence—a person with a finger nail camera points at an object on a printed page and asks "What is this?", a voice recognition function understands the request, the computer analyzes the object within the camera's field of vision, and then the computer says the answer. A similar sequence could help to translate words on a particular portion of a printed page (such as menu in a foreign language) or help vision-impaired people to read a particular portion of a printed page.

Figure 12:
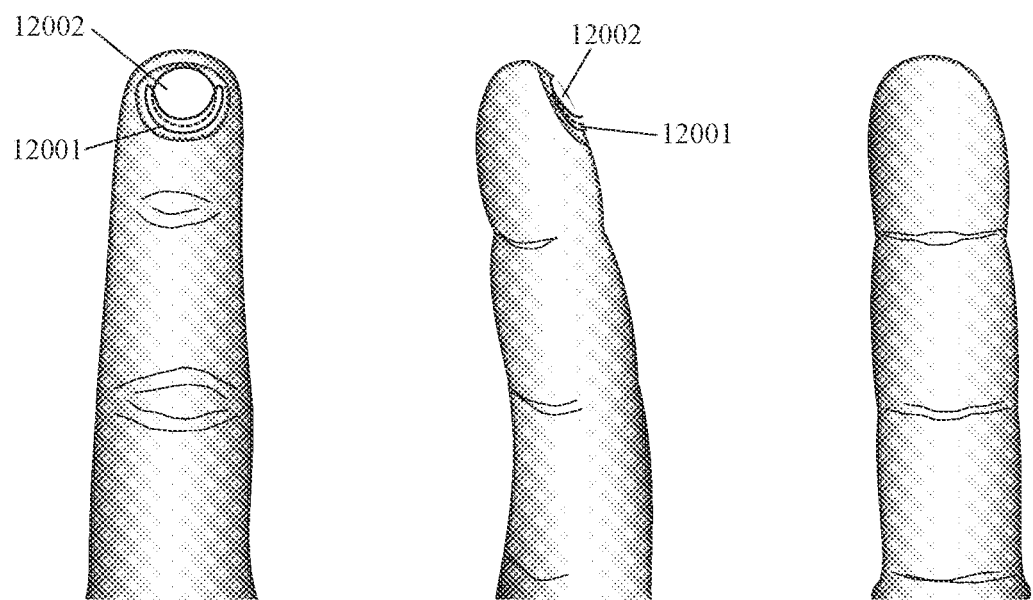
FIG. 12 shows a sensor removably attached to a finger nail by a distal-facing semi-circular base.

FIG. 12 shows a specific type of mechanism for attaching a device (such as one of those shown in FIGS. 7-11) to a finger nail. The left third of FIG. 12 shows this mechanism from a top-down perspective, looking at the upper (dorsal) surface of a person's finger. The middle third of FIG. 12 shows this same mechanism from a side perspective, with the finger having been rotated 90 degrees clockwise. The right third of FIG. 12 shows this same mechanism from a bottom-up perspective, looking at the lower (ventral) surface of the finger.

Although a device such as one of those shown in FIGS. 7-11 can be attached to a finger nail by adhesion, attachment by adhesion does not allow easy removal and reattachment of the device. The adhered device is not very modular. It would be desirable to have an attachment mechanism which allows a person to easily attach, remove, and then reattach a device which is worn on a finger nail. This would enable a device on the finger nail to be modular so that a person can easily remove, switch, and reconfigure one or more finger-nail-worn devices. This would enable a person to easily attach and remove a finger-nail-worn device for washing their hands, going swimming, or any other reason. To address this need, the example shown in FIG. 12 shows a specific type of mechanism for easy attachment, removal, and reattachment of a device worn on a finger nail.

Specifically, the example shown in FIG. 12 comprises: an arcuate member 12001, wherein this arcuate member has a first surface which is attached to a finger nail, wherein this arcuate member has a second surface which faces away from the finger nail, and wherein this arcuate member has an arcuate groove between the first surface and the second surface; and a motion sensor (or housing thereof) 12002, wherein a proximal portion of this motion sensor (or housing thereof) is removably inserted into the arcuate groove of the arcuate member in order to hold the motion sensor on the finger nail. In an example, the first surface of the arcuate member can be attached to the finger nail by adhesion. In an example, the arcuate member can be part of an artificial finger nail which is attached to the natural finger nail by adhesion.

In an example, an arcuate member and/or an arcuate groove can have a shape which is selected from the group consisting of: smile, horseshoe, semi-circle, half of an ellipse, half of an oval, arcuate segment of a circle, arcuate segment of an ellipse, and arcuate segment of an oval. In an example, an arcuate member and/or an arcuate groove can be curved with a focal direction which is substantially parallel to the longitudinal axis of the distal phalanx and which points outward from the finger tip. In an example: a first surface of an arcuate member can have a shape which is selected from the group consisting of circle, ellipse, and oval; and a second surface of an arcuate member can have a shape which is selected from the group consisting of segment of a circle, segment of an ellipse, and segment of an oval.

In an example, a motion sensor (or housing thereof) can have a proximal portion with a shape which is selected from the group consisting of: smile, horseshoe, semi-circle, half of an ellipse, half of an oval, arcuate segment of a circle, arcuate segment of an ellipse, and arcuate segment of an oval. In an example, the shape of the proximal portion of a motion sensor (or housing thereof) can geometrically complement and/or fit into the shape of the arcuate groove. In an example, the proximal portion of a motion sensor can fit into the arcuate groove in a "tongue and groove" manner. In an example, there can also be a ridge or other protrusion within the groove which enables the proximal portion of the motion sensor (or housing thereof) to click, clip, or snap into (or out of) the groove—so that it is less-likely to slip out unintentionally. In an example, a groove can have a forward-facing (distal) orientation. In an example, a groove can have a backward-facing (proximal) orientation. In an example, the back of a groove can be stellar. In an example, Stella can get her groove back.

In an example, the proximal portion of a motion sensor (or housing thereof) can slide laterally in a proximal direction into the arcuate groove in order to hold the motion sensor (or housing thereof) onto the finger nail. In an example, the proximal portion of the motion sensor (or housing thereof) can slide laterally in a distal direction out of the arcuate groove in order to remove the motion sensor (or housing thereof) from the finger nail. In an example, the motion sensor (or housing thereof) can be modular.

In an example, the cross-sectional area of an arcuate member (including the area enclosed within its curvature) can be configured to span between 50-95% of the upper surface of a finger nail. In an example, the cross-sectional area of a motion sensor (or housing thereof) can be configured to span between 50-95% of the upper surface of a finger nail. In an example, the width of an arcuate member can be configured to span between 50-95% of the width of a finger nail. In an example, the width of a motion sensor (or housing thereof) can be less than 95% of the width of the arcuate member. In an example, neither the arcuate member nor the motion sensor (or housing thereof) may extend outside the perimeter of the finger nail when the motion sensor (or housing thereof) is inserted into the arcuate groove.

In an example, there can be an upper surface of a motion sensor (or housing thereof) which faces away from a finger nail. In an example, an upper surface of a motion sensor (or housing thereof) can overlap the second surface of an arcuate member when the motion sensor (or housing thereof) is inserted into an arcuate groove. In an example, the upper surface of the motion sensor (or housing thereof) can overlap between 20-80% of the second surface of an arcuate member when the motion sensor (or housing thereof) is inserted into an arcuate groove.

In this example, a motion sensor (or housing thereof) can be removably attached to a finger nail by laterally sliding the component into an arcuate groove. In another example, a different electronic component can be removably attached to a finger nail by laterally sliding the component into an arcuate groove. In an example, a different electronic component can have a separate housing than a motion sensor. In an example, a different electronic component can share the same housing as a motion sensor and be jointly inserted into an arcuate groove.

In an example, a different electronic component can be selected from the group consisting of: power source; energy transducer; data processing unit; wireless data transmitter; wireless data receiver; computer-to-human interface; microphone; camera; and electromagnetic energy sensor. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, one or more such finger-worn devices can be part of a system wherein finger-worn devices are in wireless communication with a separate wearable device. In an example, multiple finger-worn devices can be in wireless communication with a separate, electronically-functional wrist band which functions as a wearable system hub. In an example, a separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 12.

Figure 13:
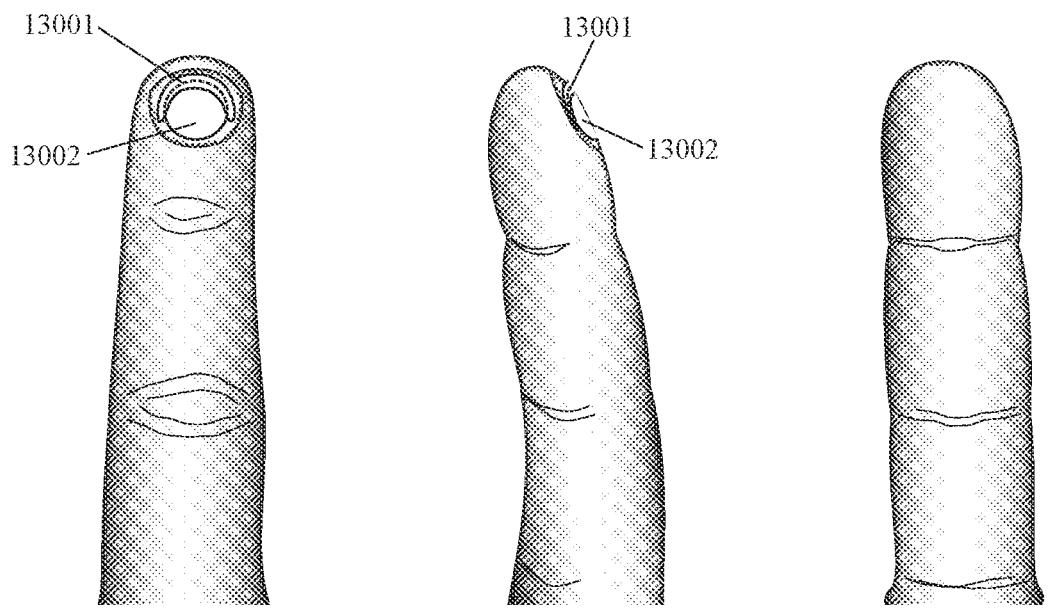
FIG. 13 shows a sensor removably attached to a finger nail by a proximal-facing semi-circular base.

FIG. 13 shows another mechanism for attaching a motion recognition device such as those shown in FIGS. 7-11 to a finger nail. The left third of FIG. 13 shows this mechanism from a top-down perspective, looking at the upper (dorsal) surface of a person's finger. The middle third of FIG. 13 shows this same mechanism from a side perspective, with the finger having been rotated 90 degrees clockwise. The right third of FIG. 13 shows this same mechanism from a bottom-up perspective, looking at the lower (ventral) surface of the finger.

The example shown in FIG. 13 comprises: an arcuate member 13001, wherein this arcuate member has a first surface which is attached to a finger nail, wherein this arcuate member has a second surface which faces away from the finger nail, and wherein this arcuate member has an arcuate groove between the first surface and the second surface; and a motion sensor (or housing thereof) 13002, wherein a proximal portion of this motion sensor (or housing thereof) is removably inserted into the arcuate groove of the arcuate member in order to hold the motion sensor on the finger nail. In an example, the first surface of the arcuate member can be attached to the finger nail by adhesion. In an example, the arcuate member can be part of an artificial finger nail which is attached to the natural finger nail by adhesion.

The example shown in FIG. 13 is like the one that was shown in FIG. 12, except that the curvature of the device focuses in a proximal direction rather than a distal direction. Viewed from the person's perspective, the device in FIG. 13 looks like a frown on the finger nail rather than a smile on the finger nail. It may be slightly more difficult to slide a motion sensor into an arcuate member whose curvature focuses in a proximal direction, but the motion sensor may also be less likely to slip out during use. Other relevant design variations discussed with respect to other examples in this description can also apply to the example shown here in FIG. 13.

Figure 14:
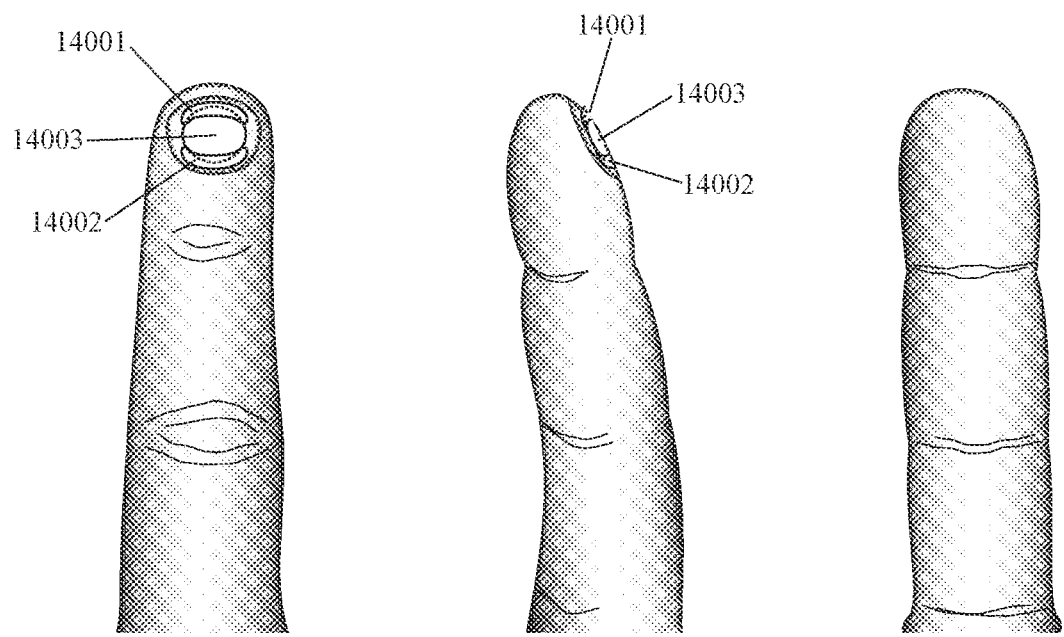
FIG. 14 shows a sensor removably attached to a finger nail by distal and proximal facing semi-circular bases.

FIG. 14 shows another mechanism for attaching a motion recognition device such as those shown in FIGS. 7-11 to a finger nail. The left third of FIG. 14 shows this mechanism from a top-down perspective, looking at the upper (dorsal) surface of a person's finger. The middle third of FIG. 14 shows this same mechanism from a side perspective, with the finger having been rotated 90 degrees clockwise. The right third of FIG. 14 shows this same mechanism from a bottom-up perspective, looking at the lower (ventral) surface of the finger.

The example shown in FIG. 14 comprises: (a) a first arcuate member 14001, wherein this first arcuate member has a lower surface which is attached to a finger nail, wherein this first arcuate member has an upper surface which faces away from the finger nail, wherein this first arcuate member has a first arcuate groove between the lower surface and the upper surface, and wherein this first arcuate member has a curvature which focuses in a proximal direction; (b) a second arcuate member 14002, wherein this second arcuate member has a lower surface which is attached to a finger nail, wherein this second arcuate member has an upper surface which faces away from the finger nail, wherein this second arcuate member has a second arcuate groove between the lower surface and the upper surface, and wherein this second arcuate member has a curvature which focuses in a distal direction; and (c) a motion sensor (or housing thereof) 14003, wherein a distal portion of this motion sensor (or housing thereof) is removably inserted into the first arcuate groove in order to hold the motion sensor on the finger nail, and wherein a proximal portion of this motion sensor (or housing thereof) is removably inserted into the second arcuate groove in order to hold the motion sensor on the finger nail.

In an example, the first and second arcuate members can be attached to the finger nail by adhesion. In an example, the first and second arcuate members can be part of an artificial finger nail which is attached to a natural finger nail by adhesion. In an example, a motion sensor (or housing thereof) can be inserted into the first and second arcuate grooves by a lateral sliding motion. In an example, a motion sensor (or housing thereof) can be first inserted into the first arcuate groove and then inserted into the second arcuate groove. In an example, a motion sensor (or housing thereof) can be flexible so that it can be bent while being inserted into the first and second arcuate grooves. In an example, the first and second arcuate members can be used to hold one or more other types of (modular) electronic components on a finger nail. Other relevant design variations discussed with respect to other examples in this description can also apply to the example shown here in FIG. 14.

Figure 15:
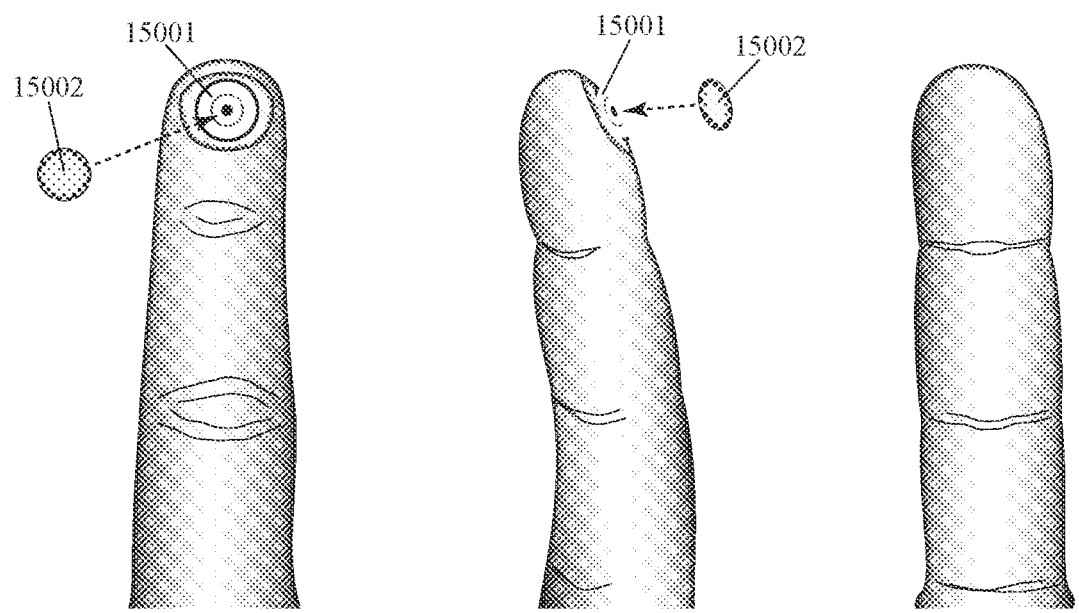
FIG. 15 shows a sensor removably attached to a finger nail by a snap.

FIG. 15 shows another type of mechanism for attaching a motion recognition device such as those shown in FIGS. 7-11 to a finger nail. The left third of FIG. 15 shows this mechanism from a top-down perspective, looking at the upper (dorsal) surface of a person's finger. The middle third of FIG. 15 shows this same mechanism from a side perspective, with the finger having been rotated 90 degrees clockwise. The right third of FIG. 15 shows this same mechanism from a bottom-up perspective, looking at the lower (ventral) surface of the finger.

The example shown in FIG. 15 comprises: (a) a base snap member 15001, wherein this base snap member has a lower surface which is configured to be attached to a finger nail, and wherein this base snap member has an upper surface with a first part of a snap connection; (b) a motion sensor (or housing thereof) 15002, wherein this motion sensor (or housing thereof) has a lower surface with a second part of a snap connection, and wherein the first and second parts of the snap connection can be removably attached to each other by frictional engagement (e.g. being snapped together).

In an example, the base snap member can be attached to the finger nail by adhesion. In an example, the base snap member can be part of an artificial finger nail which is attached to a natural finger nail by adhesion. In an example, the base snap member can have a shape selected from the group consisting of: circle, ellipse, oval, square, rounded square, rectangle, rounded rectangle, trapezoid, rounded trapezoid, hexagon, and egg shape. In an example, the first part of the snap connection can be a circular indentation and the second part of the snap connection can be a circular protrusion, or vice versa. In an alternative example, a base member on a finger nail and a motion sensor can be removably attached by a clip or a clasp mechanism. In an alternative example, a base member on a finger nail and a motion sensor can be removably attached by a mechanism selected from the group consisting of: hook-and-eye, buckle, clip, prong, clasp, hook, pin, button, plug, protrusion-and-eye, snap, zipper, and magnet. In an example, the first and second arcuate members can be used to hold one or more other types of (modular) electronic components on a finger nail. Other relevant design variations discussed with respect to other examples in this description can also apply to the example shown here in FIG. 15.

Figure 16:
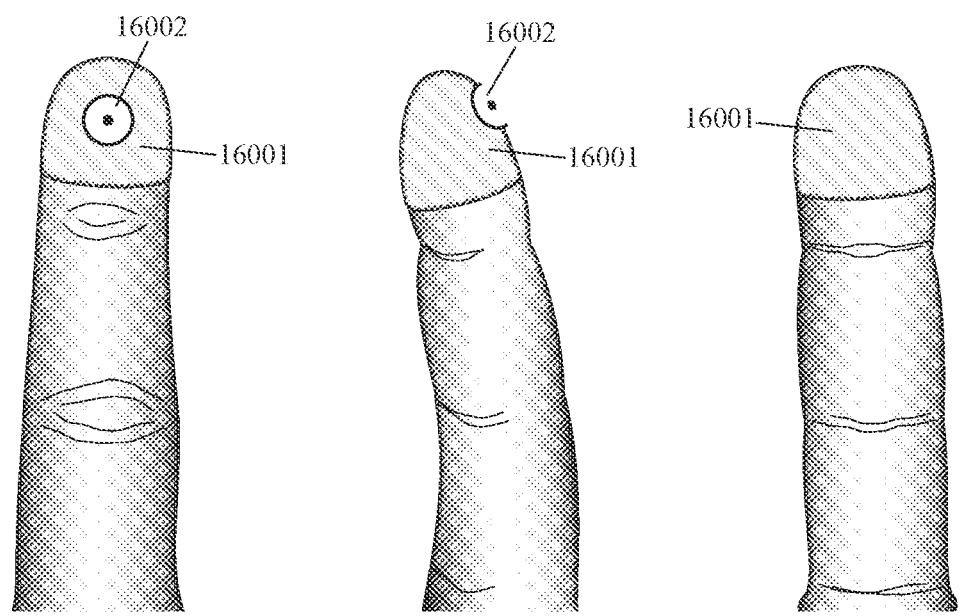
FIG. 16 shows a sensor removably attached to a finger by a finger-tip cover and/or thimble.

FIG. 16 shows another example of how this invention can be embodied in a wearable device for measuring finger motion and recognizing hand gestures. This device has a finger tip cover which slides over the end of a person's finger (in a manner similar to a thimble) and includes an inertial motion sensor. Specifically, FIG. 16 shows a wearable device for measuring finger motion and recognizing hand gestures comprising: finger tip cover 16001, wherein this cover is configured to fit on the tip of the finger; and inertial motion sensor 16002, wherein this inertial motion sensor is part of, or attached to, the finger tip cover. This device can also double as a great finger puppet for a one-eyed minion from the movie "Despicable Me." The left third of FIG. 16 shows this device from a top-down perspective, looking at the upper (dorsal) surface of a person's finger. The middle third of FIG. 16 shows this same device from a side perspective, with the finger having been rotated 90 degrees clockwise. The right third of FIG. 16 shows this same device from a bottom-up perspective, looking at the lower (ventral) surface of the finger.

In an example, a finger tip cover can be made with a stretchable and/or elastic material. In an example, a finger tip cover can be stretched to slide onto the end of a person's finger, but can also contract to frictionally grip the finger tip once it is on the finger tip. In an example, a finger tip cover can made from an elastic and/or stretchable fabric like elastane or spandex. In an example, a finger tip cover can cover the sides and the end of a finger like a thimble. In an example a finger tip cover can be relatively rigid (made out of metal or plastic) like an actual thimble. In an example, a finger tip cover can have a shape like a rounded cone, a half ellipsoid, or a half egg. In an alternative example, a finger tip cover can be shaped like a cylinder or torus and cover the sides of a finger tip, but not the very end. In an example, a finger tip cover can cover the finger nail. In an example, a finger tip cover spans the entire distal phalanx. In an example, a finger tip cover can cover the distal interphalangeal joint.

In an example, a finger tip cover can be held onto a finger tip by friction. In an example a finger tip cover can be held onto a finger tip by a mechanism selected from the group consisting of: hook-and-eye, buckle, clip, prong, clasp, hook, pin, button, plug, protrusion-and-eye, snap, zipper, and magnet. In an example, a finger tip cover can be held onto a finger tip by adhesion. In an example, a finger tip cover can be held onto a finger tip by suction. In an example, a finger tip cover can be held onto a finger tip using a combination of a liquid or gelatinous substance and suction.

In an example, an inertial motion sensor can be selected from the group consisting of: accelerometer, gyroscope, and inclinometer. In an example, there can be multiple inertial motion sensors and/or different types of inertial motion sensors attached to the same finger tip cover. In an example, the motion of an inertial motion sensor which is attached to a finger tip can be analyzed in order to estimate the bending motion of a distal interphalangeal joint. In an example, the motion of an inertial motion sensor which is attached to a finger tip can be analyzed in order to estimate the bending motion of a distal interphalangeal joint, a proximal interphalangeal joint, and a meta-carpophalageal joint. Even though there is only one motion measurement location on a finger in this case (i.e. on the finger tip), knowledge of joint biomechanics can be used to extrapolate the most-likely angles of all three finger joints and the most-likely positions of all three finger bones.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, this device can further comprise one or more additional components which are also attached to a finger tip and/or in electronic communication with an inertial motion sensor. These additional components can be selected from the group consisting of: power source; energy transducer; data processing unit; wireless data transmitter; wireless data receiver; computer-to-human interface; microphone; pressure sensor; infrared light sensor; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 16.

Figure 17:
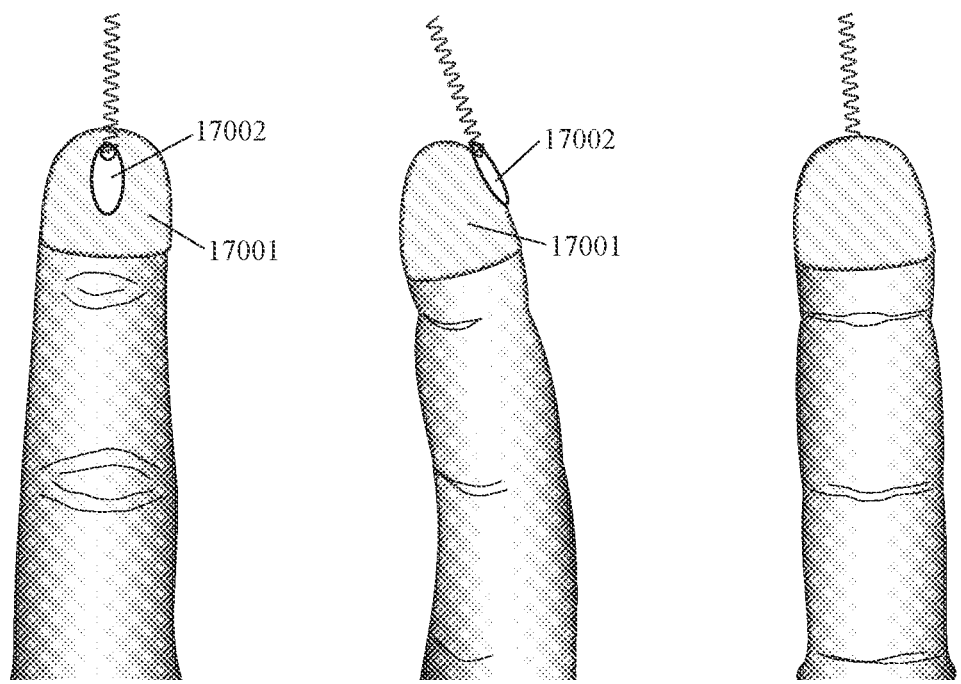
FIG. 17 shows a focused light emitter removably attached to a finger by a finger-tip cover and/or thimble.

FIG. 17 shows another example of how this invention can be embodied in a wearable device for measuring finger motion and recognizing hand gestures. This example is similar to the example shown in FIG. 16, except that the finger tip cover includes a light beam emitter which directs a focused beam of light outward from the finger tip. Specifically, FIG. 17 shows a wearable device for measuring finger motion and recognizing hand gestures comprising: finger tip cover 17001, wherein this finger tip cover is configured to fit on the tip of the finger; and focused light beam emitter 17002, wherein this focused beam emitter is part of, or attached to, the finger tip cover. The left third of FIG. 17 shows this device from a top-down perspective, looking at the upper (dorsal) surface of a person's finger. The middle third of FIG. 17 shows this same device from a side perspective, with the finger having been rotated 90 degrees clockwise. The right third of FIG. 17 shows this same device from a bottom-up perspective, looking at the lower (ventral) surface of the finger.

In an example, focused light beam emitter 17002 can be a Light Emitting Diode (LED). In an example, focused light beam emitter 17002 can be a laser. In an example, the focused beam of light which is emitted from light beam emitter 17002 can have an emission vector which is generally parallel to the longitudinal axis of the distal phalanx. In an example, the focused beam of light can be directed wherever the person points their finger. In an example, the focused beam of light can be a beam of coherent light. In an example, the focused beam of light can be a beam of infrared or near-infrared light.

In an example, this device can be part of a system which further comprises a camera which tracks the movement of one or more focused beams of light emitting from one or more finger tips. In an example, this device can further comprise a wearable camera which is part of, or attached to, a finger tip cover. In an example, this device can be part of a system including a wearable camera on a separate wearable device. In an example, a wearable camera can be part of, or attached to, a finger ring. In an example, a wearable camera can be part of, or attached to, a wrist band. In an example, a wearable camera can be part of, or attached to, electronically-functional eyewear. In an example, a wearable camera can be part of, or attached to, an electronically-functional necklace. In an example, a camera can be incorporated into a separate device which is selected from the group consisting of: ear ring, EEG monitor, finger ring, hat, cap, hearing aid, other electronically-functional earwear, shirt, other upper body garment, smart glasses, other electronically-functional eyewear, smart necklace, smart pendant, "below-average but has potential" pendant, smart visor, smart goggles, wearable button, lapel pin, and brooch.

In an example, a wearable camera can track the movement of a focused beam of light by tracking its place of emission from a finger tip. In an example, a wearable camera can track the movement of a focused beam of light by tracking its focal destination. In an example, its focal destination is the location of maximal reflection of light energy in the environment. Expressing this more colloquially, the focal destination of a focused beam of light is "where the beam hits" in the environment. In an example, the movements of one or more focused beams of light emitted from one or more finger tips can be used to measure finger motion and recognize hand gestures. In an example, movements of the focal destinations of multiple beams of light from multiple finger tips on an environmental surface can be analyzed in order to infer movements of those finger tips. In an example, such a system can turn any (flat) environmental surface into a virtual touch screen. Such a system can give new (and more literal) meaning to the phrase "point and click."

In an example, the relative movements of the focal destinations of two or more focused beams of light can be analyzed in order to interpret user commands with respect to environmental objects. In an example, the convergence of two or more focused beams of light onto an environmental object can be interpreted as selecting that object for action. In an example, the convergence of the two beams of light on an environmental object is can be interpreted as a "pinching" or "grasping" action. In an example, when a person moves their thumb and index finger, this moves two focused beams of light projected from the (thumb and) finger tips, and the convergence of the focal destinations of these two beams of light on an environmental object can be interpreted as selecting or grasping that object for further action. In an example, a user thus engaged can say in a deep, sinister voice—"I find your lack of faith disturbing."

In an example, once an object has been virtually selected or grasped by the two light beams, it can be virtually moved by the user by keeping the beams of light from the thumb and index finger in the same relative configuration, but moving their entire hand as a whole. In an example, even if the person does not have the ability to directly move the virtually-selected environmental object in the real world, a personal robot in the real world can have this ability. In an example, this action may be interpreted by the personal robot as a command with respect to that environmental object. For example, a personal robot can act on this command by physically moving the environmental object to a location identified by movement of the focused beams of light emitted from the person's finger tips. Other relevant design variations discussed with respect to other examples in this description can also apply to the example shown here in FIG. 17.

Figure 18:
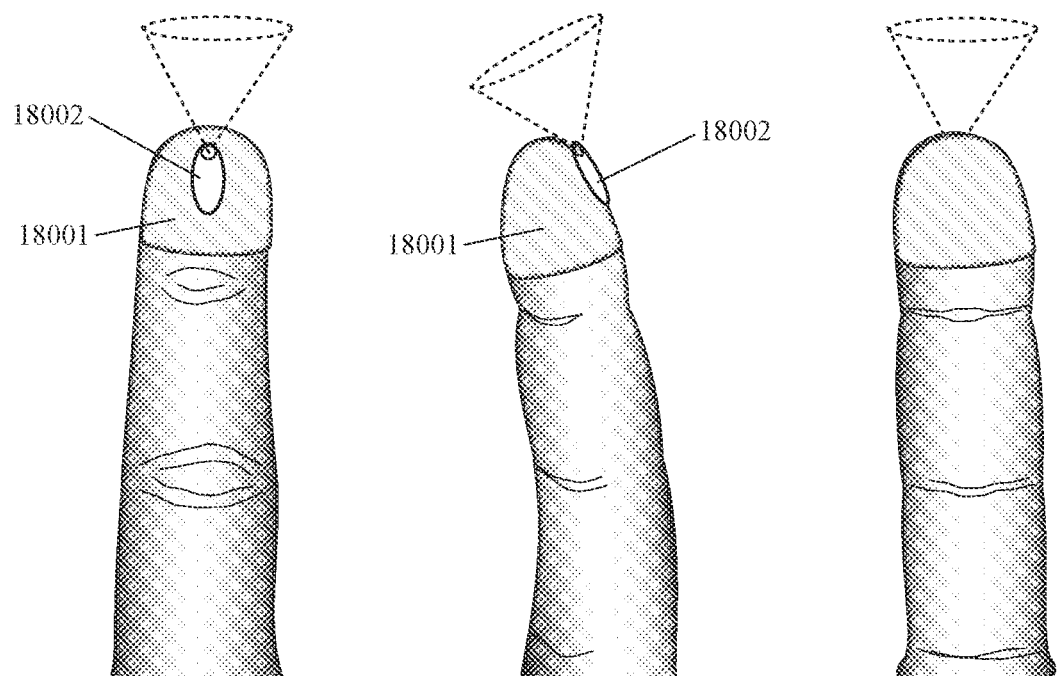
FIG. 18 shows a camera removably attached to a finger by a finger-tip cover and/or thimble.

FIG. 18 shows another example of how this invention can be embodied in a wearable device for measuring finger motion and recognizing hand gestures. This example is similar to the examples with finger tip covers that were shown in FIGS. 16 and 17, except that a finger tip cover now includes a small camera. Specifically, FIG. 18 shows a wearable device for measuring finger motion and recognizing hand gestures comprising: finger tip cover 18001, wherein this finger tip cover is configured to fit on the tip of the finger; and camera 18002, wherein this camera is part of, or attached to, the finger tip cover. The left third of FIG. 18 shows this device from a top-down perspective, looking at the upper (dorsal) surface of a person's finger. The middle third of FIG. 18 shows this same device from a side perspective, with the finger having been rotated 90 degrees clockwise. The right third of FIG. 18 shows this same device from a bottom-up perspective, looking at the lower (ventral) surface of the finger.

In an example, the focal direction of a camera attached to a finger tip cover can be outwards and generally parallel to the longitudinal axis of the distal phalanx or to the linear approximation of the longitudinal axis of the combined three phalanges of the finger. In an example, the focal direction of a camera can be directed wherever the person points their finger. In an example, the focal direction of a camera can be oriented toward an object at which a person points. In an example, movement of a finger can be estimated by analyzing the apparent relative motion of environmental objects in images captured by a camera attached to a finger tip cover. For example, if an environmental object which is assumed to be stationary appears to move upwards, then the finger is probably moving downwards. For example, if an environmental object which is assumed to be stationary appears to move to the right, then the finger is probably moving to the left.

Assumptions concerning whether an environmental object is actually stationary or not can be made more accurately using a plurality of cameras attached to different finger tip covers. In a system with a plurality of cameras attached to different finger tip covers, the apparent motion of environmental objects can be compared across images captured by different cameras. For example, if an environmental object appears to be moving to the left in images from a camera on a first finger and the same environmental object appears to be moving to the right in images from a camera on a second finger, then the two fingers are probably moving relative to each other. In an example, hand gestures can be recognized by analyzing the relative movements of environmental objects in images captured by cameras on different fingers.

In an example, the relative configurations of different fingers can be modeled by identifying commonalities in images captured by cameras on different fingers. For example, if the same object appears in images captured by first and second cameras on first and second fingers, but in different locations within the cameras' fields of vision, then the relative angles and/or configurations of the first and second fingers can be estimated. In an example, hand gestures can be recognized by analyzing the relative locations of environmental objects which appear in images captured by two or more cameras on two or more different fingers.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, this device can further comprise one or more additional components which are also attached to a finger tip cover and/or in electronic communication with the camera. These additional components can be selected from the group consisting of: power source; energy transducer; data processing unit; wireless data transmitter; wireless data receiver; computer-to-human interface; microphone; electronic payment component, and pressure sensor. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 18.

In an example, such a hardware configuration (e.g. having one or more cameras attached to finger tip covers) can also be used as "real world mouse" to direct a computer's focus to a particular location in the real world in a manner which is analogous to how a traditional "computer mouse" directs a computer's focus to a particular location (e.g. a cursor) on a computer screen. For example, a person with a finger tip camera can move their finger along a printed page in order to focus a selected computer function on a selected location on that page. For example, this function may comprise reading a text character or identifying an object in a photo at the selected location on that printed page.

In this manner, a "real world mouse" can operate on a text character, photo, or other object on a real world (non-electronic) surface in the same way that a "computer mouse" operates on text character, photo, or other object on a computer (electronic) screen. For example, one can imagine such a device being applied in the following sequence—a person with a finger tip camera points at an object on a printed page and asks "What is this?", a voice recognition function understands the request, the computer analyzes the object within the camera's field of vision, and then the computer says the answer. A similar sequence could help to translate words on a particular portion of a printed page (such as menu in a foreign language) or help vision-impaired people to read a particular portion of a printed page.

Figure 19:
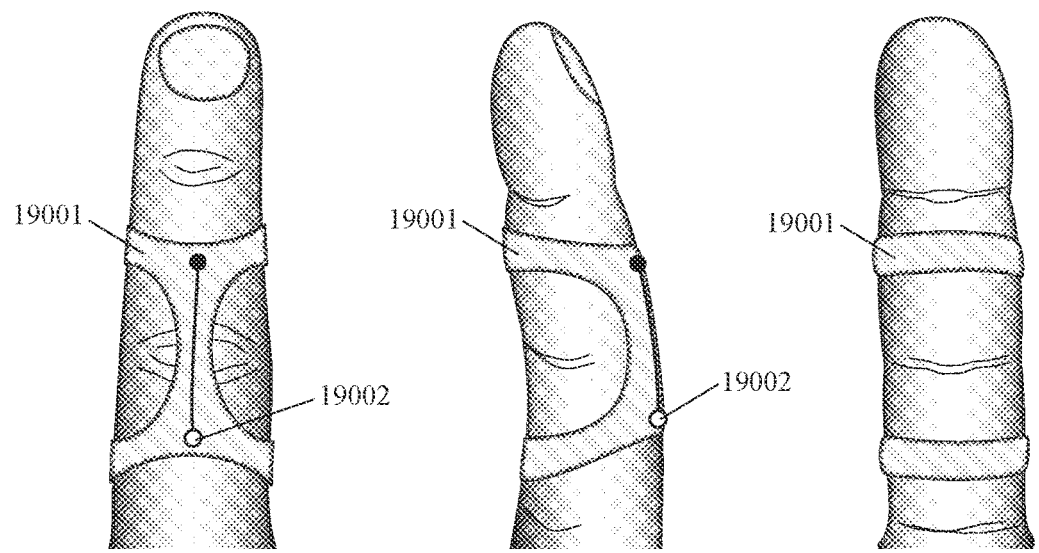
FIG. 19 shows a bi-loop arcuate member and bend sensor spanning the dorsal (upper) surface of a finger joint.

FIG. 19 shows another example of how this invention can be embodied in a wearable device for measuring finger motion and recognizing hand gestures. The left third of FIG. 19 shows this device from a top-down perspective, looking at the upper (dorsal) surface of a person's finger. The middle third of FIG. 19 shows this same device from a side perspective, with the finger having been rotated 90 degrees clockwise. The right third of FIG. 19 shows this same device from a bottom-up perspective, looking at the lower (ventral) surface of the finger.

Specifically, FIG. 19 shows a wearable device for measuring finger motion and recognizing hand gestures comprising: a bi-loop arcuate member 19001, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the dorsal surface of the proximal interphalangeal joint of the finger, wherein the joint-spanning strip spans from the distal loop to the proximal loop, and wherein the joint-spanning strip bends when the proximal interphalangeal joint bends; and a bend sensor 19002, wherein this bend sensor is part of, or attached to the flexible joint-spanning strip, wherein the bend sensor is configured to span at least a portion of the proximal interphalangeal joint, and wherein changes in energy transmitted through and/or generated by the bend sensor are used to measure the motion and/or configuration of the proximal interphalangeal joint.

In an example, bi-loop arcuate member 19001 can be made from an elastic and/or stretchable fabric. In an example, the distal loop, proximal loop, and joint-spanning strip of the bi-loop arcuate member can all be made from elastic and/or stretchable fabric. In an example, the distal and proximal loops can be made from a different material which is less elastic and/or stretchable than the joint-spanning strip. In an example, the distal and proximal loops can be relatively-rigid metal or polymer rings and the joint-spanning strip can be made from elastic and/or stretchable fabric.

In an example, the distal and/or proximal loops of the bi-loop arcuate member can encircle phalanges in cross-sectional planes which are substantially perpendicular to the longitudinal axes of the intermediate phalanx and the proximal phalanx, respectively. In an example, the distal and/or proximal loops of the bi-loop arcuate member can encircle the intermediate phalanx and the proximal phalanx, respectively, in planes which intersect the longitudinal axes of those phalanges at acute angles. In an example, the distal and/or proximal loops can encircle the intermediate phalanx and the proximal phalanx, respectively, around the longitudinal middles of these phalanges. In an example, the joint-spanning strip can be configured to span the dorsal surface of the proximal interphalangeal joint in a manner which is parallel to the central longitudinal axis of the proximal interphalangeal joint.

In an example, the perimeter of the bi-loop arcuate member as viewed from a top-down perspective (looking at the dorsal surface of the finger) can have a shape that looks like a capital letter "I" with rounded vertexes. In an example, the perimeter of the bi-loop arcuate member as viewed from a top-down perspective (looking at the dorsal surface of the finger) can have a shape like a capital letter "I" with an upwardly-curved upper horizontal section, a downwardly-curved lower horizontal section, and a concave vertical connecting section. In an example, the perimeter of the bi-loop arcuate member shape as viewed from a side perspective can have a shape that looks like an arch of a bridge or aqueduct. In an example, the perimeter of the bi-loop arcuate member shape as viewed from a bottom-up perspective (looking at the ventral surface of the finger) can look like the ventral sides of two finger rings, on the intermediate phalanx and on the proximal phalanx, respectively, of the finger.

In an example, changes in electromagnetic, light, or sound energy which is transmitted through a bend sensor spanning a body joint can be measured and analyzed to model the motion and/or configuration of the body joint. In an example, changes in pressure on or within a bend sensor spanning a body joint can be measured and analyzed to model the motion and/or configuration of the body joint. In an example, changes in electrical energy generated by a bend sensor spanning a body joint can be measured and analyzed to model the motion and/or configuration of the body joint.

In an example, a bend sensor can be an electromagnetic energy bend sensor. In an example, an electromagnetic energy bend sensor can be a flexible pathway for the transmission of electromagnetic energy. As a body joint moves, it bends, stretches, elongates, and/or twists an electromagnetic energy bend sensor which spans that joint. This bending, stretching, elongation, and/or twisting changes the flow of electromagnetic energy through the electromagnetic energy bend sensor. These changes in electromagnetic energy flow are then measured and analyzed to estimate the motion and/or configuration of the body joint.

In an example, changes in the flow of electromagnetic energy through an electromagnetic energy bend sensor can be measured by one or more parameters selected from the group consisting of: voltage, resistance, impedance, amperage, current, phase, and wave pattern. In an example, an electromagnetic energy bend sensor can be made with electroconductive fibers, yarns, threads, strands, substrates, layers, and/or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, and variable-resistance sensor. In an example, an electromagnetic energy bend sensor and/or electroconductive members therein can have a sinusoidal configuration.

In an example, electromagnetic energy can be directed into an electromagnetic energy bend sensor at a first location which is distal to the proximal interphalangeal joint (shown in FIG. 19 by a closed circle at the distal end of electromagnetic energy bend sensor 19002) and electromagnetic energy from the electromagnetic energy bend sensor can be measured from a second location which is proximal to the proximal interphalangeal joint (shown in FIG. 19 by an open circle at the proximal end of electromagnetic energy bend sensor 19002), or vice versa.

In an example, an electromagnetic energy bend sensor can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra™, neoprene, nylon, nylon, polyester, wool, silicon rubber, silk, spandex, Danconn or rayon. In an example, a conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, an electromagnetic energy bend sensor can comprise one or more of the following: array of electroconductive members woven using a plain weave, rib weave, basket weave, twill weave, satin weave, leno weave, or mock leno weave; bendable fibers, threads, or yarns; bendable layer, trace, or substrate; elastic fibers, threads, or yarns; elastic layer, trace, or substrate; electroconductive fibers, threads, or yarns; electronically-functional bandage; integrated array of electroconductive members; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; variable-resistance electroconductive fiber, thread, or yarn; water-resistant fibers, threads, or yarns; a layer or coating of metallic nanoparticles; a graphene layer; and water-resistant layer, trace, or substrate.

In an example, a bend sensor can be an optical bend sensor. In an example, an optical bend sensor can be a flexible pathway for the transmission of light energy. As a body joint moves, it bends, stretches, elongates, and/or twists an optical bend sensor which spans that joint. This bending, stretching, elongation, and/or twisting changes the flow of light energy through the optical bend sensor. These changes in light energy flow are then measured and analyzed to estimate the motion and/or configuration of the body joint. In an example, an optical bend sensor can comprise a fiber optic member. In example, optical bend sensor can comprise one or more components selected from the group consisting of: photoelectric sensor, light intensity sensor, infrared light sensor, ultraviolet light sensor, spectroscopy sensor, near-infrared spectroscopy sensor, spectral analysis sensor, spectrophotometer, chromatography sensor, fluorescence sensor, optoelectronic sensor, laser sensor, optical strain detector, and variable-translucence sensor.

In an example, a bend sensor can be a sonic energy bend sensor. In an example, a sonic energy bend sensor can be a flexible pathway for the transmission of sound energy. As a body joint moves, it bends, stretches, elongates, and/or twists a sonic energy bend sensor which spans that joint. This bending, stretching, elongation, and/or twisting changes the flow of sound energy through the sonic energy bend sensor. These changes in sound energy flow are then measured and analyzed to estimate the motion and/or configuration of the body joint. In an example, a sonic energy bend sensor can be a pathway for ultrasonic sound energy. In an example, a sound energy bend sensor can comprise one or more components selected from the group consisting of: microphone, ultrasonic sensor, and acoustic sensor.

In an example, a bend sensor can be a pressure sensor. In an example, changes in pressure on (or within) a pressure sensor can be used to measure the motion and/or configuration of one or more interphalangeal joints. In an example, a pressure sensor can comprise one or more components selected from the group consisting of: capacitive sensor, force sensor, particulate force transducer, electromagnetic pressure sensor, torque sensor, and torsion sensor. In an example, a bend sensor can be piezoelectric and/or piezoresistive. In an example, a piezoelectric bend sensor spanning a body joint generates electromagnetic energy when it is bent, stretched, elongated, and/or twisted and the energy generated is measured to estimate the motion and/or configuration of the body joint.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer.

In an example, this finger-worn device can further comprise: a power source and/or transducer; a data processor, a data transmitter and/or receiver; and a computer-to-human interface. In an example, a power source and/or transducer can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In an example, a data processor can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory. In an example, a data transmitter and/or receiver can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, a computer-to-human interface can further comprise one or more members selected from the group consisting of: a coherent-light image projector; a display screen; a laser; a myostimulating member; a neurostimulating member; a non-coherent-light image projector; a speaker or other sound-emitting member; a synthesized voice; a vibrating or other tactile sensation creating member; an electromagnetic energy emitter; an electronically-functional textile interface; an infrared light emitter; an infrared light projector; and an LED or LED array. In an example, this device can further comprise another type of human-to-computer interface selected from the group consisting of: a button, knob, or dial; a display screen; a microphone; a pressure-sensitive textile array; a spectroscopic sensor; a speech or voice recognition interface; a touch screen; a virtual keypad or keyboard; an electronically-functional textile interface; and an eye gaze tracker.

In an example, this device can further comprise one or more (other) types of electromagnetic energy sensors selected from the group consisting of: electromyography (EMG) sensor, Hall-effect sensor, electromagnetic field sensor, heart rate sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor. In an example, this device can further comprise one or more biochemical sensors selected from the group consisting of: electrochemical sensor, biochemical sensor, glucose sensor, chemoreceptor sensor, gas sensor, microbial sensor, micro-sampling tissue or body fluid sensor, pH level sensor, and photochemical sensor. In an example, this device can further comprise one or more small-scale sensors selected from the group consisting of: Micro-Electro-Mechanical System (MEMS) sensor, nanoscale sensor, nanotube sensor, and nanoparticle sensor. In an example, this device can further comprise one or more additional sensors selected from the group consisting of: humidity sensor, moisture sensor, thermometer, temperature sensor, flow sensor, differential transducer sensor, elastomeric sensor, vibration sensor, helical sensor, revolute joint sensor, ionizing radiation sensor, neurosensor, food consumption sensor, and eye-tracking sensor.

In an example, data from a bend sensor can be analyzed during a calibration period to identify a functional relationship between an interphalangeal joint angle and energy flow through the bend sensor. In an example, an identified functional relationship between an interphalangeal joint angle and energy flow through the bend sensor can be used later to estimate an interphalangeal joint angle based on data concerning energy flow through the bend sensor. In an example, an identified functional relationship between an interphalangeal joint angle and energy flow through the bend sensor can be used to model the motion and/or configuration of an interphalangeal joint.

In an example, the functional relationship between interphalangeal joint angle and energy flow through a bend sensor can be non-linear. In an example, the functional relationship between interphalangeal joint angle and energy flow through a bend sensor can be estimated using a polynomial model. In an example, the functional relationship between interphalangeal joint angle and energy flow through a bend sensor can be estimated using least squares estimation. In an example, the functional relationship between interphalangeal joint angle and energy flow through a bend sensor can be estimated using a spline function. In an example, the functional relationship between interphalangeal joint angle and energy flow through a bend sensor can be estimated using multivariate statistical analysis. In an example, the functional relationship between interphalangeal joint angle and energy flow through a bend sensor can also incorporate data concerning environmental factors such as temperature, moisture level, altitude, time of day, external power availability, and location.

In an example, there can be a first functional relationship between interphalangeal joint angle and energy flow through a bend sensor during joint extension and a second functional relationship between interphalangeal joint angle and energy flow through a bend sensor during joint contraction. In an example, there can be a first functional relationship between interphalangeal joint angle and energy flow through a bend sensor at a first joint motion speed and a second functional relationship between interphalangeal joint angle and energy flow through a bend sensor at a second joint motion speed. In an example, there can be a first functional relationship between interphalangeal joint angle and energy flow through a bend sensor below a selected number of repeated cyclical (extension and contraction) motions and a second functional relationship between interphalangeal joint angle and energy flow through a bend sensor above this selected number of repeated cyclical (extension and contraction) motions. In an example, Fourier analysis can be used to better estimate the functional relationship between joint angle and energy flow through a bend sensor during repeated cyclical (extension and contraction) motions.

In an example, data from two or more bend sensors spanning the same joint can provide more accurate estimation of the functional relationship between interphalangeal joint angle and energy flow through a bend sensor than data from a single bend sensor. In an example, data from different types of bend sensors spanning the same joint can provide more accurate estimation of the functional relationship between interphalangeal joint angle and energy flow through a bend sensor than data from a single type of bend sensor. In an example, there can be a first functional relationship between interphalangeal joint angle and energy flow through a first bend sensor spanning a joint and a second functional relationship between interphalangeal joint angle and energy flow through a second bend sensor spanning the same joint. In an example, multivariate analysis of data from both bend sensors can provide more accurate estimation of joint angle than data from either sensor alone. Accordingly, using multiple bend sensors and/or different types of bend sensors spanning the same joint can provide more-accurate measurement of finger motion and more-accurate recognition of hand gestures.

In an example, data from a first bend sensor spanning a joint in a first configuration can be more accurate for measuring joint angle within a first range of joint angle movement, data from a second bend sensor spanning the joint in a second configuration can be more accurate for measuring joint angle within a second range of joint movement, and multivariate analysis of data from both the first and second bend sensors can provide more accurate measurement of joint angle over the combined range of joint movement than data from either sensor alone. In an example, data from a first type (e.g. electromagnetic, optical, sonic, pressure, or inertial) of bend sensor spanning a joint can be more accurate for measuring joint angle within a first range of joint angle movement, data from a second type (e.g. electromagnetic, optical, sonic, pressure, or inertial) of bend sensor spanning the joint can be more accurate for measuring joint angle within a second range of joint movement, and multivariate analysis of data from both the first and second bend sensors can provide more accurate measurement of joint angle over the combined range of joint movement than data from either sensor alone.

In an example, data from a first bend sensor spanning a joint in a first configuration can be more accurate for measuring joint angle during contraction, data from a second bend sensor spanning the joint in a second configuration can be more accurate for measuring joint angle during extension, and multivariate analysis of data from both the first and second bend sensors can provide more accurate measurement of joint angle during both contraction and extension than data from either sensor alone. In an example, data from a first type (e.g. electromagnetic, optical, sonic, pressure, or inertial) of bend sensor spanning a joint can be more accurate for measuring joint angle during contraction, data from a second type (e.g. electromagnetic, optical, sonic, pressure, or inertial) of bend sensor spanning the joint can be more accurate for measuring joint angle during extension, and multivariate analysis of data from both the first and second bend sensors can provide more accurate measurement of joint angle during both contraction and extension than data from either sensor alone.

In an example, data from a first bend sensor spanning a joint in a first configuration can be more accurate for measuring joint angle during slow motions, data from a second bend sensor spanning the joint in a second configuration can be more accurate for measuring joint angle during fast motions, and multivariate analysis of data from both the first and second bend sensors can provide more accurate measurement of joint angle during a range of slow and fast motions than data from either sensor alone. In an example, data from a first type (e.g. electromagnetic, optical, sonic, pressure, or inertial) of bend sensor spanning a joint can be more accurate for measuring joint angle during slow motions, data from a second type (e.g. electromagnetic, optical, sonic, pressure, or inertial) of bend sensor spanning the joint can be more accurate for measuring joint angle during fast motions, and multivariate analysis of data from both the first and second bend sensors can provide more accurate measurement of joint angle during a range of slow and fast motions than data from either sensor alone.

In an example, data from a first bend sensor spanning a joint in a first configuration can be more accurate for measuring joint angle below a selected number of repeated cyclical (extension and contraction) motions, data from a second bend sensor spanning the joint in a second configuration can be more accurate for measuring joint angle above this selected number of repeated cyclical (extension and contraction) motions, and multivariate analysis of data from both the first and second bend sensors can provide more accurate measurement of joint angle during a range of repeated cycles than data from either sensor alone. In an example, data from a first type (e.g. electromagnetic, optical, sonic, pressure, or inertial) of bend sensor spanning a joint can be more accurate for measuring joint angle below a selected number of repeated cyclical (extension and contraction) motions, data from a second type (e.g. electromagnetic, optical, sonic, pressure, or inertial) of bend sensor spanning the joint can be more accurate for measuring joint angle above this selected number of repeated cyclical (extension and contraction) motions, and multivariate analysis of data from both the first and second bend sensors can provide more accurate measurement of joint angle during a range of repeated cycles than data from either sensor alone.

In an example, the functional relationship between interphalangeal joint angle and energy flow through one or more bend sensors can be analyzed and identified using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; variance; artificial neural network; Bayesian filter or other Bayesian statistical method; chi-squared; eigenvalue decomposition; logit model; machine learning; power spectral density; power spectrum analysis; probit model; and time-series analysis. Other relevant design variations discussed with respect to other examples in this description can also apply to the example shown here in FIG. 19.

Figure 20:
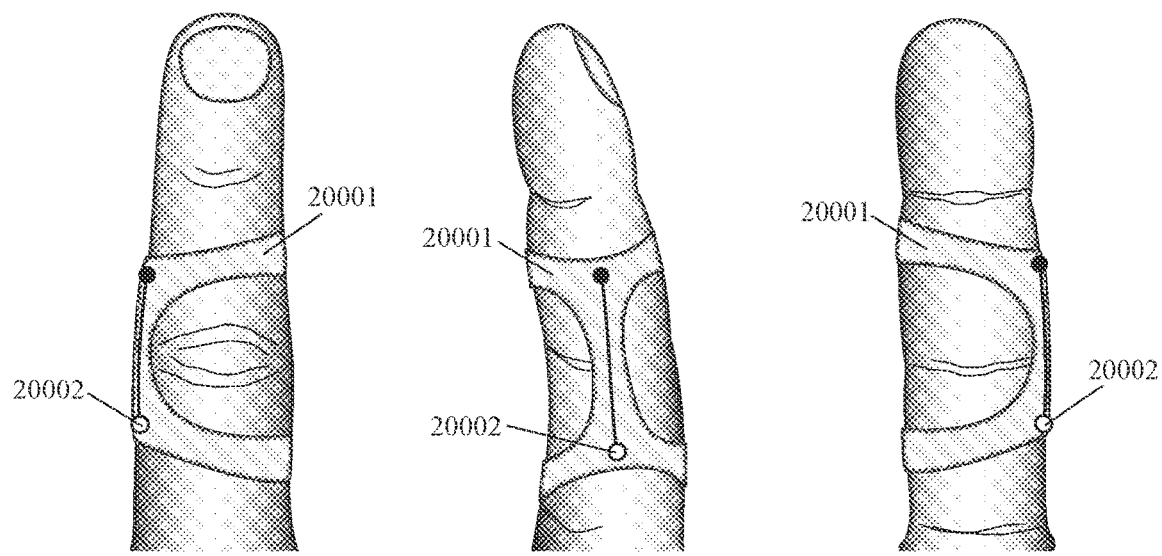
FIG. 20 shows a bi-loop arcuate member and bend sensor spanning the lateral (side) surface of a finger joint.

FIG. 20 shows another example of how this invention can be embodied in a wearable device for measuring finger motion and recognizing hand gestures. The example shown here in FIG. 20 is similar to the one shown in FIG. 19, except that this device is worn rotated 90 degrees around the circumference of the person's finger. Relevant design variations discussed with respect to the example in FIG. 19 and other examples in this description can also apply to the example shown here in FIG. 20. The left third of FIG. 20 shows this device from a top-down perspective, looking at the upper (dorsal) surface of a person's finger. The middle third of FIG. 20 shows this same device from a side perspective, with the finger having been rotated 90 degrees clockwise. The right third of FIG. 20 shows this same device from a bottom-up perspective, looking at the lower (ventral) surface of the finger.

Specifically, FIG. 20 shows a wearable device for measuring finger motion and recognizing hand gestures comprising: a bi-loop arcuate member 20001, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the lateral (side) surface of the proximal interphalangeal joint of the finger, wherein the joint-spanning strip spans from the distal loop to the proximal loop, and wherein the joint-spanning strip bends when the proximal interphalangeal joint bends; and a bend sensor 20002, wherein this bend sensor is integrated into the flexible joint-spanning strip, wherein this bend sensor is configured to span at least a portion of the proximal interphalangeal joint, and wherein changes in energy transmitted through this bend sensor are used to measure the motion and/or configuration of the proximal interphalangeal joint.

Figure 21:
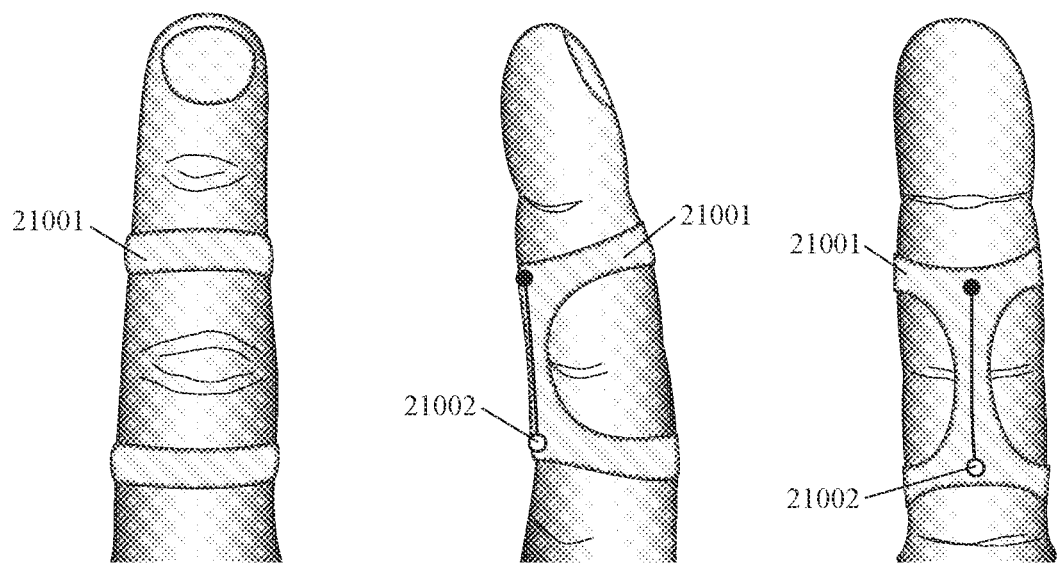
FIG. 21 shows a bi-loop arcuate member and bend sensor spanning the ventral (lower) surface of a finger joint.

FIG. 21 shows another example of how this invention can be embodied in a wearable device for measuring finger motion and recognizing hand gestures. The example shown here in FIG. 21 is similar to the one shown in FIG. 19, except that this device is worn rotated 180 degrees around the circumference of the person's finger. Relevant design variations discussed with respect to the example in FIG. 19 and other examples in this description can also apply to the example shown here in FIG. 21. The left third of FIG. 21 shows this device from a top-down perspective, looking at the upper (dorsal) surface of a person's finger. The middle third of FIG. 21 shows this same device from a side perspective, with the finger having been rotated 90 degrees clockwise. The right third of FIG. 21 shows this same device from a bottom-up perspective, looking at the lower (ventral) surface of the finger.

Specifically, FIG. 21 shows a wearable device for measuring finger motion and recognizing hand gestures comprising: a bi-loop arcuate member 21001, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the ventral surface of the proximal interphalangeal joint of the finger, wherein the joint-spanning strip spans from the distal loop to the proximal loop, and wherein the joint-spanning strip bends when the proximal interphalangeal joint bends; and a bend sensor 21002, wherein this bend sensor is integrated into the flexible joint-spanning strip, wherein this bend sensor is configured to span at least a portion of the proximal interphalangeal joint, and wherein changes in energy transmitted through this bend sensor are used to measure the motion and/or configuration of the proximal interphalangeal joint.

Figure 22:
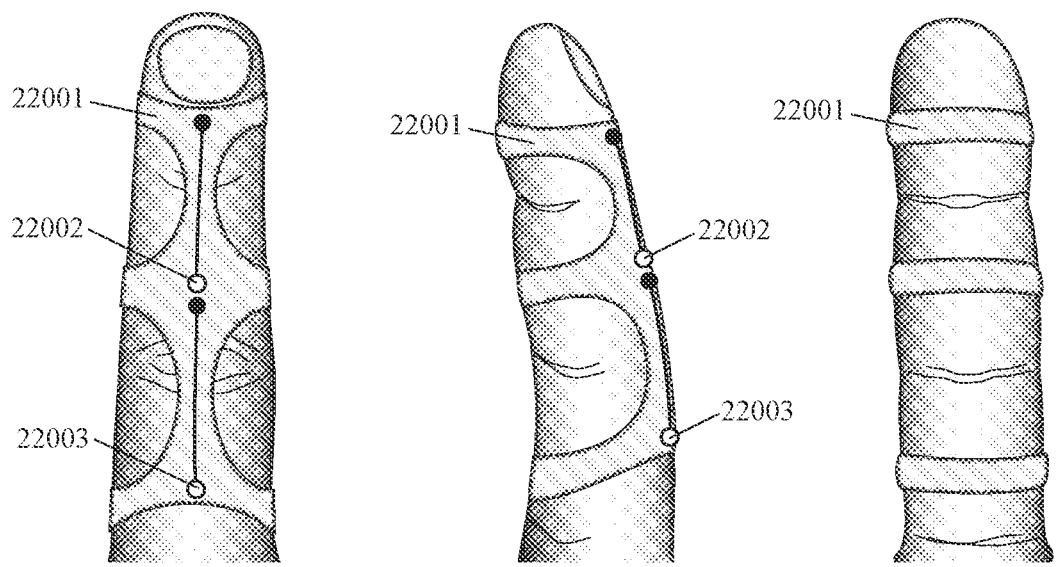
FIG. 22 shows a tri-loop arcuate member and bend sensors spanning the dorsal (upper) surfaces of two finger joints.

FIG. 22 shows another example of how this invention can be embodied in a wearable device for measuring finger motion and recognizing hand gestures. The left third of FIG. 22 shows this device from a top-down perspective, looking at the upper (dorsal) surface of a person's finger. The middle third of FIG. 22 shows this same device from a side perspective, with the finger having been rotated 90 degrees clockwise. The right third of FIG. 22 shows this same device from a bottom-up perspective, looking at the lower (ventral) surface of the finger.

Specifically, FIG. 22 shows a wearable device for measuring finger motion and recognizing hand gestures comprising: (1) a tri-loop arcuate member 22001, wherein this tri-loop arcuate member further comprises: (1a) a distal loop which is configured to encircle the distal phalanx of a finger, (1b) an intermediate loop which is configured to encircle the intermediate phalanx of the finger, (1c) a proximal loop which is configured to encircle the proximal phalanx of the finger, (1d) a distal interphalangeal strip which is configured to span the dorsal surface of the distal interphalangeal joint of the finger, wherein the distal interphalangeal strip spans from the distal loop to the intermediate loop, and wherein the distal interphalangeal strip bends when the distal interphalangeal joint bends; and (1e) a proximal interphalangeal strip which is configured to span the dorsal surface of the proximal interphalangeal joint of the finger, wherein the proximal interphalangeal strip spans from the intermediate loop to the proximal loop, and wherein the proximal interphalangeal strip bends when the proximal interphalangeal joint bends; (2) a distal bend sensor 22002, wherein this distal bend sensor is integrated into the distal interphalangeal strip, wherein this distal bend sensor is configured to span at least a portion of the distal interphalangeal joint, and wherein changes in energy transmitted through the distal bend sensor are used to measure the motion and/or configuration of the distal interphalangeal joint; and (3) a proximal bend sensor 22003, wherein this proximal bend sensor is integrated into the proximal interphalangeal strip, wherein this proximal bend sensor is configured to span at least a portion of the proximal interphalangeal joint, and wherein changes in energy transmitted through the proximal bend sensor are used to measure the motion and/or configuration of the proximal interphalangeal joint.

In an example, a tri-loop arcuate member 22001 can be made from an elastic and/or stretchable fabric. In an example, the loops and strips of a tri-loop arcuate member can all be made from elastic and/or stretchable fabric. In an example, the loops can be made from a material which is less elastic and/or stretchable than the material used to make the strips. In an example, the loops can be relatively-rigid metal or polymer rings and the strips can be made from elastic and/or stretchable fabric.

In an example, the three loops of a tri-loop arcuate member can encircle phalanges in cross-sectional planes which are substantially perpendicular to the longitudinal axes of those phalanges, respectively. In an example, the three loops of a tri-loop arcuate member can encircle phalanges in planes which intersect the longitudinal axes of those phalanges at acute angles, respectively. In an example, the three loops can encircle phalanges around the longitudinal middles of phalanges, respectively. In the example shown in FIG. 22, there are two interphalangeal strips. In an example, a device can have three joint-spanning strips, including one which spans the metacarpal interphalangeal joint.

In an example, a joint-spanning strip can be configured to span the dorsal surface of an interphalangeal joint in a manner which is parallel to the central longitudinal axis of that joint. In an example, distal interphalangeal strip 22002 can be shorter than the proximal interphalangeal strip 22003. In an example, distal interphalangeal strip 22002 and proximal interphalangeal strip 22003 can overlap longitudinally. In the example shown in FIG. 22, the interphalangeal strips span the dorsal (upper) surface of a finger. In an alternative example, the interphalangeal strips can span the lateral (side) surface of a finger. In an alternative example, the interphalangeal strips can span the ventral (lower) surface of a finger. In an example, a tri-loop arcuate member as viewed from a lateral (side) perspective can look like two arches of an aqueduct or a flat bridge. In an example, a tri-loop arcuate member as viewed from a bottom-up perspective (looking at the ventral surface of the finger) can look like the ventral sides of three finger rings.

In an example, changes in electromagnetic, light, or sound energy which is transmitted through a bend sensor spanning a body joint can be measured and analyzed to model the motion and/or configuration of the body joint. In an example, changes in pressure on or within a bend sensor spanning a body joint can be measured and analyzed to model the motion and/or configuration of the body joint. In an example, changes in electrical energy generated by a bend sensor spanning a body joint can be measured and analyzed to model the motion and/or configuration of the body joint.

In an example, a bend sensor can be an electromagnetic energy bend sensor. In an example, an electromagnetic energy bend sensor can be a flexible pathway for the transmission of electromagnetic energy. As a body joint moves, it bends, stretches, elongates, and/or twists an electromagnetic energy bend sensor which spans that joint. This bending, stretching, elongation, and/or twisting changes the flow of electromagnetic energy through the electromagnetic energy bend sensor. These changes in electromagnetic energy flow are then measured and analyzed to estimate the motion and/or configuration of the body joint.

In an example, changes in the flow of electromagnetic energy through an electromagnetic energy bend sensor can be measured by one or more parameters selected from the group consisting of: voltage, resistance, impedance, amperage, current, phase, and wave pattern. In an example, an electromagnetic energy bend sensor can be made with electroconductive fibers, yarns, threads, strands, substrates, layers, and/or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, and variable-resistance sensor. In an example, an electromagnetic energy bend sensor and/or electroconductive members therein can have a sinusoidal configuration.

In an example, a bend sensor can be an optical bend sensor. In an example, an optical bend sensor can be a flexible pathway for the transmission of light energy. As a body joint moves, it bends, stretches, elongates, and/or twists an optical bend sensor which spans that joint. This bending, stretching, elongation, and/or twisting changes the flow of light energy through the optical bend sensor. These changes in light energy flow are then measured and analyzed to estimate the motion and/or configuration of the body joint. In an example, an optical bend sensor can comprise a fiber optic member. In example, optical bend sensor can comprise one or more components selected from the group consisting of: photoelectric sensor, light intensity sensor, infrared light sensor, ultraviolet light sensor, spectroscopy sensor, near-infrared spectroscopy sensor, spectral analysis sensor, spectrophotometer, chromatography sensor, fluorescence sensor, optoelectronic sensor, laser sensor, optical strain detector, and variable-translucence sensor.

In an example, a bend sensor can be a sonic energy bend sensor. In an example, a sonic energy bend sensor can be a flexible pathway for the transmission of sound energy. As a body joint moves, it bends, stretches, elongates, and/or twists a sonic energy bend sensor which spans that joint. This bending, stretching, elongation, and/or twisting changes the flow of sound energy through the sonic energy bend sensor. These changes in sound energy flow are then measured and analyzed to estimate the motion and/or configuration of the body joint. In an example, a sonic energy bend sensor can be a pathway for ultrasonic sound energy. In an example, a sound energy bend sensor can comprise one or more components selected from the group consisting of: microphone, ultrasonic sensor, and acoustic sensor.

In an example, a bend sensor can be a pressure sensor. In an example, changes in pressure on (or within) a pressure sensor can be used to measure the motion and/or configuration of one or more interphalangeal joints. In an example, a pressure sensor can comprise one or more components selected from the group consisting of: capacitive sensor, force sensor, particulate force transducer, electromagnetic pressure sensor, torque sensor, and torsion sensor. In an example, a bend sensor can be piezoelectric and/or piezoresistive. In an example, a piezoelectric bend sensor spanning a body joint generates electromagnetic energy when it is bent, stretched, elongated, and/or twisted and the energy generated is measured to estimate the motion and/or configuration of the body joint.

In an example, data from a bend sensor can be analyzed during a calibration period to identify a functional relationship between interphalangeal joint angle and energy flow through the bend sensor. In an example, an identified functional relationship between interphalangeal joint angle and energy flow through the bend sensor can be used later to estimate interphalangeal joint angle based on data concerning energy flow through the bend sensor. In an example, an identified functional relationship between interphalangeal joint angle and energy flow through the bend sensor can be used to model the motion and/or configuration of an interphalangeal joint.

In an example, the functional relationship between interphalangeal joint angle and energy flow through a bend sensor can be non-linear. In an example, the functional relationship between interphalangeal joint angle and energy flow through a bend sensor can be estimated using a polynomial model. In an example, the functional relationship between interphalangeal joint angle and energy flow through a bend sensor can be estimated using least squares estimation. In an example, the functional relationship between interphalangeal joint angle and energy flow through a bend sensor can be estimated using a spline function. In an example, the functional relationship between interphalangeal joint angle and energy flow through a bend sensor can be estimated using multivariate statistical analysis. In an example, the functional relationship between interphalangeal joint angle and energy flow through a bend sensor can also incorporate data concerning environmental factors such as temperature, moisture level, altitude, time of day, external power availability, and location.

In an example, there can be a first functional relationship between interphalangeal joint angle and energy flow through a bend sensor during joint extension and a second functional relationship between interphalangeal joint angle and energy flow through a bend sensor during joint contraction. In an example, there can be a first functional relationship between interphalangeal joint angle and energy flow through a bend sensor at a first joint motion speed and a second functional relationship between interphalangeal joint angle and energy flow through a bend sensor at a second joint motion speed. In an example, there can be a first functional relationship between interphalangeal joint angle and energy flow through a bend sensor below a selected number of repeated cyclical (extension and contraction) motions and a second functional relationship between interphalangeal joint angle and energy flow through a bend sensor above this selected number of repeated cyclical (extension and contraction) motions. In an example, Fourier analysis can be used to better estimate the functional relationship between joint angle and energy flow through a bend sensor during repeated cyclical (extension and contraction) motions.

In an example, data from two or more bend sensors spanning the same joint can provide more accurate estimation of the functional relationship between interphalangeal joint angle and energy flow through a bend sensor than data from a single bend sensor. In an example, data from different types of bend sensors spanning the same joint can provide more accurate estimation of the functional relationship between interphalangeal joint angle and energy flow through a bend sensor than data from a single type of bend sensor. In an example, there can be a first functional relationship between interphalangeal joint angle and energy flow through a first bend sensor spanning a joint and a second functional relationship between interphalangeal joint angle and energy flow through a second bend sensor spanning the same joint. In an example, multivariate analysis of data from both bend sensors can provide more accurate estimation of joint angle than data from either sensor alone. Accordingly, using multiple bend sensors and/or different types of bend sensors spanning the same joint can provide more-accurate measurement of finger motion and more-accurate recognition of hand gestures.

In an example, data from a first bend sensor spanning a joint in a first configuration can be more accurate for measuring joint angle within a first range of joint angle movement, data from a second bend sensor spanning the joint in a second configuration can be more accurate for measuring joint angle within a second range of joint movement, and multivariate analysis of data from both the first and second bend sensors can provide more accurate measurement of joint angle over the combined range of joint movement than data from either sensor alone. In an example, data from a first type (e.g. electromagnetic, optical, sonic, pressure, or inertial) of bend sensor spanning a joint can be more accurate for measuring joint angle within a first range of joint angle movement, data from a second type (e.g. electromagnetic, optical, sonic, pressure, or inertial) of bend sensor spanning the joint can be more accurate for measuring joint angle within a second range of joint movement, and multivariate analysis of data from both the first and second bend sensors can provide more accurate measurement of joint angle over the combined range of joint movement than data from either sensor alone.

In an example, data from a first bend sensor spanning a joint in a first configuration can be more accurate for measuring joint angle during contraction, data from a second bend sensor spanning the joint in a second configuration can be more accurate for measuring joint angle during extension, and multivariate analysis of data from both the first and second bend sensors can provide more accurate measurement of joint angle during both contraction and extension than data from either sensor alone. In an example, data from a first type (e.g. electromagnetic, optical, sonic, pressure, or inertial) of bend sensor spanning a joint can be more accurate for measuring joint angle during contraction, data from a second type (e.g. electromagnetic, optical, sonic, pressure, or inertial) of bend sensor spanning the joint can be more accurate for measuring joint angle during extension, and multivariate analysis of data from both the first and second bend sensors can provide more accurate measurement of joint angle during both contraction and extension than data from either sensor alone.

In an example, data from a first bend sensor spanning a joint in a first configuration can be more accurate for measuring joint angle during slow motions, data from a second bend sensor spanning the joint in a second configuration can be more accurate for measuring joint angle during fast motions, and multivariate analysis of data from both the first and second bend sensors can provide more accurate measurement of joint angle during a range of slow and fast motions than data from either sensor alone. In an example, data from a first type (e.g. electromagnetic, optical, sonic, pressure, or inertial) of bend sensor spanning a joint can be more accurate for measuring joint angle during slow motions, data from a second type (e.g. electromagnetic, optical, sonic, pressure, or inertial) of bend sensor spanning the joint can be more accurate for measuring joint angle during fast motions, and multivariate analysis of data from both the first and second bend sensors can provide more accurate measurement of joint angle during a range of slow and fast motions than data from either sensor alone.

In an example, data from a first bend sensor spanning a joint in a first configuration can be more accurate for measuring joint angle below a selected number of repeated cyclical (extension and contraction) motions, data from a second bend sensor spanning the joint in a second configuration can be more accurate for measuring joint angle above this selected number of repeated cyclical (extension and contraction) motions, and multivariate analysis of data from both the first and second bend sensors can provide more accurate measurement of joint angle during a range of repeated cycles than data from either sensor alone. In an example, data from a first type (e.g. electromagnetic, optical, sonic, pressure, or inertial) of bend sensor spanning a joint can be more accurate for measuring joint angle below a selected number of repeated cyclical (extension and contraction) motions, data from a second type (e.g. electromagnetic, optical, sonic, pressure, or inertial) of bend sensor spanning the joint can be more accurate for measuring joint angle above this selected number of repeated cyclical (extension and contraction) motions, and multivariate analysis of data from both the first and second bend sensors can provide more accurate measurement of joint angle during a range of repeated cycles than data from either sensor alone.

In an example, the functional relationship between interphalangeal joint angle and energy flow through one or more bend sensors can be analyzed and identified using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer.

In an example, this finger-worn device can further comprise: a power source and/or transducer; a data processor, a data transmitter and/or receiver; and a computer-to-human interface. In an example, a power source and/or transducer can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In an example, a data processor can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory. In an example, a data transmitter and/or receiver can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, a computer-to-human interface can further comprise one or more members selected from the group consisting of: a coherent-light image projector; a display screen; a laser; a myostimulating member; a neurostimulating member; a non-coherent-light image projector; a speaker or other sound-emitting member; a synthesized voice; a vibrating or other tactile sensation creating member; an electromagnetic energy emitter; an electronically-functional textile interface; an infrared light emitter; an infrared light projector; and an LED or LED array. In an example, this device can further comprise another type of human-to-computer interface selected from the group consisting of: a button, knob, or dial; a display screen; a microphone; a pressure-sensitive textile array; a spectroscopic sensor; a speech or voice recognition interface; a touch screen; a virtual keypad or keyboard; an electronically-functional textile interface; and an eye gaze tracker.

In an example, this device can further comprise one or more (other) types of electromagnetic energy sensors selected from the group consisting of: electromyography (EMG) sensor, Hall-effect sensor, electromagnetic field sensor, heart rate sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor. In an example, this device can further comprise one or more biochemical sensors selected from the group consisting of: electrochemical sensor, biochemical sensor, glucose sensor, chemoreceptor sensor, gas sensor, microbial sensor, microsampling tissue or body fluid sensor, pH level sensor, and photochemical sensor. In an example, this device can further comprise one or more small-scale sensors selected from the group consisting of: Micro-Electro-Mechanical System (MEMS) sensor, nanoscale sensor, nanotube sensor, and nanoparticle sensor. In an example, this device can further comprise one or more additional sensors selected from the group consisting of: humidity sensor, moisture sensor, thermometer, temperature sensor, flow sensor, differential transducer sensor, elastomeric sensor, vibration sensor, helical sensor, revolute joint sensor, ionizing radiation sensor, neurosensor, food consumption sensor, and eye-tracking sensor. Other relevant design variations discussed with respect to other examples in this description can also apply to the example shown here in FIG. 22.

Figure 23:
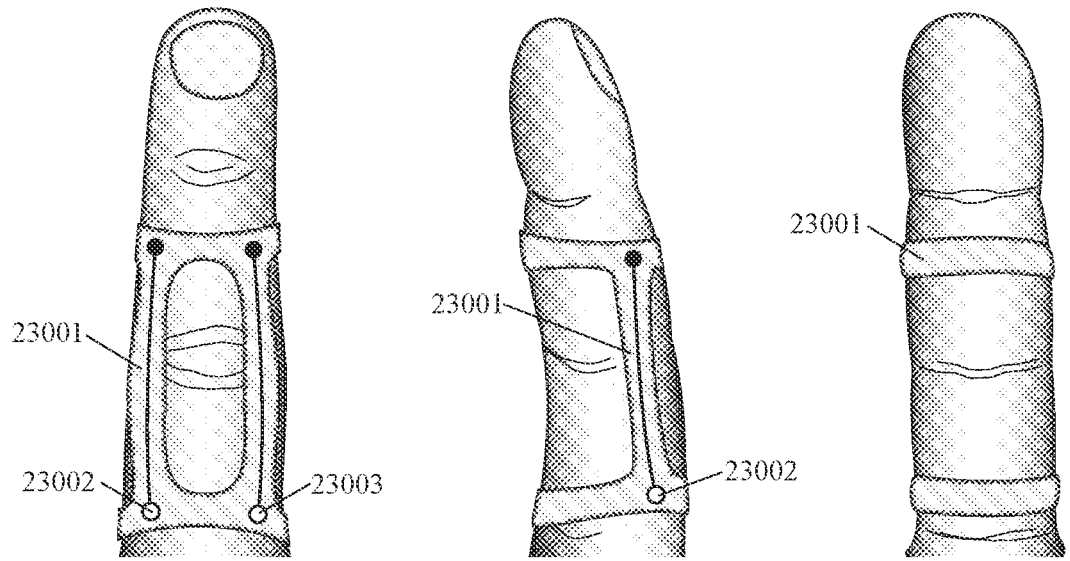
FIG. 23 shows a bi-loop arcuate member with two longitudinal interphalangeal strips.

FIG. 23 shows another example of how this invention can be embodied in a wearable device for measuring finger motion and recognizing hand gestures. The left third of FIG. 23 shows this device from a top-down perspective, looking at the upper (dorsal) surface of a person's finger. The middle third of FIG. 23 shows this same device from a side perspective, with the finger having been rotated 90 degrees clockwise. The right third of FIG. 23 shows this same device from a bottom-up perspective, looking at the lower (ventral) surface of the finger.

Specifically, FIG. 23 shows a wearable device for measuring finger motion and recognizing hand gestures comprising: (a) a two-strip arcuate member 23001, wherein this two-strip arcuate member further comprises: a distal loop which is configured to encircle the intermediate phalanx of a finger; a proximal loop which is configured to encircle the proximal phalanx of the finger; a first interphalangeal strip which is configured to span the distal interphalangeal joint of the finger crossing a first radial location of the distal interphalangeal joint, wherein this first interphalangeal strip spans from the distal loop to the proximal loop, and wherein this first interphalangeal strip bends when the distal interphalangeal joint bends; and a second interphalangeal strip which is configured to span the distal interphalangeal joint of the finger crossing a second radial location of the distal interphalangeal joint, wherein this second radial location is different than the first radial location, wherein this second interphalangeal strip spans from the distal loop to the proximal loop, and wherein this second interphalangeal strip bends when the distal interphalangeal joint bends; (b) a first bend sensor 23002, wherein this first bend sensor is integrated into the first interphalangeal strip, wherein this first bend sensor is configured to span at least a portion of the distal interphalangeal joint, and wherein changes in energy transmitted through the first bend sensor are used to measure the motion and/or configuration of the distal interphalangeal joint; and (c) a second bend sensor 23003, wherein this second bend sensor is integrated into the second interphalangeal strip, wherein this second bend sensor is configured to span at least a portion of the distal interphalangeal joint, and wherein changes in energy transmitted through the second bend sensor are used to measure the motion and/or configuration of the distal interphalangeal joint.

In an example, a first radial location can be on the left side of the circumference of a finger and a second radial location can be on the right side of the circumference of a finger, or vice versa. In an example, radial locations around the circumference of a finger can be defined relative to: a 0-degree point on the most dorsal (upper) surface of the finger circumference; a 90-degree point on the right lateral (side) surface of the finger circumference; an 180-degree point on the most ventral (lower) surface of the finger circumference; and a 270-degree point on the left lateral (side) surface of the finger circumference. In an example, a first radial location can be selected within a range of 270-350 degrees and a second radial location can be selected with a range of 10-90 degrees, or vice versa. In an example, a first radial location can be selected within a range of 190-270 degrees and a second radial location can be selected with a range of 90-170 degrees, or vice versa.

In an example, the longitudinal axes of first and second interphalangeal strips can be substantially parallel. In an example, the longitudinal axes of first and second bend sensors can be substantially parallel. In an example, the longitudinal axes of first and second interphalangeal strips can diverge at an angle in the range of 5-25 degrees in a distal-to-proximal direction. In an example, the longitudinal axes of first and second bend sensors can diverge at an angle in the range of 5-25 degrees in a distal-to-proximal direction.

In an example, a two-strip arcuate member 23001 can be made from an elastic and/or stretchable fabric. In an example, the loops and strips of a two-strip arcuate member can all be made from elastic and/or stretchable fabric. In an example, the loops can be made from a material which is less elastic and/or stretchable than the material used to make the strips. In an example, the loops can be relatively-rigid metal or polymer rings and the strips can be made from elastic and/or stretchable fabric.

In an example, the loops of a two-strip arcuate member can encircle phalanges in cross-sectional planes which are substantially perpendicular to the longitudinal axes of those phalanges, respectively. In an example, the loops of a two-strip arcuate member can encircle phalanges in planes which intersect the longitudinal axes of those phalanges at acute angles, respectively. In an example, the loops can encircle phalanges around the longitudinal middles of those phalanges, respectively.

In an example, the two strips of this device can each be configured to span an interphalangeal joint in a manner which is substantially parallel to the central longitudinal axis of that joint. In an example, two strips can be of equal length. In an example, one strip can be longer than the other. In an example, there can be a gap between the two strips on the dorsal (upper) surface of the finger. In an example, this gap can have a shape which is selected from the group consisting of: oval, oblong, ellipse, egg-shaped, rectangle with rounded vertexes, rectangle, circle, trapezoid, and trapezoid with rounded vertexes. In an example, a two-strip arcuate member as viewed from a lateral (side) perspective can look like the capital letter "I" with the right-side portions partially chopped off. In an example, a two-strip arcuate member as viewed from a bottom-up perspective (looking at the ventral surface of the finger) can look like the ventral sides of two finger rings.

In an example, changes in electromagnetic, light, or sound energy which is transmitted through a bend sensor spanning a body joint can be measured and analyzed to model the motion and/or configuration of the body joint. In an example, changes in pressure on or within a bend sensor spanning a body joint can be measured and analyzed to model the motion and/or configuration of the body joint. In an example, changes in electrical energy generated by a bend sensor spanning a body joint can be measured and analyzed to model the motion and/or configuration of the body joint.

In an example, a bend sensor can be an electromagnetic energy bend sensor. In an example, an electromagnetic energy bend sensor can be a flexible pathway for the transmission of electromagnetic energy. As a body joint moves, it bends, stretches, elongates, and/or twists an electromagnetic energy bend sensor which spans that joint. This bending, stretching, elongation, and/or twisting changes the flow of electromagnetic energy through the electromagnetic energy bend sensor. These changes in electromagnetic energy flow are then measured and analyzed to estimate the motion and/or configuration of the body joint.

In an example, changes in the flow of electromagnetic energy through an electromagnetic energy bend sensor can be measured by one or more parameters selected from the group consisting of: voltage, resistance, impedance, amperage, current, phase, and wave pattern. In an example, an electromagnetic energy bend sensor can be made with electroconductive fibers, yarns, threads, strands, substrates, layers, and/or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, and variable-resistance sensor. In an example, an electromagnetic energy bend sensor and/or electroconductive members therein can have a sinusoidal configuration.

In an example, a bend sensor can be an optical bend sensor. In an example, an optical bend sensor can be a flexible pathway for the transmission of light energy. As a body joint moves, it bends, stretches, elongates, and/or twists an optical bend sensor which spans that joint. This bending, stretching, elongation, and/or twisting changes the flow of light energy through the optical bend sensor. These changes in light energy flow are then measured and analyzed to estimate the motion and/or configuration of the body joint. In an example, an optical bend sensor can comprise a fiber optic member. In example, optical bend sensor can comprise one or more components selected from the group consisting of: photoelectric sensor, light intensity sensor, infrared light sensor, ultraviolet light sensor, spectroscopy sensor, near-infrared spectroscopy sensor, spectral analysis sensor, spectrophotometer, chromatography sensor, fluorescence sensor, optoelectronic sensor, laser sensor, optical strain detector, and variable-translucence sensor.

In an example, a bend sensor can be a sonic energy bend sensor. In an example, a sonic energy bend sensor can be a flexible pathway for the transmission of sound energy. As a body joint moves, it bends, stretches, elongates, and/or twists a sonic energy bend sensor which spans that joint. This bending, stretching, elongation, and/or twisting changes the flow of sound energy through the sonic energy bend sensor. These changes in sound energy flow are then measured and analyzed to estimate the motion and/or configuration of the body joint. In an example, a sonic energy bend sensor can be a pathway for ultrasonic sound energy. In an example, a sound energy bend sensor can comprise one or more components selected from the group consisting of: microphone, ultrasonic sensor, and acoustic sensor.

In an example, a bend sensor can be a pressure sensor. In an example, changes in pressure on (or within) a pressure sensor can be used to measure the motion and/or configuration of one or more interphalangeal joints. In an example, a pressure sensor can comprise one or more components selected from the group consisting of: capacitive sensor, force sensor, particulate force transducer, electromagnetic pressure sensor, torque sensor, and torsion sensor. In an example, a bend sensor can be piezoelectric and/or piezoresistive. In an example, a piezoelectric bend sensor spanning a body joint generates electromagnetic energy when it is bent, stretched, elongated, and/or twisted and the energy generated is measured to estimate the motion and/or configuration of the body joint.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer.

In an example, this finger-worn device can further comprise: a power source and/or transducer; a data processor, a data transmitter and/or receiver; and a computer-to-human interface. In an example, a power source and/or transducer can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In an example, a data processor can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory. In an example, a data transmitter and/or receiver can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device. Other relevant design variations discussed with respect to other examples in this description can also apply to the example shown here in FIG. 23.

Figure 24:
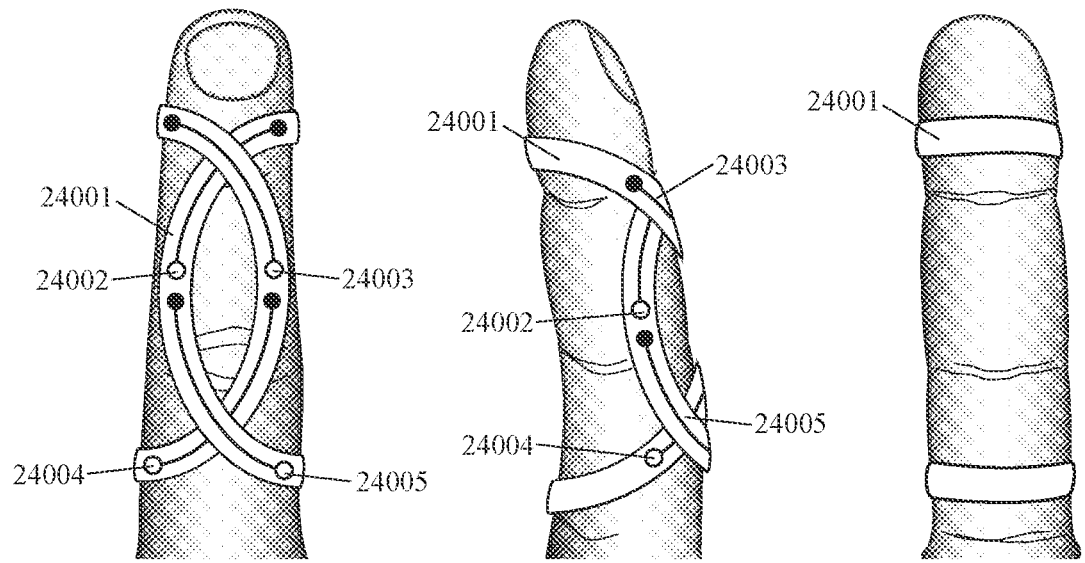
FIG. 24 shows two overlapping arcuate loops spanning the dorsal (upper) side of a finger joint.

FIG. 24 shows another example of how this invention can be embodied in a wearable device for measuring finger motion and recognizing hand gestures. The left third of FIG. 24 shows this device from a top-down perspective, looking at the upper (dorsal) surface of a person's finger. The middle third of FIG. 24 shows this same device from a side perspective, with the finger having been rotated 90 degrees clockwise. The right third of FIG. 24 shows this same device from a bottom-up perspective, looking at the lower (ventral) surface of the finger.

Specifically, FIG. 24 shows a wearable device for measuring finger motion and recognizing hand gestures comprising: an overlapping loop 24001, wherein this loop is configured to encircle the circumference of a person's finger, and wherein the ends of this loop overlap each other; a first set of bend sensors (24002 and 24003) which are configured to span the distal interphalangeal joint of the finger; and a second set of bend sensors (24004 and 24005) which are configured to span the proximal interphalangeal joint of the finger.

In an example, an overlapping loop can be configured to longitudinally span a finger from the distal phalanx to the proximal phalanx. In an example, before an overlapping loop is curved to fit around the circumference of a finger, it can have a shape which is selected from the group consisting of: circle, oval, oblong, ellipse, egg-shape, and rectangle with rounded vertexes. In an example, after an overlapping loop is curved to fit around the circumference of a finger, it can have a shape which generally cylindrical with gaps, including a convex upper (dorsal) gap wherein the ends of the loop overlap and a lower (ventral) gap comprising the non-overlapping portion of the interior of the loop. As seen in the left third of FIG. 24, an overlapping loop seen on the upper (dorsal) surface of a person's finger can look like a stylized "fish with two tails" (or like a central convex lens wherein the arcs extend past the vertexes at both ends). In an example, an overlapping loop seen on the lower (ventral) surface of a person's finger can look like the ventral portions of two finger rings.

In an example, the ends of a loop can be configured to overlap primarily or entirely on the upper (dorsal) surface of a finger. In an example, the ends of a loop can be configured to overlap primarily or entirely on the lower (ventral) surface of a finger. In an example, the ends of a loop can be configured to overlap a portion of the circumference of a finger which is between 5% and 50% of the total circumference of the finger when the loop is placed on the finger. In an example, the ends of a loop after the loop is curved can overlap between 5% and 50% of the pre-curved interior of the loop.

In an example, an overlapping loop can stretchable, elastic, and/or expandable. In an example, an overlapping loop can be stretched and/or expanded so that it can slide over a finger tip onto a finger. In an example, the ends of a loop can be permanently overlapping and attached to each other. In an example, the ends of a loop can be already overlapping as a loop is slid over a finger tip onto a finger. In an example, overlapping ends of a loop can be interlocked and/or interwoven. In an example, the two ends of a loop can intersect each other, including a distal intersection location and a proximal intersection location. In an example, a distal intersection location can be on the distal phalanx of a finger and a proximal intersection location can be on the proximal phalanx of a finger.

In an example, the overlapping ends of a loop can be attached to each other to hold the loop onto a finger and can be separated from each other for detachment from the finger. In an example, an overlapping loop can be attached to a finger by encircling the loop around the circumference of the finger and then attaching the ends of the loop to each other on the finger. In an example, the ends of a loop can be attached to each other by an attachment mechanism selected from the group consisting of: hook-and-eye, buckle, clip, prong, clasp, hook, pin, button, plug, protrusion-and-eye, snap, zipper, and magnet.

In an example a first set of bend sensors or a second set of bend sensors can each comprise only one bend sensor, respectively. In an example a first set of bend sensors or a second set of bend sensors can each comprise two bend sensors, respectively. In an example a first set of bend sensors or a second set of bend sensors can each comprise more than two bend sensors, respectively. In an example, there can be two bend sensors, one from each set, on each overlapping end of a loop. In an example, two or more bend sensors in a first set of bend sensors can intersect and/or overlap each other. In an example, two or more bend sensors in a second set of bend sensors can intersect and/or overlap each other. In an example, energy can be directed into a bend sensor at first location which is distal to a joint (as shown by a closed circle at the distal end of a bend sensor in FIG. 24) and energy from the bend sensor can be measured from a second location which is proximal to the joint (as shown by an open circle at the proximal end of a bend sensor in FIG. 24), or vice versa.

In an example, changes in electromagnetic, light, or sound energy which is transmitted through a bend sensor spanning a body joint can be measured and analyzed to model the motion and/or configuration of the body joint. In an example, changes in pressure on or within a bend sensor spanning a body joint can be measured and analyzed to model the motion and/or configuration of the body joint. In an example, changes in electrical energy generated by a bend sensor spanning a body joint can be measured and analyzed to model the motion and/or configuration of the body joint.

In an example, a bend sensor can be an electromagnetic energy bend sensor. In an example, an electromagnetic energy bend sensor can be a flexible pathway for the transmission of electromagnetic energy. As a body joint moves, it bends, stretches, elongates, and/or twists an electromagnetic energy bend sensor which spans that joint. This bending, stretching, elongation, and/or twisting changes the flow of electromagnetic energy through the electromagnetic energy bend sensor. These changes in electromagnetic energy flow are then measured and analyzed to estimate the motion and/or configuration of the body joint.

In an example, changes in the flow of electromagnetic energy through an electromagnetic energy bend sensor can be measured by one or more parameters selected from the group consisting of: voltage, resistance, impedance, amperage, current, phase, and wave pattern. In an example, an electromagnetic energy bend sensor can be made with electroconductive fibers, yarns, threads, strands, substrates, layers, and/or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, and variable-resistance sensor. In an example, an electromagnetic energy bend sensor and/or electroconductive members therein can have a sinusoidal configuration.

In an example, a bend sensor can be an optical bend sensor. In an example, an optical bend sensor can be a flexible pathway for the transmission of light energy. As a body joint moves, it bends, stretches, elongates, and/or twists an optical bend sensor which spans that joint. This bending, stretching, elongation, and/or twisting changes the flow of light energy through the optical bend sensor. These changes in light energy flow are then measured and analyzed to estimate the motion and/or configuration of the body joint. In an example, an optical bend sensor can comprise a fiber optic member. In example, optical bend sensor can comprise one or more components selected from the group consisting of: photoelectric sensor, light intensity sensor, infrared light sensor, ultraviolet light sensor, spectroscopy sensor, near-infrared spectroscopy sensor, spectral analysis sensor, spectrophotometer, chromatography sensor, fluorescence sensor, optoelectronic sensor, laser sensor, optical strain detector, and variable-translucence sensor.

In an example, a bend sensor can be a sonic energy bend sensor. In an example, a sonic energy bend sensor can be a flexible pathway for the transmission of sound energy. As a body joint moves, it bends, stretches, elongates, and/or twists a sonic energy bend sensor which spans that joint. This bending, stretching, elongation, and/or twisting changes the flow of sound energy through the sonic energy bend sensor. These changes in sound energy flow are then measured and analyzed to estimate the motion and/or configuration of the body joint. In an example, a sonic energy bend sensor can be a pathway for ultrasonic sound energy. In an example, a sound energy bend sensor can comprise one or more components selected from the group consisting of: microphone, ultrasonic sensor, and acoustic sensor.

In an example, a bend sensor can be a pressure sensor. In an example, changes in pressure on (or within) a pressure sensor can be used to measure the motion and/or configuration of one or more interphalangeal joints. In an example, a pressure sensor can comprise one or more components selected from the group consisting of: capacitive sensor, force sensor, particulate force transducer, electromagnetic pressure sensor, torque sensor, and torsion sensor. In an example, a bend sensor can be piezoelectric and/or piezoresistive. In an example, a piezoelectric bend sensor spanning a body joint generates electromagnetic energy when it is bent, stretched, elongated, and/or twisted and the energy generated is measured to estimate the motion and/or configuration of the body joint.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 24.

Figure 25:
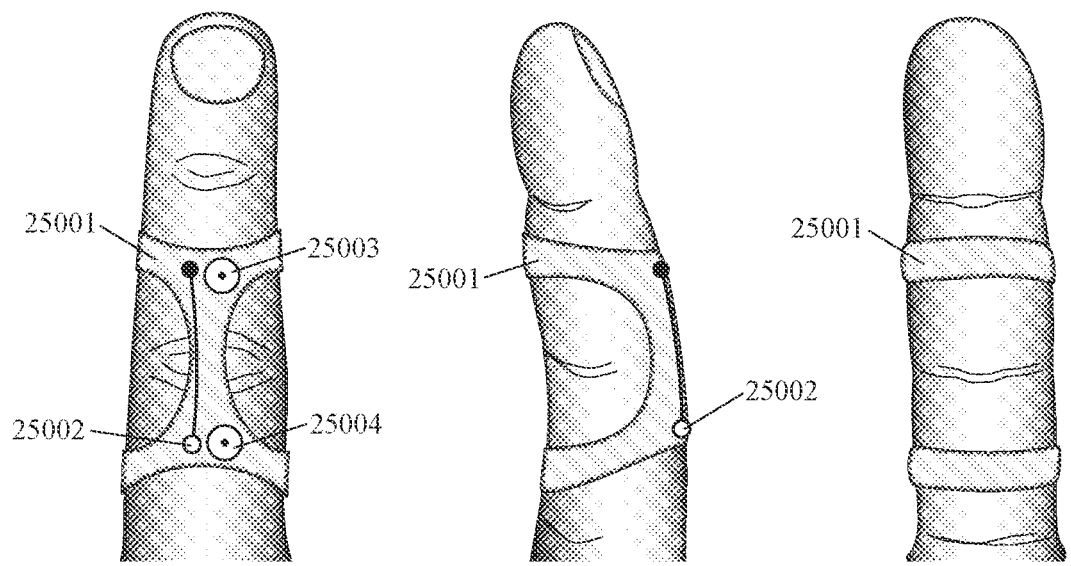
FIG. 25 shows a bi-loop arcuate member with a bend sensor and inertial motion sensors.

FIG. 25 shows another example of how this invention can be embodied in a wearable device for measuring finger motion and recognizing hand gestures. This example is similar to the one shown in FIG. 19 except that it has inertial motion sensors in addition to a bend sensor for measuring the configuration and/or movement of an interphalangeal joint. The left third of FIG. 25 shows this device from a top-down perspective, looking at the upper (dorsal) surface of a person's finger. The middle third of FIG. 25 shows this same device from a side perspective, with the finger having been rotated 90 degrees clockwise. The right third of FIG. 25 shows this same device from a bottom-up perspective, looking at the lower (ventral) surface of the finger.

Specifically, FIG. 25 shows a wearable device for measuring finger motion and recognizing hand gestures comprising: (a) a bi-loop arcuate member 25001, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the dorsal surface of the proximal interphalangeal joint of the finger, wherein the joint-spanning strip spans from the distal loop to the proximal loop, and wherein the joint-spanning strip bends when the proximal interphalangeal joint bends; (b) a bend sensor 25002, wherein this bend sensor is part of, or attached to the flexible joint-spanning strip, wherein the bend sensor is configured to span at least a portion of the proximal interphalangeal joint, and wherein changes in energy transmitted through and/or generated by the bend sensor are used to measure the motion and/or configuration of the proximal interphalangeal joint; (c) a distal inertial motion sensor 25003 which is part of, or attached to, the flexible joint-spanning strip at a location which is configured to be distal to the proximal interphalangeal joint of the finger; and (d) a proximal inertial motion sensor 25004 which is part of, or attached to, the flexible joint-spanning strip at a location which is configured to be proximal to the proximal interphalangeal joint of the finger.

The bi-loop arcuate member herein can be configured as described previously in the narrative which accompanies FIG. 19. An inertial motion sensor can be selected from the group consisting of: multi-axial accelerometer, gyroscope, and inclinometer. A bend sensor herein can be selected and configured as described previously in the narrative which accompanies FIG. 19. Other relevant design variations discussed with respect to other examples in this description can also apply to the example shown here in FIG. 25.

Figure 26:
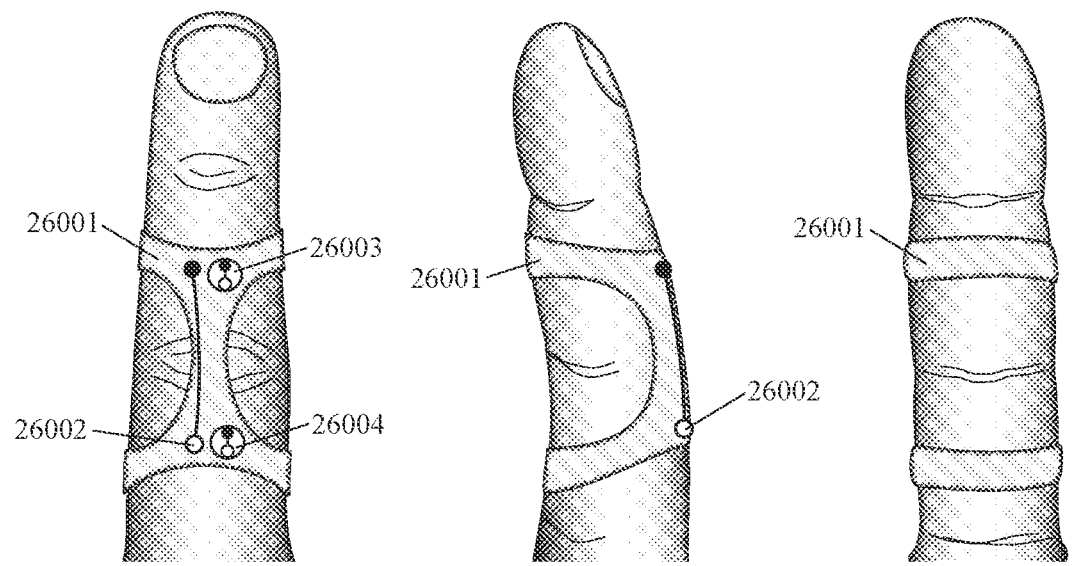
FIG. 26 shows a bi-loop arcuate member with a bend sensor and EMG sensors.

FIG. 26 shows another example of how this invention can be embodied in a wearable device for measuring finger motion and recognizing hand gestures. This example is similar to the one shown in FIG. 19 except that it has electromyographic (EMG) sensors in addition to a bend sensor for measuring the configuration and/or movement of an interphalangeal joint. The left third of FIG. 26 shows this device from a top-down perspective, looking at the upper (dorsal) surface of a person's finger. The middle third of FIG. 26 shows this same device from a side perspective, with the finger having been rotated 90 degrees clockwise. The right third of FIG. 26 shows this same device from a bottom-up perspective, looking at the lower (ventral) surface of the finger.

Specifically, FIG. 26 shows a wearable device for measuring finger motion and recognizing hand gestures comprising: (a) a bi-loop arcuate member 26001, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the dorsal surface of the proximal interphalangeal joint of the finger, wherein the joint-spanning strip spans from the distal loop to the proximal loop, and wherein the joint-spanning strip bends when the proximal interphalangeal joint bends; (b) a bend sensor 26002, wherein this bend sensor is part of, or attached to the flexible joint-spanning strip, wherein the bend sensor is configured to span at least a portion of the proximal interphalangeal joint, and wherein changes in energy transmitted through and/or generated by the bend sensor are used to measure the motion and/or configuration of the proximal interphalangeal joint; (c) a distal electromyographic (EMG) sensor 26003 which is part of, or attached to, the flexible joint-spanning strip at a location which is configured to be distal to the proximal interphalangeal joint of the finger; and (d) a proximal electromyographic (EMG) sensor 26004 which is part of, or attached to, the flexible joint-spanning strip at a location which is configured to be proximal to the proximal interphalangeal joint of the finger.

The bi-loop arcuate member herein can be configured as described previously in the narrative which accompanies FIG. 19. An electromyographic (EMG) sensor can be selected and configured as described previously in the narrative which accompanies FIG. 5. A bend sensor herein can be selected and configured as described previously in the narrative which accompanies FIG. 19. Other relevant design variations discussed with respect to other examples in this description can also apply to the example shown here in FIG. 26.

Figure 27:
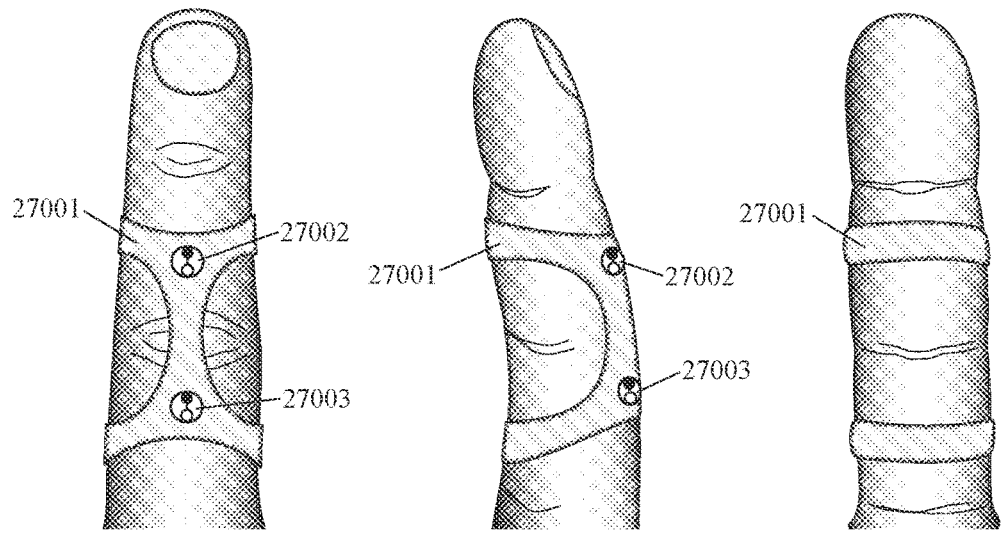
FIG. 27 shows a bi-loop arcuate member with two EMG sensors.

FIG. 27 shows another example of how this invention can be embodied in a wearable device for measuring finger motion and recognizing hand gestures. This example is similar to the one shown in FIG. 19 except that it has electromyographic (EMG) sensors instead of a bend sensor for measuring the configuration and/or movement of an interphalangeal joint. The left third of FIG. 27 shows this device from a top-down perspective, looking at the upper (dorsal) surface of a person's finger. The middle third of FIG. 27 shows this same device from a side perspective, with the finger having been rotated 90 degrees clockwise. The right third of FIG. 27 shows this same device from a bottom-up perspective, looking at the lower (ventral) surface of the finger.

Specifically, FIG. 27 shows a wearable device for measuring finger motion and recognizing hand gestures comprising: (a) a bi-loop arcuate member 27001, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the dorsal surface of the proximal interphalangeal joint of the finger, wherein the joint-spanning strip spans from the distal loop to the proximal loop, and wherein the joint-spanning strip bends when the proximal interphalangeal joint bends; (b) a distal electromyographic (EMG) sensor 27003 which is part of, or attached to, the flexible joint-spanning strip at a location which is configured to be distal to the proximal interphalangeal joint of the finger; and (c) a proximal electromyographic (EMG) sensor 27004 which is part of, or attached to, the flexible joint-spanning strip at a location which is configured to be proximal to the proximal interphalangeal joint of the finger.

The bi-loop arcuate member herein can be configured as described previously in the narrative which accompanies FIG. 19. An electromyographic (EMG) sensor can be selected and configured as described previously in the narrative which accompanies FIG. 5. Other relevant design variations discussed with respect to other examples in this description can also apply to the example shown here in FIG. 27.

Figure 28:
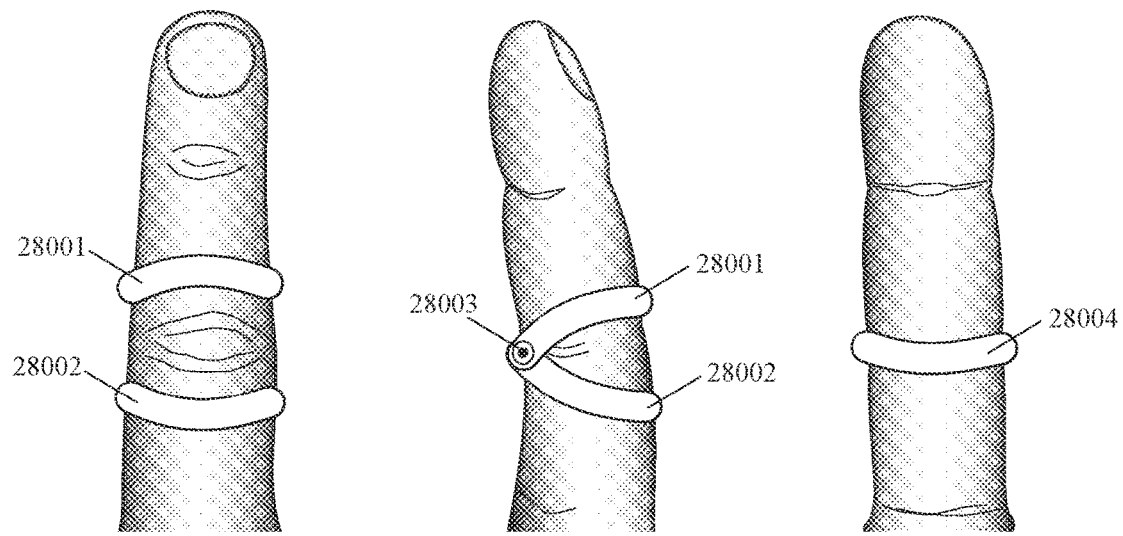
FIG. 28 shows a first device with two connected pivoting finger loops.

FIG. 28 shows another example of how this invention can be embodied in a wearable device for measuring finger motion and recognizing hand gestures. The left third of FIG. 28 shows this device from a top-down perspective, looking at the upper (dorsal) surface of a person's finger. The middle third of FIG. 28 shows this same device from a side perspective, with the finger having been rotated 90 degrees clockwise. The right third of FIG. 28 shows this same device from a bottom-up perspective, looking at the lower (ventral) surface of the finger.

Specifically, FIG. 28 shows a wearable device for measuring finger motion and recognizing hand gestures comprising: (a) a distal finger loop 28001 which is configured to cross the dorsal surface of a person's finger at a location which is distal to the proximal interphalangeal joint; (b) a proximal finger loop 28002 which is configured to cross the dorsal surface of a person's finger at a location which is proximal to the proximal interphalangeal joint; and (c) a movable connector 28003 between a ventral portion of the distal finger loop and a ventral portion of the proximal finger loop, wherein a dorsal portion of the distal finger loop and a dorsal portion of the proximal finger loop pivot on the movable connector away from each other when the proximal interphalangeal joint bends, and wherein pivoting of the distal and proximal finger loops is measured and used to measure finger motion and/or configuration.

In an example, a finger loop can be a partially-circumferential finger ring. In an example, a finger loop can span a portion of the circumference of a finger. In an example, a finger loop can span between 60% and 95% of the circumference of a finger. In an example, a finger loop can be made from metal or a polymer. In an example a finger loop can have a shape which is a section of a circle, torus, or cylinder. In an example a finger loop can have a shape which comprises 60-95% of the circumference of a circle, torus, or cylinder.

In an example, a movable connector between a distal finger loop and a proximal finger loop can be an axle, a hinge, and/or a wheel. In an example the ventral portions of distal and proximal finger loops can be connected by an axle, a hinge, and/or a wheel which allows their dorsal portions to pivot relative to each other. In an example, a movable connector between a distal finger loop and a proximal finger loop can be a rotating member. In an example, the ventral portions of distal and proximal finger loops can be connected by a rotating member which allows their dorsal portions to pivot relative to each other. In an example, a movable connector between a distal finger loop and a proximal finger loop can be a folding and/or pleated (e.g. accordion style) member. In an example, finger loops can be connected by a folding and/or pleated (e.g. accordion style) member which allows them to pivot relative to each other. In an example, a movable connector between a distal finger loop and a proximal finger loop can be an elastic and/or expanding member. In an example, finger loops can be connected by an elastic and/or expanding member which allows them to pivot relative to each other.

In an example, a distal finger loop can have a first cross-sectional plane and a proximal finger loop can have a second cross-sectional plane. In an example, a ventral portion of the first cross-sectional plane is closer to a ventral portion of the second cross-sectional plane than a distal portion of the first cross-sectional plane is to a distal portion of the second cross-sectional plane. In an example, the first cross-sectional plane intersects the second cross-sectional plan (or the extension thereof in three-dimensional space). In an example, the plane intersection angle can be defined as the (dorsal-facing angle) formed by the intersection of the first cross-sectional plane and the second cross-sectional plane (or the extension thereof in three-dimensional space). In an example, the plane intersection angle (or a function thereof) can be used to estimate the angle of the proximal interphalangeal joint. In an example, the plane intersection angle can be within a range of 10-90 degrees when the proximal interphalangeal joint is fully extended. In an example, the plane intersection angle can be within a range of 90-180 degrees when the proximal interphalangeal joint is fully extended. In an example, the plane intersection angle can be within a range of 10-180 degrees as the interphalangeal joint extends and contracts. In an example, changes in the plane intersection angle can be used to measure finger motion and recognize hand gestures.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 28.

Figure 29:
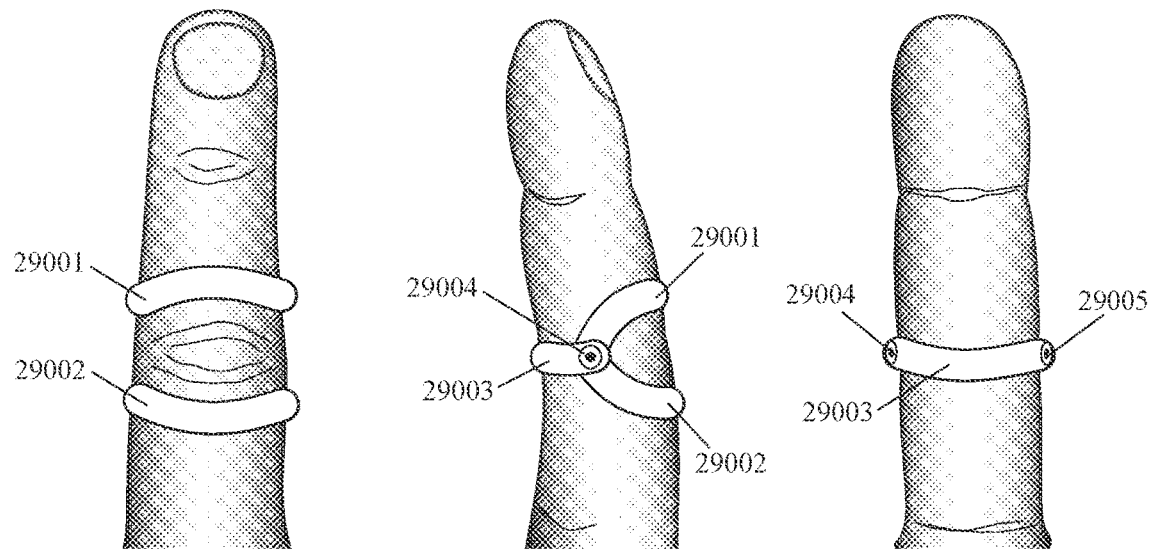
FIG. 29 shows a second device with two connected pivoting finger loops.

FIG. 29 shows another example of how this invention can be embodied in a wearable device for measuring finger motion and recognizing hand gestures. The left third of FIG. 29 shows this device from a top-down perspective, looking at the upper (dorsal) surface of a person's finger. The middle third of FIG. 29 shows this same device from a side perspective, with the finger having been rotated 90 degrees clockwise. The right third of FIG. 29 shows this same device from a bottom-up perspective, looking at the lower (ventral) surface of the finger.

Specifically, FIG. 29 shows a wearable device for measuring finger motion and recognizing hand gestures comprising: (a) a distal dorsal loop 29001 which is configured to cross the dorsal surface of a person's finger at a location which is distal to the proximal interphalangeal joint; (b) a proximal dorsal loop 29002 which is configured to cross the dorsal surface of a person's finger at a location which is proximal to the proximal interphalangeal joint; (c) a ventral loop 29003 which is configured to cross the ventral surface of a person's finger; and (d) a movable connector 29003 between the distal dorsal loop, the proximal dorsal loop, and the ventral loop, wherein the distal dorsal loop and the proximal dorsal loop pivot on the movable connector when the proximal interphalangeal joint bends, and wherein pivoting of the distal and proximal dorsal loops is measured and used to measure finger motion and/or configuration.

In an example, a dorsal loop can be a partially-circumferential finger ring. In an example, a dorsal loop can span a portion of the circumference of a finger. In an example, a dorsal loop can span between 25% and 75% of the circumference of a finger. In an example, a dorsal loop can be made from metal or a polymer.

In an example, a movable connector between a distal dorsal loop and a proximal dorsal loop can be an axle, a hinge, and/or a wheel. In an example, distal and proximal dorsal loops can be connected by an axle, a hinge, and/or a wheel which allows their dorsal portions to pivot relative to each other. In an example, a movable connector between a distal dorsal loop and a proximal dorsal loop can be a rotating member. In an example, distal and proximal dorsal loops can be connected by a rotating member which allows their dorsal portions to pivot relative to each other. In an example, a movable connector between a distal dorsal loop and a proximal dorsal loop can be a folding and/or pleated (e.g. accordion style) member. In an example, distal and proximal dorsal loops can be connected by a folding and/or pleated (e.g. accordion style) member which allows their dorsal portions to pivot relative to each other. In an example, a movable connector between a distal dorsal loop and a proximal dorsal loop can be an elastic and/or expanding member. In an example, distal and proximal dorsal loops can be connected by an elastic and/or expanding member which allows their dorsal portions to pivot relative to each other.

In an example, a distal dorsal loop can have a first cross-sectional plane and a proximal dorsal loop can have a second cross-sectional plane. In an example, a plane intersection angle can be defined as the (dorsal-facing) angle formed by the intersection of the first cross-sectional plane and the second cross-sectional plane (or the extension thereof in three-dimensional space). In an example, the plane intersection angle (or a function thereof) can be used to estimate the angle of the proximal interphalangeal joint. In an example, the plane intersection angle can be within a range of 10-90 degrees when the proximal interphalangeal joint is fully extended. In an example, the plane intersection angle can be within a range of 90-180 degrees when the proximal interphalangeal joint is fully extended. In an example, the plane intersection angle can be within a range of 10-180 degrees as the interphalangeal joint extends and contracts. In an example, changes in the plane intersection angle can be used to measure finger motion and recognize hand gestures.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 29.

Figure 30:
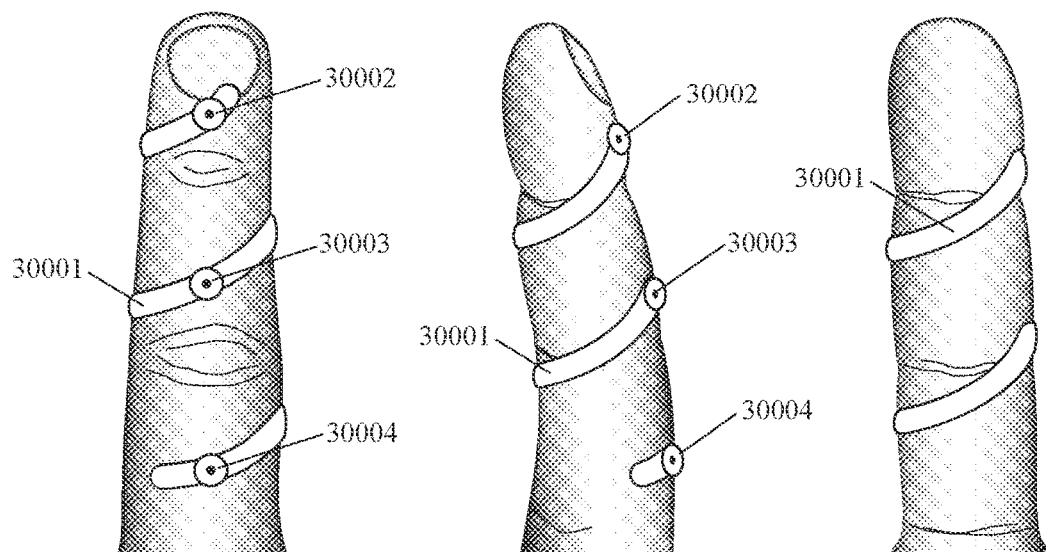
FIG. 30 shows a finger-worn helix with inertial motion sensors.

FIG. 30 shows another example of how this invention can be embodied in a wearable device for measuring finger motion and recognizing hand gestures. The left third of FIG. 30 shows this device from a top-down perspective, looking at the upper (dorsal) surface of a person's finger. The middle third of FIG. 30 shows this same device from a side perspective, with the finger having been rotated 90 degrees clockwise. The right third of FIG. 30 shows this same device from a bottom-up perspective, looking at the lower (ventral) surface of the finger. Specifically, FIG. 30 shows a wearable device for measuring finger motion and recognizing hand gestures comprising: a helical member (30001) which is configured to wind around a person's finger and span at least one interphalangeal joint; and two or more inertial motion sensors (30002, 30003, and 30004) which are part or, or attached to, the helical member.

In an example, this device can comprise a single helical member. In an example, this device can comprise two helical members. In an example, two helical members can comprise a first helix and second symmetrically-reflected helix. In an example, two helical members can comprise a double (parallel) helix. In an example, a helical member can be a spiral that winds around a person's finger. In an example, the ends of a helical member can be rounded disks. In an example, the ends of a helical member can be circular portions around the circumference of the finger. In an example, this device can further comprise two finger rings, one ring connected to the distal end of the helical member and one ring connected to the proximal end of the helical member.

In an example, the spiraling loop of a helical member can be a metal or polymer spring. In an example, the spiraling loop of a helical member can have a circular cross-section. In an example, the spiraling loop of a helical member can have a resilient metal core and a soft exterior. In an example, the spiraling loop of a helical member can be relatively flat and the helical member can be like a spiraling ribbon. In an example, there can be longitudinal variation in the diameter of the spiraling loops of a helical member. In an example, a helical member can be tapered, with a smaller-diameter spiral loop around the distal phalanx and a larger-diameter spiral loop around the proximal phalanx.

In an example, a helical member can longitudinally slide over a finger tip onto a finger. In an example, a helical member can be sufficiently-flexible to slide over a finger tip onto a finger, but also be sufficiently-resilient to stay on the finger unless intentionally removed. In an example, a helical member can be slid over a finger tip onto a finger and then attached to the finger nail. In an example, a helical member can be slid over a finger tip onto a finger and then tightened by a twisting motion so that it fits snugly on the finger. In an example, a helical member can be sufficiently-flexible to not restrict finger motion, but also be sufficiently-resilient to stay on the finger unless intentionally removed.

In an example, a helical member can make two loops around a finger and/or encircle a finger two times. In an example, a helical member can make three loops around a finger and/or encircle a finger three times. In an example, a helical member can make between 2-3 loops around a finger and/or encircle a finger between 2-3 times. In an example, a helical member can make more than three loops around a finger and/or encircle a finger more than three times. In an example, a helical member can span a finger from the distal phalanx to the proximal phalanx. In an example, a first loop of a helical member can span the distal interphalangeal joint of a finger and a second loop can span the proximal interphalangeal joint of the finger. In an example, first and second loops of a helical member can span the dorsal surface of a finger across the middle portions of the intermediate phalanx and the proximal phalanx, respectively. In an example, the distal and proximal ends of a helical member can be on the dorsal surface of a finger. In an example, the distal end of a helical member can be (removably) attached to a finger nail.

In an example, an inertial motion sensor can be selected from the group consisting of: multi-axial accelerometer, gyroscope, and inclinometer. In an example, inertial motion sensors can be part of, or attached to, a helical member at dorsal locations along the helical member. In an example, there can be an inertial motion sensor on the dorsal portion of each loop of the helical member. In an example, there can be one inertial motion sensor for each phalanx spanned by the helical member. In an example, there can be three inertial motion sensors, one located on the dorsal surface of each phalanx of the finger. In an example, there can be two inertial motion sensors for measuring the motion of an interphalangeal joint, one sensor located distal to the joint and one sensor located proximal to the joint.

In an example, differences in the motion of a first inertial motion sensor versus the motion of a second inertial motion sensor can be analyzed in order to estimate the bending motion of a proximal interphalangeal joint and/or a distal interphalangeal joint. In an example, similarities in the motions of a first inertial motion sensor and a second inertial motion sensor can be analyzed in order to estimate the overall motion of (the centroid of) a person's finger. In an example, differences in the three-dimensional angular orientations or configurations of a first inertial motion sensor versus a second inertial motion sensor can be analyzed in order to estimate the bend angle of an interphalangeal joint and to recognize finger configuration.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, differences in the motion of inertial motion sensors on a first finger versus inertial motion sensors on a second finger can be analyzed in order to estimate the bending motion of meta-carpophalageal joints. In an example, similarities in the motions of inertial motion sensors on a first finger and inertial motion sensors on a second finger can be analyzed in order to estimate the overall motion of (the centroid of) a person's hand. In an example, differences in the three-dimensional angular orientations of inertial motion sensors on a first finger versus inertial motion sensors on a second finger can be analyzed in order to estimate the bend angles of meta-carpophalageal joints and to recognize hand configuration.

In an example, hand gestures can be recognized based on one or more factors selected from the group consisting of: movement directions and speeds for the motion sensors; roll, pitch, and yaw of the motion sensors; three-dimensional orientations of motion sensors; estimated joint angles for the distal interphalangeal, intermediate interphalangeal, and meta-carpophalageal joints; estimated roll, pitch, and yaw of the hand centroid; estimated three-dimensional orientation the hand centroid; modeled three-dimensional configuration of the distal, intermediate, and proximal phalanges; and three-dimensional orientations of the distal, intermediate, and proximal phalanges.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 30.

Figure 31:
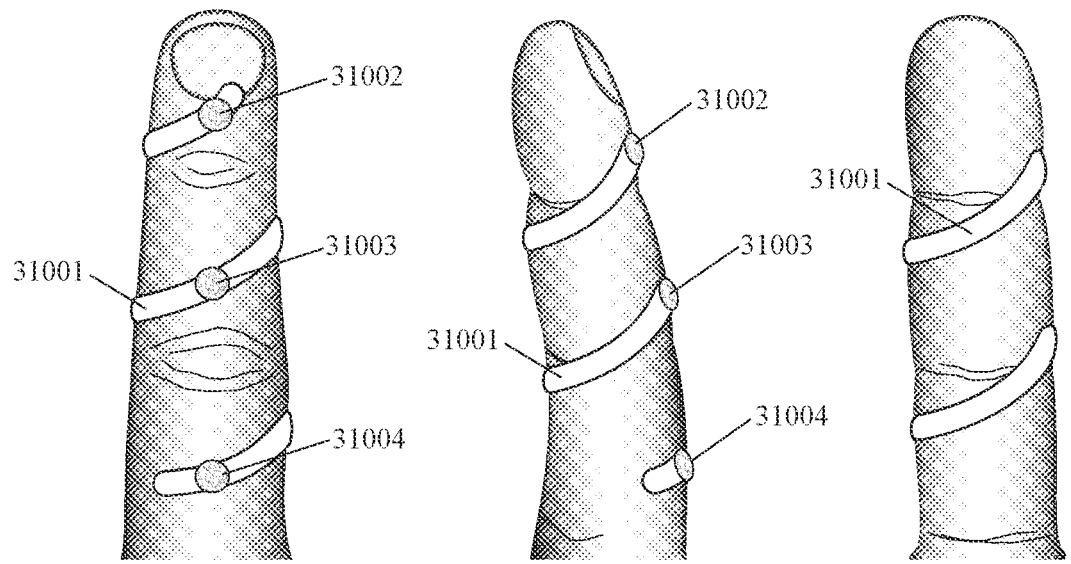
FIG. 31 shows a finger-worn helix with light reflectors.

FIG. 31 shows another example of how this invention can be embodied in a wearable device for measuring finger motion and recognizing hand gestures. The left third of FIG. 31 shows this device from a top-down perspective, looking at the upper (dorsal) surface of a person's finger. The middle third of FIG. 31 shows this same device from a side perspective, with the finger having been rotated 90 degrees clockwise. The right third of FIG. 31 shows this same device from a bottom-up perspective, looking at the lower (ventral) surface of the finger. Specifically, FIG. 31 shows a wearable device for measuring finger motion and recognizing hand gestures comprising: a helical member (31001) which is configured to wind around a person's finger and span at least one interphalangeal joint; and two or more light-energy reflectors (31002, 31003, and 31004) which are part or, or attached to, the helical member.

In an example, this device comprises a single helical member. In an example, a device can comprise two or more helical members. In an example, a device can comprise a first helix and second helix which is reflected around the longitudinal axis of the first helix. In an example, a device can comprise a double helix (similar to a DNA strand). In an example, the ends of a helical member can be rounded disks. In an example, the ends of a helical member can be circular rings around the circumference of the finger. In an example, the spiral of a helical member can be made from a metal or a polymer. In an example, this spiral loop can have a circular or elliptical cross-sectional shape. In an example, this spiral loop can comprise a resilient metal core with a soft coating. In an example, this spiral loop can be relatively flat, like a spiral ribbon around a finger. In an example, a helical member can be tapered to better fit a finger. In an example, the diameter of a loop around a distal phalanx can be smaller than the diameter of a loop around a proximal phalanx.

In an example, a helical member can slide longitudinally over a finger tip onto a finger. In an example, a helical member can be flexible so that it can be diagonally expanded in order to slide onto a finger, but can be resilient so that it contracts to stay on the finger. In an example, the diameter of a helical member can be expanded to slide it onto (or off from) a finger by twisting the helix in a first direction and the diameter of the helical member can be contracted to hold it onto a finger by twisting the helix in a second direction. In an example, the first direction can be clockwise and the second direction can be counter-clockwise, or vice versa. In an example, a helical member can be attached to a finger nail once it is on a finger.

In an example, a helical member can loop two times around a finger. In an example, a helical member can loop three times around a finger. In an example, a helical member can loop between two and three times around a finger. In an example, a helical member can loop more than three times around a finger. In an example, a helical member can span from a distal phalanx to a proximal phalanx. In an example, a first spiral loop of a helical member can span a distal interphalangeal joint and a second spiral loop can span a proximal interphalangeal joint. In an example, a first spiral loop can span the dorsal surface of a finger across the intermediate phalanx and a second spiral loop can span the dorsal surface of a finger across the proximal phalanx. In an example, a first spiral loop can span the ventral surface of a finger across the intermediate phalanx and a second spiral loop can span the ventral surface of a finger across the proximal phalanx. In an example, the distal and proximal ends of a helical member can be on the dorsal surface of a finger. In an example, the distal and proximal ends of a helical member can be on the ventral surface of a finger.

In an example, a light-energy reflector can have an outer surface which reflects light energy from an external source. In an example, an external light source can be an environmental light source, such as the sun or nearby artificial lighting. In an example, an external light source can be part of a separate wearable device. In an example, a light source can be a source of infrared or near-infrared light source. In an example, a light source can be a source of polarized or coherent light.

In an example, a light-energy reflector can have a unique reflective color, wavelength, spectrum, polarization, light pattern, and/or shape. This can help to differentiate one light-energy reflector from another and/or to uniquely identify a specific light-energy reflector. In an example, this device can be part of an overall system for measuring finger motion and recognizing gestures which further comprises a camera. In an example, a camera can track the locations of light-energy reflectors worn on fingers in order to model the configurations and/or motions of those fingers. In an example, a camera of such a system can be incorporated into smart glasses or other electronically-functional eyewear. In an example, a camera of such a system can be incorporated into an EEG monitor, a hat, cap, or visor, a smart necklace, a wearable button, and/or an upper body garment. In an example, analysis of images captured by a camera can identify the locations of light-energy reflectors based on their unique reflective colors, wavelengths, spectrums, polarizations, light patterns, and/or shapes.

In the example shown in FIG. 31, light-energy members are passive light-energy reflectors. In an alternative example, light-energy members can be active light-energy emitters, such as LEDs. In an example, the locations of one or more active light-energy emitters (such as LEDs) can be tracked by analysis of camera images. In an example, a camera can be part of smart glasses or other electronically-functional eyewear. In an example, a specific light-energy emitter can emit light with a unique color, wavelength, polarization, or pattern which enables it to be differentiated from other light-energy emitters in a finger-worn device or in a system of finger-worn devices.

In an example, this device can be part of an overall system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, differences in the motion of a first light-energy reflector versus the motion of a second light-energy reflector can be analyzed in order to estimate the bending motion of a proximal interphalangeal joint and/or a distal interphalangeal joint. In an example, similarities in the motions of a first light-energy reflector and a second light-energy reflector can be analyzed in order to estimate the overall motion of (the centroid of) a person's finger. In an example, differences in the angular orientations of a first light-energy reflector versus a second light-energy reflector can be analyzed in order to estimate the bend angle of a proximal interphalangeal joint and to recognize finger configuration.

The example shown in FIG. 31 can be part of an overall system for measuring finger motion and recognizing gestures comprising: a plurality of helical members worn on fingers; a plurality of light-energy reflectors which are part of these helical members; electronically-functional eyewear; and a camera which is part of the eyewear, wherein analysis of camera images is used to identify the locations of the light-energy reflectors and to recognize hand gestures based on the relative locations of the light-energy reflectors. In an example, each of the light-energy reflectors can have a unique color, wavelength, spectrum, polarization, pattern, or shape which is identified in the images captured by the camera. In an example, this system can function as a gesture-based human-to-computer interface.

In an example, differences in the motion of light-energy reflectors on a first finger versus light-energy reflectors on a second finger can be analyzed in order to estimate the bending motion of meta-carpophalageal joints. In an example, similarities in the motions of light-energy reflectors on a first finger and light-energy reflectors on a second finger can be analyzed in order to estimate the overall motion of (the centroid of) a person's hand. In an example, data from multiple light-energy reflectors on multiple fingers can be received and analyzed by a data processing unit in order to recognize hand gestures. In an example, this data processing unit can be part of a helical member. In an example, this data processing unit can be part of a separate wearable or handheld device with which helical members are in wireless communication.

In an example, a helical member can further comprise one or more components selected from the group consisting of: power source; energy transducer; data processing unit; wireless data transmitter; wireless data receiver; computer-to-human interface; microphone; and camera. In an example, a power source can be a battery. In an example, an energy transducer can generate electricity from body motion. In an example, a wireless data transmitter or wireless data receiver can be in electronic communication with a separate wearable or handheld electronic device. In an example, a computer-to-human interface can be a visual interface. In an example, a computer-to-human interface can be selected from the group consisting of: computer display screen; plurality of light-emitting diodes; image projector; vibrator or other tactile-sensation-creating actuator; and sound-emitting speaker.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 31.

Figure 32:
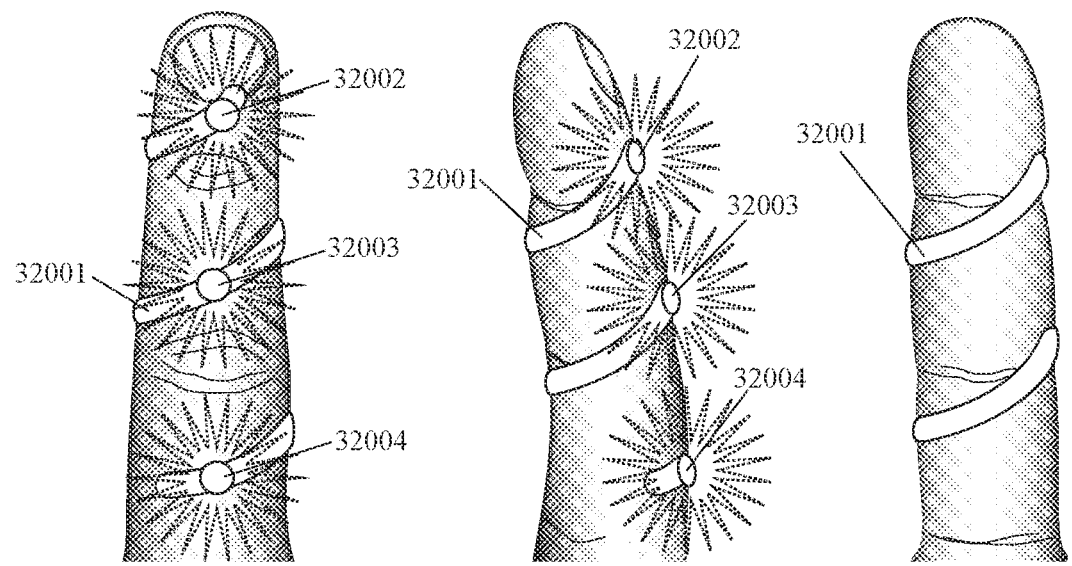
FIG. 32 shows a finger-worn helix with light emitters.

FIG. 32 shows another example of how this invention can be embodied in a wearable device for measuring finger motion and recognizing hand gestures. This example is similar to the one just shown in FIG. 31, except that this example has active light-energy emitters (such as LEDs) instead of passive light-energy reflectors. The left third of FIG. 32 shows this device from a top-down perspective, looking at the upper (dorsal) surface of a person's finger. The middle third of FIG. 32 shows this same device from a side perspective, with the finger having been rotated 90 degrees clockwise. The right third of FIG. 32 shows this same device from a bottom-up perspective, looking at the lower (ventral) surface of the finger. Specifically, FIG. 32 shows a wearable device for measuring finger motion and recognizing hand gestures comprising: a helical member (32001) which is configured to wind around a person's finger and span at least one interphalangeal joint; and two or more light-energy emitters (32002, 32003, and 32004) which are part or, or attached to, the helical member. Other relevant design variations discussed with respect to other examples in this description can also apply to the example shown here in FIG. 32.

Figure 33:
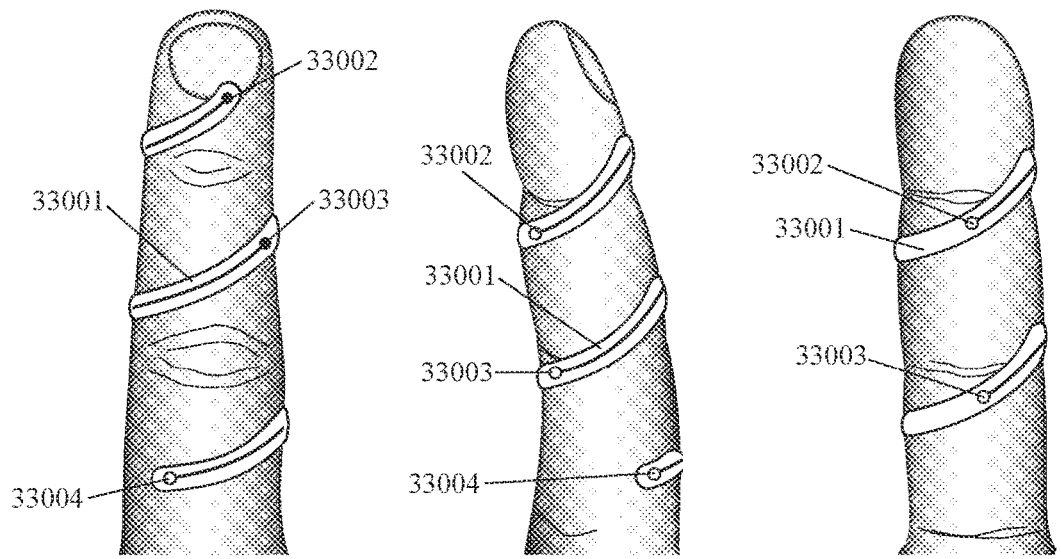
FIG. 33 shows a finger-worn helix with bend sensors.

FIG. 33 shows another example of how this invention can be embodied in a wearable device for measuring finger motion and recognizing hand gestures. This example is similar to the one shown in FIG. 30, except that this example has bend sensors instead of inertial motion sensors. The left third of FIG. 33 shows this device from a top-down perspective, looking at the upper (dorsal) surface of a person's finger. The middle third of FIG. 33 shows this same device from a side perspective, with the finger having been rotated 90 degrees clockwise. The right third of FIG. 33 shows this same device from a bottom-up perspective, looking at the lower (ventral) surface of the finger.

Specifically, FIG. 33 shows a wearable device for measuring finger motion and recognizing hand gestures comprising: a helical member (33001) which is configured to wind around a person's finger and span at least one interphalangeal joint; and two or more bend sensors (33002, 33003, and 33004) which are part or, or attached to, the helical member. A helical member herein can be selected and configured as described previously in the narrative which accompanies FIG. 30. A bend sensor herein can be selected and configured as described previously in the narrative which accompanies FIG. 19. Other relevant design variations discussed with respect to other examples in this description can also apply to the example shown here in FIG. 33.

Figure 34:
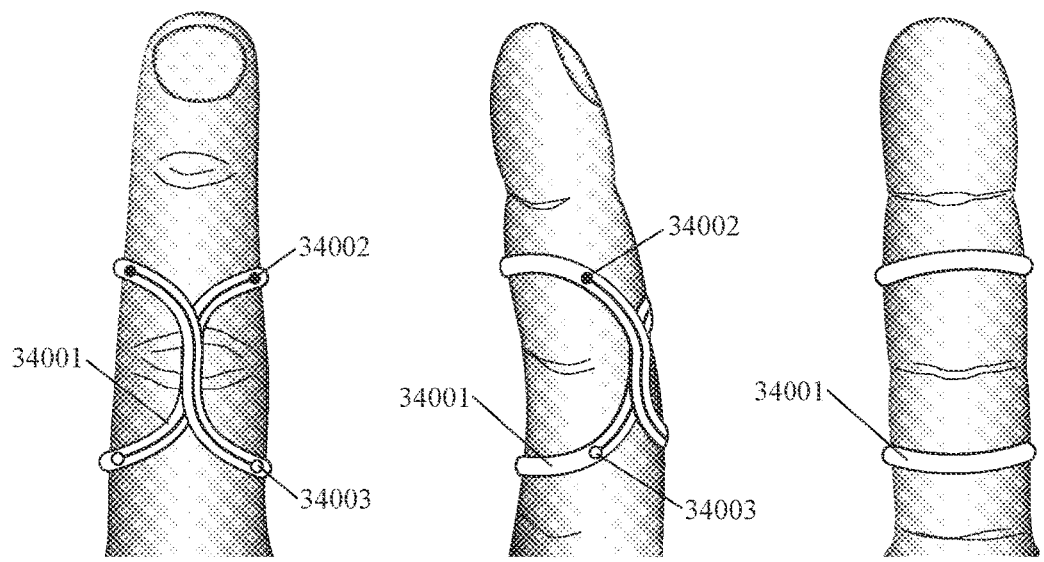
FIG. 34 shows a finger-worn overlapping loop member with bend sensors.

FIG. 34 shows another example of how this invention can be embodied in a wearable device for measuring finger motion and recognizing hand gestures. The left third of FIG. 34 shows this device from a top-down perspective, looking at the upper (dorsal) surface of a person's finger. The middle third of FIG. 34 shows this same device from a side perspective, with the finger having been rotated 90 degrees clockwise. The right third of FIG. 34 shows this same device from a bottom-up perspective, looking at the lower (ventral) surface of the finger.

Specifically, FIG. 34 shows a wearable device for measuring finger motion and recognizing hand gestures comprising: an overlapping-loop member (34001), wherein the overlapping-loop member further comprises a distal loop which is configured to loop around a finger at a first location which is distal to an interphalangeal joint, wherein the overlapping-loop member further comprises a proximal loop which is configured to loop around the finger at a second location which is proximal to the interphalangeal joint, wherein the loop of the overlapping-loop member overlaps itself between the distal loop and the proximal loop; and two or more bend sensors (34002 and 34003) which are part or, or attached to, the overlapping loop member.

In an example, the loop of an overlapping-loop member can overlap itself on the dorsal surface of a finger. In an example, the loop of an overlapping-loop member can overlap itself on the dorsal surface of the finger at the proximal interphalangeal joint. In an example, the loop of an overlapping-loop member can overlap itself on the ventral surface of a finger. In an example, the loop of an overlapping-loop member can overlap itself on the finger at the proximal interphalangeal joint. In an example, an overlapping-loop member can be made from elastic, stretchable, and/or expanding material. In an example, the diameters of distal and proximal loops can be stretched and/or expanded in order to slide an overlapping-loop member onto (or off from) a finger. In an example, the loop of an overlapping-loop member can be attached to itself where it overlaps itself.

In an example, a bend sensor can be selected and configured as described previously in the narrative which accompanies FIG. 19. In an example, a bend sensor can span an interphalangeal joint. In an example, a bend sensor can span from a distal loop to a proximal loop. In an example, this device can have two bend sensors, each spanning from a distal loop to a proximal loop, wherein these two bend sensors overlap where the loop of the overlapping-loop member overlaps. Other relevant design variations discussed with respect to other examples in this description can also apply to the example shown here in FIG. 34.

Figure 35:
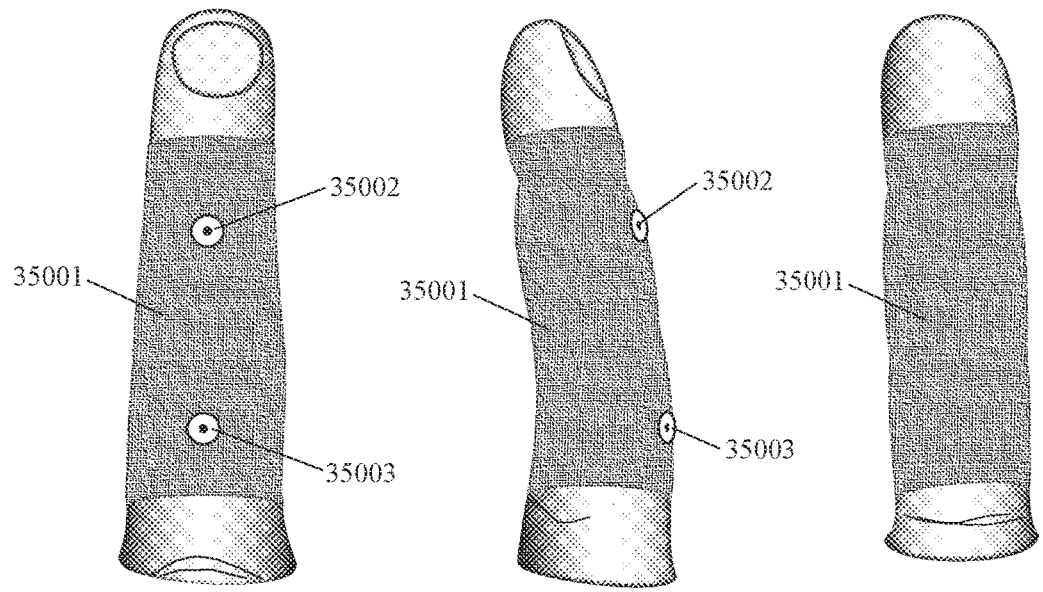
FIG. 35 shows a finger sleeve with inertial motion sensors.

FIG. 35 shows another example of how this invention can be embodied in a wearable device for measuring finger motion and recognizing hand gestures. The left third of FIG. 35 shows this device from a top-down perspective, looking at the upper (dorsal) surface of a person's finger. The middle third of FIG. 35 shows this same device from a side perspective, with the finger having been rotated 90 degrees clockwise. The right third of FIG. 35 shows this same device from a bottom-up perspective, looking at the lower (ventral) surface of the finger.

Specifically, FIG. 35 shows a wearable device for measuring finger motion and recognizing hand gestures comprising: a finger sleeve (35001) which is configured to be worn around a person's finger and to span at least one interphalangeal joint; a first inertial motion sensor (35002) which is part or, or attached to, the finger sleeve at a location which is distal to the interphalangeal joint; and a second inertial motion sensor (35003) which is part or, or attached to, the finger sleeve at a location which is proximal to the interphalangeal joint.

In an example, a finger sleeve can be elastic, stretchable, and/or expandable. In an example, a finger sleeve can be made from elastic, stretchable, and/or expandable fabric. In an example, a finger sleeve can be made from one or more materials selected from the group consisting of: Acetate, Acrylic, Cotton, Denim, Elastane, Latex, Linen, Lycra®, Neoprene, Nylon, Polyester, Rayon, Silk, Spandex®, and Wool. In an example, a finger sleeve can be made with a plain weave, rib weave, basket weave, twill weave, satin weave, leno weave, or mock leno weave. In an example, a finger sleeve can be made with a weave which is gas permeable so that the finger sleeve can "breath". In an example, a finger sleeve can be made with: bendable fibers, threads, or yarns; elastic fibers, threads, or yarns; electroconductive fibers, threads, or yarns; plaited fibers, threads, or yarns; sinusoidal fibers, threads, or yarns; stretchable fibers, threads, or yarns; variable-resistance electroconductive fiber, thread, or yarn; and/or water-resistant fibers, threads, or yarns.

In an example, a finger sleeve can be configured to fit on a finger in a particular location and/or with a particular orientation in order to optimally measure finger motion and recognize hand gestures. In an example, a finger sleeve can fit closely on a finger so that it does not shift over a person's skin when a finger moves. In an example, a finger sleeve can have markings (or structural features) which are to be aligned with a particular anatomical feature. In an example, a finger sleeve can have markings (or structural features) which should align with (the dorsal surface of a finger over) an interphalangeal joint or a finger nail. In an example, a finger sleeve for a specific finger can have a specific color, visual pattern, or code. In an example, different finger sleeves for different fingers can have different colors, visual patterns, or codes. In an example, some or all of a finger sleeve can be transparent or translucent. In an example, the portions of a finger sleeve which span the dorsal surface of a finger can be transparent or translucent.

In an example, a finger sleeve can comprise a continuous loop or cylinder. In an example, a finger sleeve can have a generally-circular interior cross-section when it is slid onto a finger and can have a collapsed (relatively flat) interior cross-section when it is removed from a finger. In an example, a finger sleeve can be attached to a finger by longitudinally sliding the sleeve over a finger tip. In an alternative example, a finger sleeve can comprise a discontinuous loop or cylinder with sides which are attached in order to fasten it to a finger. In an example, a finger sleeve can be attached to a finger by curving the sides of the sleeve around the circumference of a finger and then fastening the sides together with an attachment mechanism selected from the group consisting of: hook-and-eye, buckle, clip, prong, clasp, hook, pin, button, plug, protrusion-and-eye, snap, zipper, and magnet. In an example, a finger sleeve can have an open distal end. In an example, a finger sleeve can have a closed distal end (which fits over a finger tip).

In an example, a finger sleeve can be configured to longitudinally span from a distal phalanx to a proximal phalanx of a finger. In an example, a finger sleeve can be configured to longitudinally span from an intermediate phalanx to a proximal phalanx of a finger. In an example, a finger sleeve can have a length in the range of 1-4 inches. In an example, a finger sleeve can have a length in the range of 1.5-3 inches. In an example, the diameter of a finger sleeve can be stretched and/or expanded so that the finger sleeve can be slipped over a finger tip onto a finger. In an example, a finger sleeve can have a shape which is cylindrical. In an example, a finger sleeve can have a shape which is a longitudinally-tapered cylinder, with a distal diameter which is smaller than a proximal diameter. In an example, the diameter of the distal end of a finger sleeve can be 5%-30% smaller than the diameter of the proximal end of a finger sleeve.

In an example, a finger sleeve can have longitudinal variation in elasticity. In an example, the portions of a finger sleeve which span one or more interphalangeal joints can be more elastic than other portions of the finger sleeve. In an example, a finger sleeve can have a distal portion with a first elasticity level which spans a distal phalanx, an intermediate portion with a second elasticity level which spans an intermediate phalanx, and a proximal portion with a third elasticity level which spans a proximal phalanx. In an example, the second elasticity level can be greater than the first elasticity level. In an example, the third elasticity level can be greater than the second elasticity level. In an example, a finger sleeve can have circumferential variation in elasticity. In an example, the portions of a finger sleeve which span the dorsal surface of a finger can be more elastic than the portions of a finger sleeve which span the ventral surface of a finger.

In an example, a finger sleeve can have longitudinal variation in type of fabric and/or fabric weave. In an example, a finger sleeve can have a first type of fabric and/or fabric weave for portions of the sleeve which span one or more joints and a second type of fabric and/or fabric weave for other portions of the sleeve. In an example, a finger sleeve can have circumferential variation in type of fabric and/or fabric weave. In an example, a finger sleeve can have a first type of fabric and/or fabric weave for portions of the sleeve which span the dorsal surface of a finger and a second type of fabric and/or fabric weave for portions of the sleeve which span the ventral surface of the finger.

In an example, a finger sleeve can have longitudinal variation in gas permeability level. In an example, a finger sleeve can have a first level of gas permeability for portions of the sleeve which span one or more joints and a second level of gas permeability for other portions of the sleeve. In an example, a finger sleeve can have circumferential variation in gas permeability level. In an example, a finger sleeve can have a first level of gas permeability for portions of the sleeve which span the dorsal surface of a finger and a second level of gas permeability for portions of the sleeve which span the ventral surface of the finger.

In an example, a finger sleeve can have longitudinal variation in electroconductive fibers. In an example, a finger sleeve can have a first level or pattern of electroconductive fibers in portions of the sleeve which span one or more joints and a second level or pattern of electroconductive fibers in other portions of the sleeve. In an example, a finger sleeve can have circumferential variation in electroconductive fibers. In an example, a finger sleeve can have a first level or pattern of electroconductive fibers in portions of the sleeve which span the dorsal surface of a finger and a second level or pattern of electroconductive fibers in portions of the sleeve which span the ventral surface of the finger.

In an example, an inertial motion sensor can be selected from the group consisting of: multi-axial accelerometer, gyroscope, and inclinometer. In an example, inertial motion sensors can be part of, or attached to, a finger sleeve at dorsal locations along the finger sleeve. In an example, there can be two inertial motion sensors for measuring the motion of an interphalangeal joint, one sensor located distal to the joint and one sensor located proximal to the joint. In an example, there can be one inertial motion sensor for each phalanx spanned by the finger sleeve. In an example, there can be three inertial motion sensors, one located on each phalanx of the finger.

In an example, differences in the motion of a first inertial motion sensor versus the motion of a second inertial motion sensor can be analyzed in order to estimate the bending motion of a proximal interphalangeal joint and/or a distal interphalangeal joint. In an example, similarities in the motions of a first inertial motion sensor and a second inertial motion sensor can be analyzed in order to estimate the overall motion of (the centroid of) a person's finger. In an example, differences in the three-dimensional angular orientations or configurations of a first inertial motion sensor versus a second inertial motion sensor can be analyzed in order to estimate the bend angle of an interphalangeal joint and to recognize finger configuration.

In an example, this device can be part of a system for measuring the motions and configurations of multiple fingers and for recognizing multi-finger hand gestures. In an example, there can be one such device on each of a person's fingers and thumb. In another example, such devices can be worn on only a subset of a person's fingers and thumb. In an example, one such device can be worn on a person's index finger and one such device can be worn on the person's thumb. In an example, such a device may be worn only on a person's index finger. In an example, such a device may be worn only on a person's ring finger.

In an example, differences in the motion of inertial motion sensors on a first finger versus inertial motion sensors on a second finger can be analyzed in order to estimate the bending motion of meta-carpophalageal joints. In an example, similarities in the motions of inertial motion sensors on a first finger and inertial motion sensors on a second finger can be analyzed in order to estimate the overall motion of (the centroid of) a person's hand. In an example, differences in the three-dimensional angular orientations of inertial motion sensors on a first finger versus inertial motion sensors on a second finger can be analyzed in order to estimate the bend angles of meta-carpophalageal joints and to recognize hand configuration.

In an example, hand gestures can be recognized based on one or more factors selected from the group consisting of: movement directions and speeds for the motion sensors; roll, pitch, and yaw of the motion sensors; three-dimensional orientations of motion sensors; estimated joint angles for the distal interphalangeal, intermediate interphalangeal, and meta-carpophalageal joints; estimated roll, pitch, and yaw of the hand centroid; estimated three-dimensional orientation the hand centroid; modeled three-dimensional configuration of the distal, intermediate, and proximal phalanges; and three-dimensional orientations of the distal, intermediate, and proximal phalanges.

In an example, one or more such finger-worn devices can be part of a system wherein finger-worn devices are in wireless communication with a separate wearable device. A separate wearable device can be selected from the group consisting of: wrist band, bracelet, or smart watch; arm band; smart necklace; smart glasses or other electronically-functional eyewear; ear wearable device; EEG-monitoring headband or other head-worn EEG device; smart belt or belt accessory; and smart shirt or other electronically-functional garment. In an example, this device can be part of a system wherein finger-worn devices are in wireless communication with a handheld computing device. A handhand computing device can be selected from the group consisting of: smart phone or other mobile phone; electronic pad or tablet, and other portable computer. Other relevant design variations discussed with respect to other examples in this description can also apply to the example shown here in FIG. 35.

Figure 36:
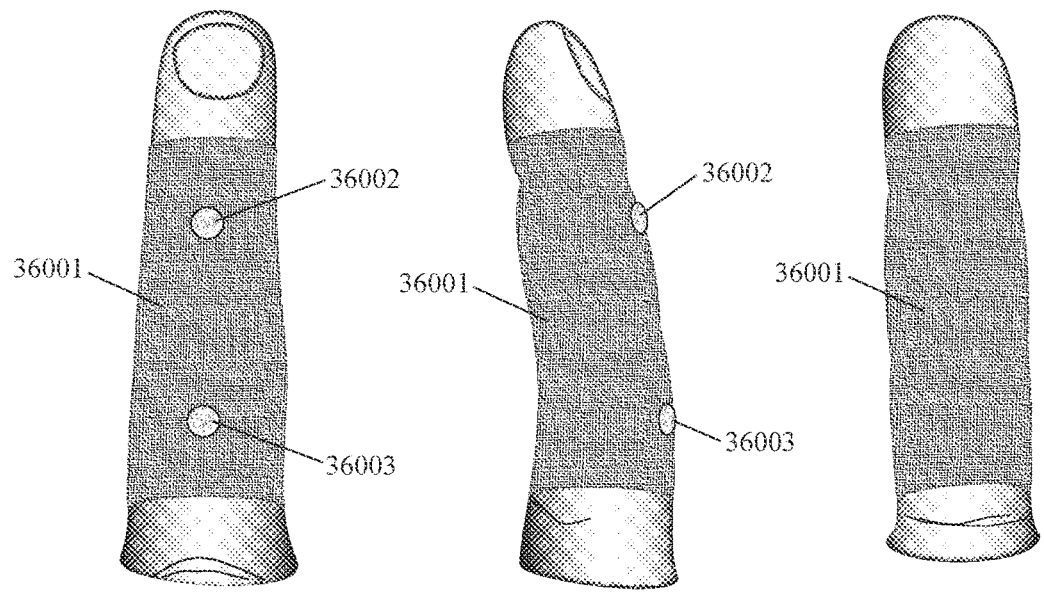
FIG. 36 shows a finger sleeve with light reflectors.

FIG. 36 shows another example of how this invention can be embodied in a wearable device for measuring finger motion and recognizing hand gestures. This example is similar to the one shown in FIG. 35, except that this example has passive light-energy reflectors instead of inertial motion sensors. The left third of FIG. 36 shows this device from a top-down perspective, looking at the upper (dorsal) surface of a person's finger. The middle third of FIG. 36 shows this same device from a side perspective, with the finger having been rotated 90 degrees clockwise. The right third of FIG. 36 shows this same device from a bottom-up perspective, looking at the lower (ventral) surface of the finger.

Specifically, FIG. 36 shows a wearable device for measuring finger motion and recognizing hand gestures comprising: a finger sleeve (36001) which is configured to be worn around a person's finger and to span at least one interphalangeal joint; a first light-energy reflector (36002) which is part or, or attached to, the finger sleeve at a location which is distal to the interphalangeal joint; and a second light-energy reflector (36003) which is part or, or attached to, the finger sleeve at a location which is proximal to the interphalangeal joint.

A finger sleeve herein can be selected and configured as described previously in the narrative which accompanies FIG. 35. A light-energy reflector herein can be selected and configured as described previously in the narrative which accompanies FIG. 3. Other relevant design variations discussed with respect to other examples in this description can also apply to the example shown here in FIG. 36.

Figure 37:
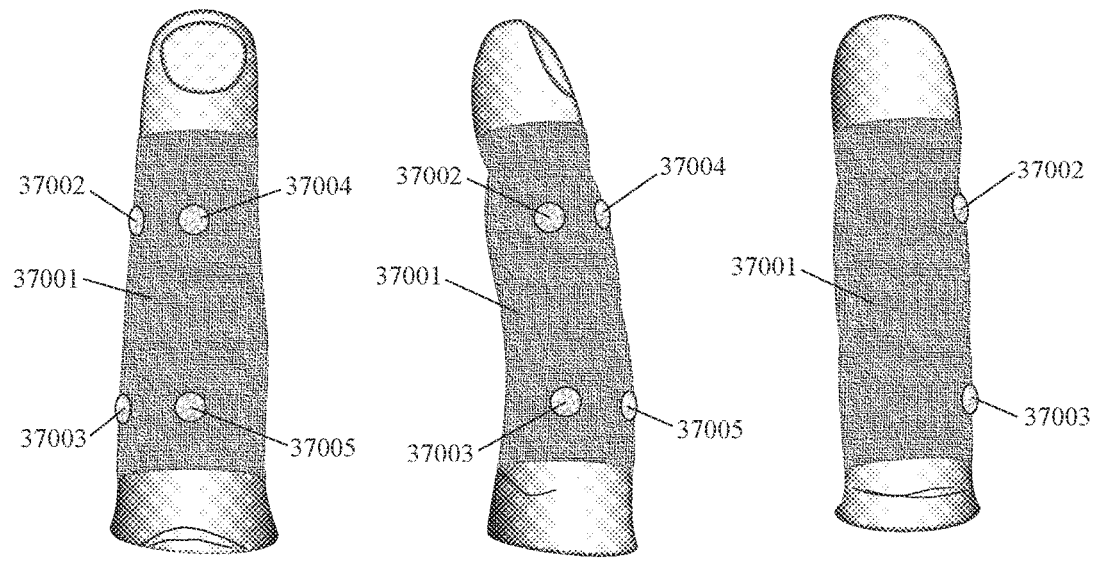
FIG. 37 shows a finger sleeve with dorsal and lateral light reflectors.

FIG. 37 shows another example of how this invention can be embodied in a wearable device for measuring finger motion and recognizing hand gestures. This example is similar to the one shown in FIG. 36, except that this example has passive light-energy reflectors on the lateral side as well as the dorsal side of the finger. The left third of FIG. 37 shows this device from a top-down perspective, looking at the upper (dorsal) surface of a person's finger. The middle third of FIG. 37 shows this same device from a side perspective, with the finger having been rotated 90 degrees clockwise. The right third of FIG. 37 shows this same device from a bottom-up perspective, looking at the lower (ventral) surface of the finger.

Specifically, FIG. 37 shows a wearable device for measuring finger motion and recognizing hand gestures comprising: a finger sleeve (37001) which is configured to be worn around a person's finger and to span at least one interphalangeal joint; a first set of light-energy reflectors (37002 and 37004) which are part or, or attached to, the finger sleeve at a location which is distal to the interphalangeal joint; and a second set of light-energy reflectors (37003 and 37005) which are part or, or attached to, the finger sleeve at a location which is proximal to the interphalangeal joint.

A finger sleeve herein can be selected and configured as described previously in the narrative which accompanies FIG. 35. In this example, at least one reflector in the first set is configured to be located on the lateral side of a finger and at least one reflector in the second set is configured to be located on the lateral side of the finger. In this example, at least one reflector in the first set is configured to be located on the dorsal side of a finger and at least one reflector in the second set is configured to be located on the dorsal side of the finger. In various examples, a light-energy reflector can be configured as described previously in the narrative which accompanies FIG. 3. Other relevant design variations discussed with respect to other examples in this description can also apply to the example shown here in FIG. 37.

Figure 38:
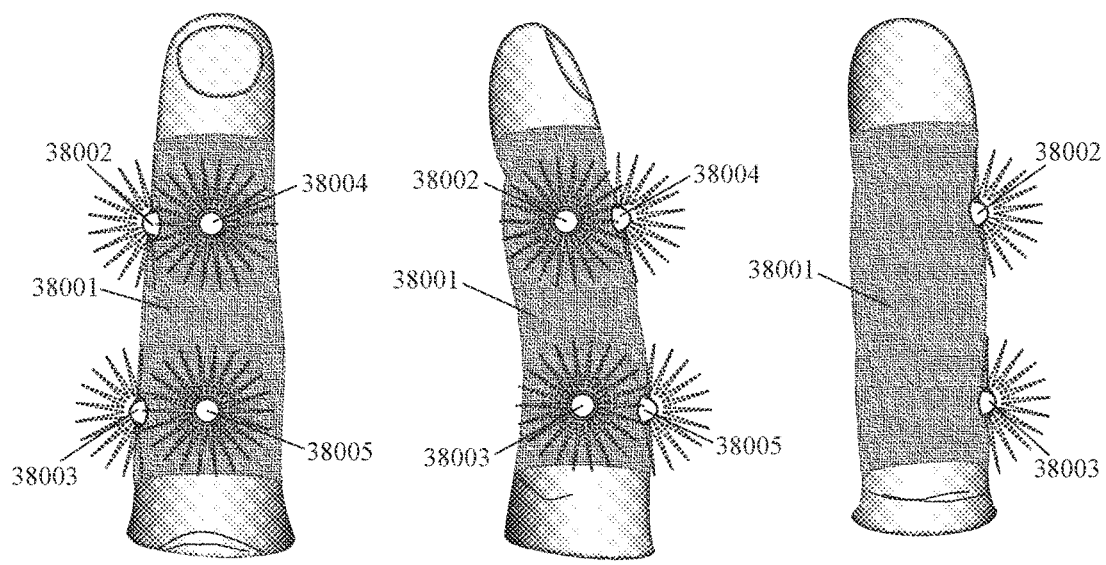
FIG. 38 shows a finger sleeve with dorsal and lateral light emitters.

FIG. 38 shows another example of how this invention can be embodied in a wearable device for measuring finger motion and recognizing hand gestures. This example is similar to the one shown in FIG. 37, except that this example has active light-energy emitters (such as LEDs) instead of passive light-energy reflectors. The left third of FIG. 38 shows this device from a top-down perspective, looking at the upper (dorsal) surface of a person's finger. The middle third of FIG. 38 shows this same device from a side perspective, with the finger having been rotated 90 degrees clockwise. The right third of FIG. 38 shows this same device from a bottom-up perspective, looking at the lower (ventral) surface of the finger.

Specifically, FIG. 38 shows a wearable device for measuring finger motion and recognizing hand gestures comprising: a finger sleeve (38001) which is configured to be worn around a person's finger and to span at least one interphalangeal joint; a first set of light-energy emitters (38002 and 38004) which are part or, or attached to, the finger sleeve at a location which is distal to the interphalangeal joint; and a second set of light-energy emitters (38003 and 38005) which are part or, or attached to, the finger sleeve at a location which is proximal to the interphalangeal joint.

A finger sleeve herein can be selected and configured as described previously in the narrative which accompanies FIG. 35. In this example, at least one light emitter in the first set is configured to be located on the lateral side of a finger and at least one light emitter in the second set is configured to be located on the lateral side of the finger. In this example, at least one light emitter in the first set is configured to be located on the dorsal side of a finger and at least one light emitter in the second set is configured to be located on the dorsal side of the finger. In various examples, a light-energy emitter (such as an LED) can be configured as described previously in the narrative which accompanies FIG. 32. Other relevant design variations discussed with respect to other examples in this description can also apply to the example shown here in FIG. 38.

Figure 39:
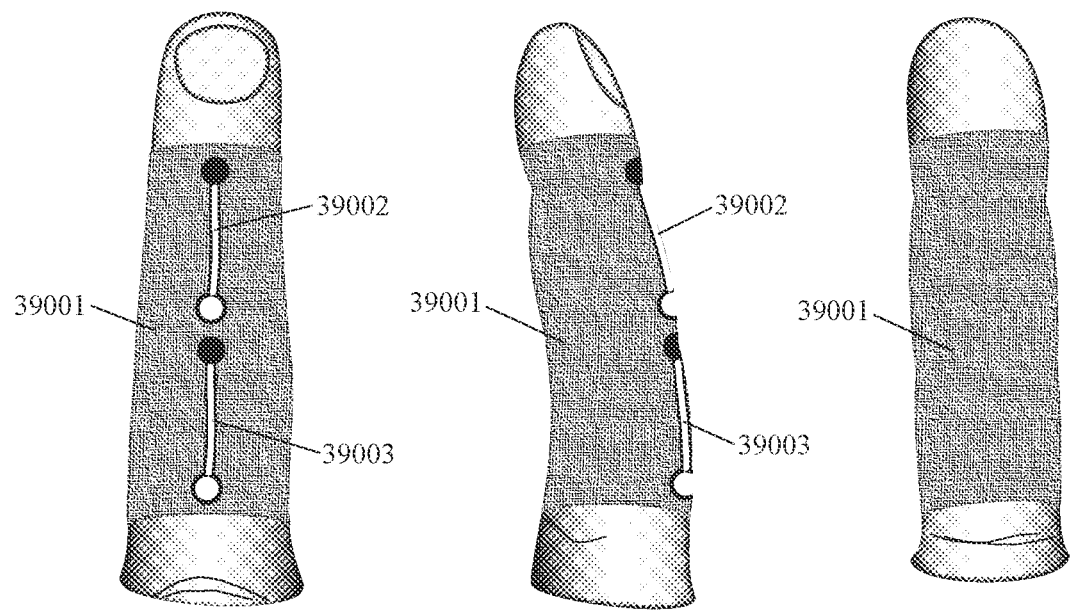
FIG. 39 shows a finger sleeve with bend sensors.

FIG. 39 shows another example of how this invention can be embodied in a wearable device for measuring finger motion and recognizing hand gestures. This example is similar to the one shown in FIG. 35, except that this example has bend sensors instead of inertial motion sensors. The left third of FIG. 39 shows this device from a top-down perspective, looking at the upper (dorsal) surface of a person's finger. The middle third of FIG. 39 shows this same device from a side perspective, with the finger having been rotated 90 degrees clockwise. The right third of FIG. 39 shows this same device from a bottom-up perspective, looking at the lower (ventral) surface of the finger.

Specifically, FIG. 39 shows a wearable device for measuring finger motion and recognizing hand gestures comprising: a finger sleeve (39001) which is configured to be worn around a person's finger and to span at least one interphalangeal joint; a first bend sensor (39002) which is part or, or attached to, the finger sleeve and is configured to span an interphalangeal joint; and a second bend sensor (39003) which is part or, or attached to, the finger sleeve and is configured to span an interphalangeal joint. A finger sleeve can be selected and configured as described previously in the narrative which accompanies FIG. 35.

In an example, a first bend sensor and a second bend sensor can longitudinally span the distal and proximal interphalangeal joints, respectively, of a finger. In an example, a first bend sensor and a second bend sensor can span the dorsal (upper) surface of a finger. In an example, a first bend sensor and a second bend sensor can span the lateral (side) surface of a finger. In an example, a first bend sensor and a second bend sensor can span the ventral (lower) surface of a finger. In an example, first and second bend sensors can span a finger in series, in a distal-to-proximal manner. In an example, a first bend sensor and a second bend sensor can both span the same joint. In an example, having two sensors span the same joint can increase the accuracy of measurement of joint motion. In an example, first and second bend sensors can span a finger in parallel.

In an example, the geometric relationship between a first bend sensor and a second bend sensor can be selected from the group consisting of: in series; sequential; in parallel;

redundant; overlapping; non-overlapping; separated by a substantially-constant distance; separated by a substantially-constant number of radial degrees of the cross-sectional perimeter of a finger; separated by a substantially-constant percentage of the cross-sectional perimeter of a finger; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, the motion and/or configuration of an interphalangeal joint can be measured using multiple bend sensors which span a portion of a finger which contains the interphalangeal joint, wherein these bend sensors span longitudinally-sequential cross-sectional perimeters of the finger along selected radial angles or polar coordinates. In an example, the motion and/or configuration of an interphalangeal joint can be measured using multiple bend sensors which span a portion of a finger which contains the interphalangeal joint, wherein these bend sensors span longitudinally-sequential cross-sectional perimeters of the finger along radial angles or polar coordinates which are evenly distributed around the 0 to 360 degree range. In an example, the motion and/or configuration of an interphalangeal joint can be measured using two bend sensors which span a portion of a finger which contains the interphalangeal joint, wherein these two bend sensors span longitudinally-sequential cross-sectional perimeters of the finger along radial angles or polar coordinates of approximately 0 degrees and 180 degrees. In an example, the 0-degree pathway can span the dorsal surface of a finger and the 180-degree member can span the ventral surface of a finger.

In an example, the motion and/or configuration of an interphalangeal joint can be measured using four bend sensors which span a portion of a finger which contains the interphalangeal joint, wherein these four bend sensors span longitudinally-sequential cross-sectional perimeters of a finger along radial angles or polar coordinates of approximately 0, 90, 180, and 270 degrees. In an example, the 0-degree pathway can span the dorsal surface of a finger, the 180-degree member can span the ventral surface of a finger, and the 90 and 270 degree pathways can span the lateral surfaces of a finger. In an example, a first bend sensor can span the dorsal surface of a finger containing an interphalangeal joint, a second bend sensor can span the ventral surface of that finger, a third bend sensor can span a first lateral surface of that finger, and a fourth bend sensor can span a second lateral surface of that finger.

In an example, the motion and/or configuration of an interphalangeal joint can be measured using multiple bend sensors which span a portion of a finger which contains the interphalangeal joint, wherein these bend sensors span a finger in a substantially parallel manner when the interphalangeal joint is fully extended. In an example, the motion and/or configuration of an interphalangeal joint can be measured using multiple bend sensors which span a portion of a finger which contains the interphalangeal joint, wherein these bend sensors each have central longitudinal axes and wherein these central longitudinal axes are substantially parallel.

In an example, the motion and/or configuration of an interphalangeal joint can be measured using multiple bend sensors which span a portion of a finger which contains the interphalangeal joint, wherein the distances between pairs of bend sensors are substantially constant as they span a finger. In an example, the motion and/or configuration of an interphalangeal joint can be measured using multiple bend sensors which span a portion of a finger which contains the interphalangeal joint, wherein these bend sensors span a finger along substantially-parallel actuate vectors. In an example, the motion and/or configuration of an interphalangeal joint can be measured using multiple bend sensors which span a portion of a finger which contains the interphalangeal joint, wherein these bend sensors span a finger in a nested or concentric manner with substantially constant distances between pairs of nested or concentric bend sensors.

In an example, two bend sensors spanning the same interphalangeal joint can differ in the angles at which they span the longitudinal axis of a finger which contains the interphalangeal joint. In an example, two bend sensors can have longitudinal axes which are substantially perpendicular as they span a finger which contains an interphalangeal joint.

In an example, a first bend sensor and a second bend sensor can each have a circular, semi-circular, or other conic section shape axis. In an example, a circular, semi-circular, or other conic section shape axis can span all or part of the cross-sectional perimeter of a finger containing an interphalangeal joint. In an example, one or more aspects of the geometric relationship between these two axes can be selected from the group consisting of: substantially parallel; separated by a substantially-constant distance; intersecting at an acute angle; forming vectors which intersect in 3D space at an acute angle; combining to form a 3D mesh or grid; differing in length; substantially concentric; nested; differing in diameter; knitted together in loops; and tangential.

In an example, a first bend sensor can have an axis which spans a finger in a longitudinal manner and a second bend sensor can have an axis which spans the same finger in a circular, semi-circular, or other conic sectional manner. In an example, the first bend sensor can span the surface of a finger containing an interphalangeal joint in a distal-to-proximal manner. In an example, the second bend sensor can span the surface of a finger in a circular, semi-circular, or other conic sectional manner. In an example, one or more aspects of the geometric relationship between the first bend sensor and the second bend sensor can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh or grid; overlapping; and tangential.

In an example, a bend sensor can have a substantially straight configuration when a joint is fully extended. In an example, a bend sensor can have an arcuate shape, even when a joint is fully extended. In an example, a bend sensor can have a shape comprising a repeating waveform selected from the group consisting of: simple sinusoidal wave; composite sinusoidal wave; saw-tooth wave or zigzag; and square wave. In an example, a bend sensor can have a shape which is a conic section. In an example, a bend sensor can have a shape which is a spiral or helix. In an example, a bend sensor can have a shape which is a chain of loops.

In an example, first and second bend sensors which span a finger which contains an interphalangeal joint can differ in the angle at which they span a finger. In an example, first and second bend sensors which span a finger which contains an interphalangeal joint can differ in length. In an example, first and second bend sensors which span a finger which contains an interphalangeal joint can differ in longitudinal curvature or convolution. In an example, first and second bend sensors which span a finger which contains an interphalangeal joint can differ in flexibility. In an example, first and second bend sensors which span a finger which contains an interphalangeal joint can differ in elasticity. In an example, first and second bend sensors which span a finger which contains an interphalangeal joint can differ in electrical resistance or impedance. In an example, first and second bend sensors which span a finger which contains an interphalangeal joint can differ in cross-sectional shape.

In an example, a first bend sensor and a second bend sensor which both span the same finger which contains an interphalangeal joint can differ by one or more parameters selected from the group consisting of: the angle at which they span the interphalangeal joint; length; longitudinal curvature or convolution; longitudinal waveform; flexibility; elasticity; electrical resistance or impedance; and cross-sectional shape. In an example, combined multivariate analysis of data from both the first and second bend sensors can provide more accurate measurement of interphalangeal joint motion than analysis of data from either the first bend sensor or the second bend sensor alone. In an example, data from the first bend sensor can provide more accurate measurement of interphalangeal joint motion over a first range of motion and data from the second bend sensor can provide more accurate measurement of interphalangeal joint motion over a second range of motion. When analyzed together, data from the first and second bend sensors reduce error in measuring the full range of joint motion.

In an example, combined, joint, or integrated multivariate analysis of data from multiple bend sensors spanning the same interphalangeal joint can yield measurement of the motion and/or configuration of an interphalangeal joint with a statistically-significant lower error rate or error range than analysis of data from a single bend sensor spanning that interphalangeal joint. In an example, combined, joint, or integrated multivariate analysis of data from multiple bend sensors spanning the same interphalangeal joint can yield measurement of the motion and/or configuration of an interphalangeal joint with a statistically-significant lower error rate or error range than separate analysis of data from those bend sensors. In an example, the statistical significance of error reduction is at the $p<0.05$ level. In an example, statistical significance of error reduction is at the $p<0.01$ level. In an example, estimating the motion and/or configuration of an interphalangeal joint angle using combined, joint, or integrated multivariate analysis of data from multiple bend sensors spanning that joint can yield an over-determined system of equations for joint angle estimation. This can help to reduce measurement error from factors such as: shifting or sliding of the bend sensors and/or the finger sleeve containing the bend sensors over the surface of the finger; and material fatigue and variability in the bend sensors.

In an example, the relationship between energy flow through a bend sensor and the configuration of an interphalangeal joint spanned by that bend sensor can be nonlinear and/or stochastic. In an example, the relationship between energy flow through a bend sensor and the configuration of an interphalangeal joint spanned by that bend sensor can be analyzed using one or more multivariate statistical methods. In an example, data from multiple bend sensors can be jointly analyzed using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

Other relevant design variations for bend sensors which were described previously in the narrative which accompanies FIG. 19 can also be applied to the example shown here in FIG. 39. Other relevant design variations discussed with respect to other examples in this description can also apply to the example shown here in FIG. 39.

Figure 40:
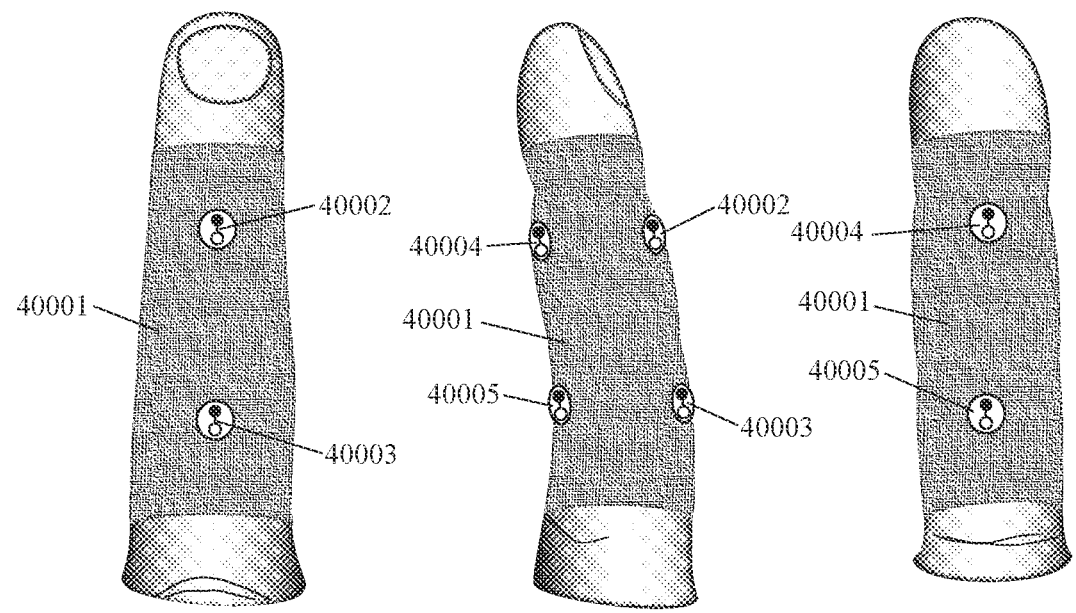
FIG. 40 shows a finger sleeve with EMG sensors.

FIG. 40 shows another example of how this invention can be embodied in a wearable device for measuring finger motion and recognizing hand gestures. This example is similar to the one shown in FIG. 35, except that this example has EMG (electromyographic) sensors instead of inertial motion sensors. The left third of FIG. 40 shows this device from a top-down perspective, looking at the upper (dorsal) surface of a person's finger. The middle third of FIG. 40 shows this same device from a side perspective, with the finger having been rotated 90 degrees clockwise. The right third of FIG. 40 shows this same device from a bottom-up perspective, looking at the lower (ventral) surface of the finger.

Specifically, FIG. 40 shows a wearable device for measuring finger motion and recognizing hand gestures comprising: a finger sleeve (40001) which is configured to be worn around a person's finger and to span at least one interphalangeal joint; a first EMG sensor (40002) which is part or, or attached to, the finger sleeve at a location which is distal to an interphalangeal joint; and a second EMG sensor (40003) which is part or, or attached to, the finger sleeve at a location which is proximal to the interphalangeal joint. A finger sleeve can be selected and configured as described previously in the narrative which accompanies FIG. 35. An EMG sensor can be selected and configured as described previously in the narrative which accompanies FIG. 5. Other relevant design variations discussed with respect to other examples in this description can also apply to the example shown here in FIG. 40.

Figure 41:
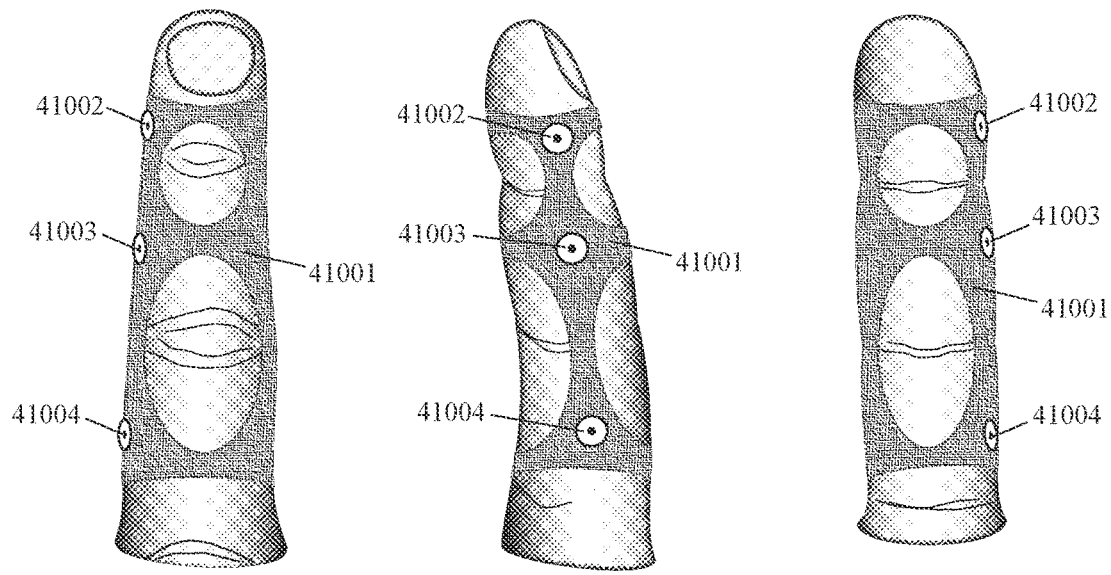
FIG. 41 shows a finger sleeve with holes and inertial motion sensors.

FIG. 41 shows another example of how this invention can be embodied in a wearable device for measuring finger motion and recognizing hand gestures. This example is similar to the one shown in FIG. 35, except that the finger sleeve has arcuate gaps. The left third of FIG. 41 shows this device from a top-down perspective, looking at the upper (dorsal) surface of a person's finger. The middle third of FIG. 41 shows this same device from a side perspective, with the finger having been rotated 90 degrees clockwise.

The right third of FIG. 41 shows this same device from a bottom-up perspective, looking at the lower (ventral) surface of the finger.

Specifically, FIG. 41 shows a wearable device for measuring finger motion and recognizing hand gestures comprising: a finger sleeve (41001) which is configured to be worn on a person's finger, wherein this finger sleeve has at least one arcuate gap (or hole) which spans the surface of a finger containing an interphalangeal joint; and at least two inertial motion sensors (41002, 41003, and 41004) which are part or, or attached to, the finger sleeve.

In an example, an arcuate gap (or hole) in a finger sleeve can be shaped like a circle, oval, ellipse, egg, or quadrilateral with rounded vertexes. In an example, an arcuate gap (or hole) can have a longitudinal axis. In an example, this longitudinal axis can be parallel to the longitudinal axis of a phalanx or interphalangeal joint which the gap (or hole) spans. In an example, an arcuate gap (or hole) can span the dorsal, lateral, and/or ventral surface of a portion of a finger which contains an interphalangeal joint. In an example, a gap (or hole) can be centered on the center of the dorsal, lateral, or ventral surface of a portion of a finger which contains an interphalangeal joint. In an example, an arcuate gap (or hole) can span the dorsal, lateral, and/or ventral surface of a phalanx.

In an example, a finger sleeve can be configured to have one or more arcuate gaps (or holes) selected from the group consisting of: an arcuate gap (or hole) which spans the dorsal surface of a portion of a finger which contains the distal interphalangeal joint; an arcuate gap (or hole) which spans the dorsal surface of a portion of a finger which contains the proximal interphalangeal joint; an arcuate gap (or hole) which spans the ventral surface of a portion of a finger which contains the distal interphalangeal joint; and an arcuate gap (or hole) which spans the ventral surface of a portion of a finger which contains the proximal interphalangeal joint.

In an example, the combination of a finger sleeve and arcuate gaps (or holes) in that sleeve can comprise a cylindrical shape. In an example, this cylindrical shape can have an exterior surface area of X square inches. In an example, arcuate gaps (or holes) in the finger sleeve can have comprise Y square inches of that cylindrical shape. In an example Y can be one-third of X. In an example, Y can be one-half of X. In an example, Y can be two-thirds of X. In an example, Y can be between 20%-80% of X. In an example, gaps (or holes) in a finger sleeve can comprise between 20%-80% of the exterior surface area of a cylinder defined by the finger sleeve.

Other aspects of a finger sleeve can be selected and configured as described previously in the narrative which accompanies FIG. 35. An inertial motion can be selected and configured as described previously in the narrative which accompanies FIG. 1. Other relevant design variations discussed with respect to other examples in this description can also apply to the example shown here in FIG. 41.

Figure 42:
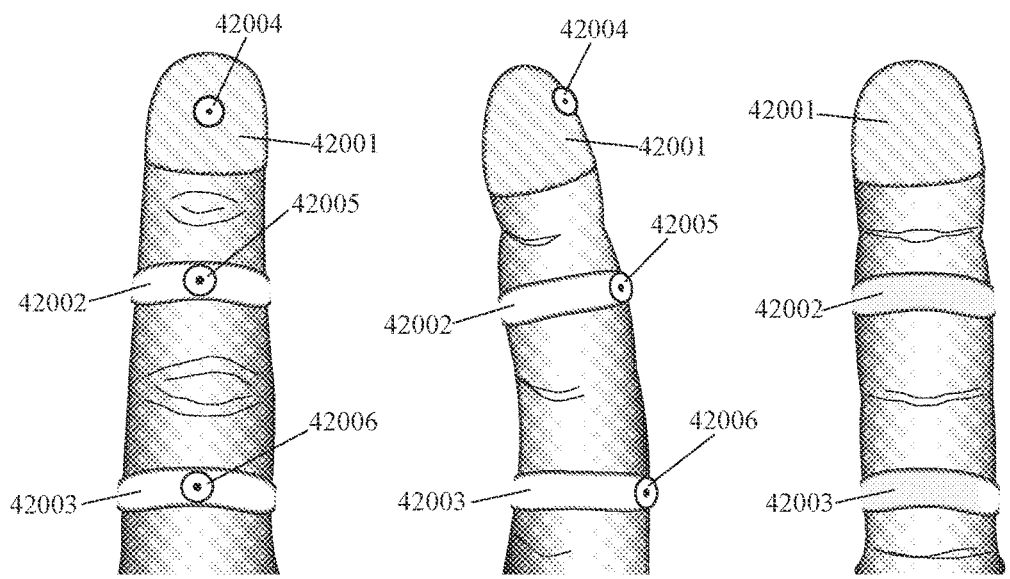
FIG. 42 shows a device with two finger rings, a finger-tip cover or thimble, and inertial motion sensors.

FIG. 42 shows another example of how this invention can be embodied in a wearable device for measuring finger motion and recognizing hand gestures. This example combines the finger rings introduced in FIG. 1 with the finger tip cover introduced in FIG. 16. The left third of FIG. 42 shows this device from a top-down perspective, looking at the upper (dorsal) surface of a person's finger. The middle third of FIG. 42 shows this same device from a side perspective, with the finger having been rotated 90 degrees clockwise. The right third of FIG. 42 shows this same device from a bottom-up perspective, looking at the lower (ventral) surface of the finger.

Specifically, FIG. 42 shows a wearable device for measuring finger motion and recognizing hand gestures comprising: a finger tip cover 42001 which is configured to fit on the tip of a finger; a first finger ring 42002 which is configured to be worn around the intermediate phalanx of the finger; a second finger ring 42003 which is configured to be worn around the proximal phalanx of the finger; a first inertial motion sensor 42004 which is part of, or attached to, the finger tip cover; a second inertial motion sensor 42005 which is part of, or attached to, the first finger ring; and a third inertial motion sensor 42006 which is part of, or attached to, the second finger ring.

A finger tip cover can be selected and configured as described previously in the narrative which accompanies FIG. 16. A finger ring can be selected and configured as described previously in the narrative which accompanies FIG. 1. An inertial motion sensor can be selected and configured as described previously in the narrative which accompanies FIG. 1. Other relevant design variations discussed with respect to other examples in this description can also apply to the example shown here in FIG. 42.

Figure 43:
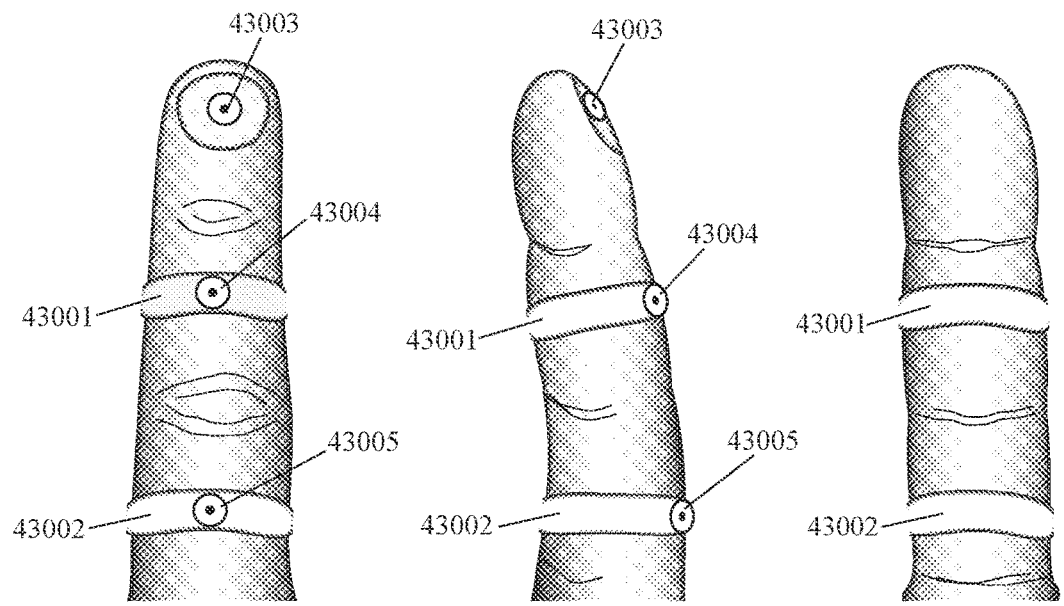
FIG. 43 shows a device with two finger rings and inertial motion sensors, including one attached to a finger nail.

FIG. 43 shows another example of how this invention can be embodied in a wearable device for measuring finger motion and recognizing hand gestures. This example combines the finger rings that were introduced in FIG. 1 with the inertial motion sensor attached to a finger nail that was introduced in FIG. 7. The left third of FIG. 43 shows this device from a top-down perspective, looking at the upper (dorsal) surface of a person's finger. The middle third of FIG. 43 shows this same device from a side perspective, with the finger having been rotated 90 degrees clockwise. The right third of FIG. 43 shows this same device from a bottom-up perspective, looking at the lower (ventral) surface of the finger.

Specifically, FIG. 43 shows a wearable device for measuring finger motion and recognizing hand gestures comprising: a first finger ring 43001 which is configured to be worn around the intermediate phalanx of the finger; a second finger ring 43002 which is configured to be worn around the proximal phalanx of the finger; a first inertial motion sensor 43003 which is attached to the finger nail of the finger; a second inertial motion sensor 43004 which is part of, or attached to, the first finger ring; and a third inertial motion sensor 43005 which is part of, or attached to, the second finger ring.

Finger rings can be selected and configured as described previously in the narrative which accompanies FIG. 1. Inertial motion sensors can be selected, configured, and attached as described previously in the narrative which accompanies FIG. 7. Other relevant design variations discussed with respect to other examples in this description can also apply to the example shown here in FIG. 43.

Figure 44:
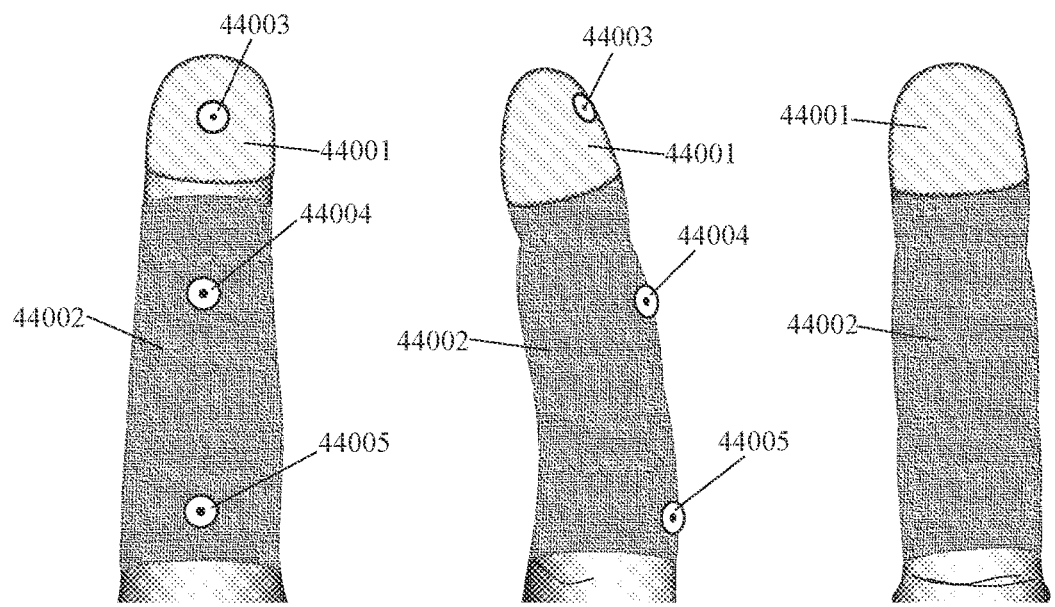
FIG. 44 shows a device with a finger sleeve, a finger-tip cover or thimble, and inertial motion sensors.

FIG. 44 shows another example of how this invention can be embodied in a wearable device for measuring finger motion and recognizing hand gestures. This example combines the finger tip cover that was introduced in FIG. 16 with the finger sleeve that was introduced in FIG. 35. The left third of FIG. 44 shows this device from a top-down perspective, looking at the upper (dorsal) surface of a person's finger. The middle third of FIG. 44 shows this same device from a side perspective, with the finger having been rotated 90 degrees clockwise. The right third of FIG. 44 shows this same device from a bottom-up perspective, looking at the lower (ventral) surface of the finger.

Specifically, FIG. 44 shows a wearable device for measuring finger motion and recognizing hand gestures comprising: a finger tip cover 44001 which is configured to fit on the tip of a finger; a finger sleeve 44002 which is configured to be worn around a person's finger and span at least one interphalangeal joint; a first inertial motion sensor 44003 which is part or, or attached to, the finger tip cover; a second inertial motion sensor 44004 which is part or, or attached to, the finger sleeve at a location which is distal to the interphalangeal joint; a third inertial motion sensor 44005 which is part or, or attached to, the finger sleeve at a location which is proximal to the interphalangeal joint.

A finger tip cover can be selected and configured as described previously in the narrative which accompanies FIG. 16. A finger sleeve can be selected and configured as described previously in the narrative which accompanies FIG. 35. Inertial motion sensors can be selected and configured as described previously in the narrative which accompanies FIG. 1. Other relevant design variations discussed with respect to other examples in this description can also apply to the example shown here in FIG. 44.

Figure 45:
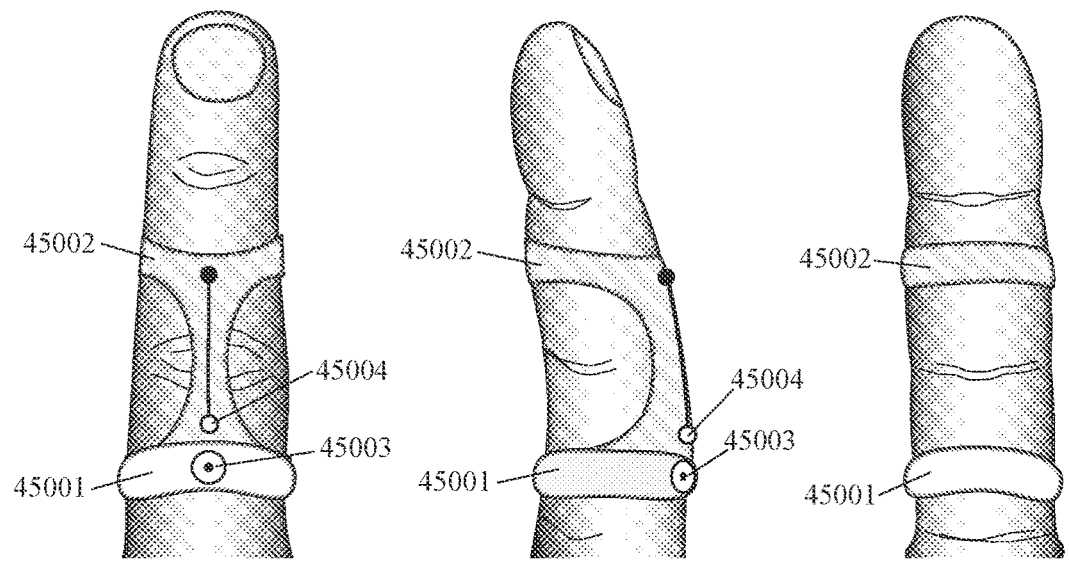
FIG. 45 shows a device with a finger ring, a bi-loop arcuate member, a bend sensor, and an inertial motion sensor.

FIG. 45 shows another example of how this invention can be embodied in a wearable device for measuring finger motion and recognizing hand gestures. This example combines a finger ring like the ones introduced in FIG. 1 with a bi-loop arcuate member like the one introduced in FIG. 19. The left third of FIG. 45 shows this device from a top-down perspective, looking at the upper (dorsal) surface of a person's finger. The middle third of FIG. 45 shows this same device from a side perspective, with the finger having been rotated 90 degrees clockwise. The right third of FIG. 45 shows this same device from a bottom-up perspective, looking at the lower (ventral) surface of the finger.

Specifically, FIG. 45 shows a wearable device for measuring finger motion and recognizing hand gestures comprising: a finger ring 45001 which is configured to be worn around the proximal phalanx of a finger; a bi-loop arcuate member 45002, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the dorsal surface of the proximal interphalangeal joint of the finger, wherein the joint-spanning strip spans from the distal loop to the proximal loop, and wherein the joint-spanning strip bends when the proximal interphalangeal joint bends; an inertial motion sensor 45003 which is part of, or attached to, the finger ring; and a bend sensor 45004, wherein this bend sensor is part of, or attached to the flexible joint-spanning strip, wherein the bend sensor is configured to span at least a portion of the proximal interphalangeal joint, and wherein changes in energy transmitted through and/or generated by the bend sensor are used to measure the motion and/or configuration of the proximal interphalangeal joint.

A finger ring can be selected and configured like one of the finger rings described previously in the narrative which accompanies FIG. 1. A bi-loop arcuate member can be selected and configured as described previously in the narrative which accompanies FIG. 19. An inertial motion sensor can be selected and configured as described previously in the narrative which accompanies FIG. 1. One or more bend sensors can be selected and configured as described previously in the narrative which accompanies FIG. 19. Other relevant design variations discussed with respect to other examples in this description can also apply to the example shown here in FIG. 45.

Figure 46:
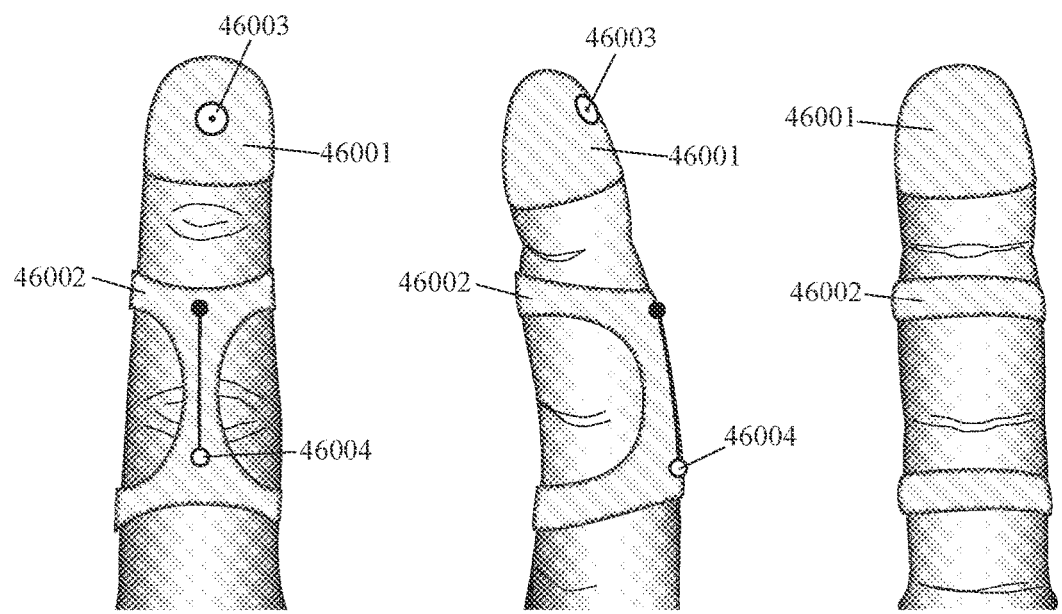
FIG. 46 shows a device with a bi-loop arcuate member, a finger-tip cover or thimble, a bend sensor, and an inertial motion sensor.

FIG. 46 shows another example of how this invention can be embodied in a wearable device for measuring finger motion and recognizing hand gestures. This example combines the finger tip cover that was introduced in FIG. 16 with the bi-loop arcuate member that was introduced in FIG. 19. The left third of FIG. 46 shows this device from a top-down perspective, looking at the upper (dorsal) surface of a person's finger. The middle third of FIG. 46 shows this same device from a side perspective, with the finger having been rotated 90 degrees clockwise. The right third of FIG. 46 shows this same device from a bottom-up perspective, looking at the lower (ventral) surface of the finger.

Specifically, FIG. 46 shows a wearable device for measuring finger motion and recognizing hand gestures comprising: a finger tip cover 46001 which is configured to fit on the tip of a finger; a bi-loop arcuate member 46002, wherein this bi-loop arcuate member further comprises a distal loop which is configured to encircle the intermediate phalanx of the finger, a proximal loop which is configured to encircle the proximal phalanx of the finger, and a flexible joint-spanning strip which is configured to span the dorsal surface of the proximal interphalangeal joint of the finger, wherein the joint-spanning strip spans from the distal loop to the proximal loop, and wherein the joint-spanning strip bends when the proximal interphalangeal joint bends; an inertial motion sensor 46003 which is part or, or attached to, the finger tip cover; and a bend sensor 46004, wherein this bend sensor is part of, or attached to the flexible joint-spanning strip, wherein the bend sensor is configured to span at least a portion of the proximal interphalangeal joint, and wherein changes in energy transmitted through and/or generated by the bend sensor are used to measure the motion and/or configuration of the proximal interphalangeal joint.

A finger tip cover can be selected and configured as described previously in the narrative which accompanies FIG. 16. A bi-loop arcuate member can be selected and configured as described previously in the narrative which accompanies FIG. 19. An inertial motion sensor can be selected and configured as described previously in the narrative which accompanies FIG. 1. One or more bend sensors can be selected and configured as described previously in the narrative which accompanies FIG. 19. Other relevant design variations discussed with respect to other examples in this description can also apply to the example shown here in FIG. 46.

Figure 47:
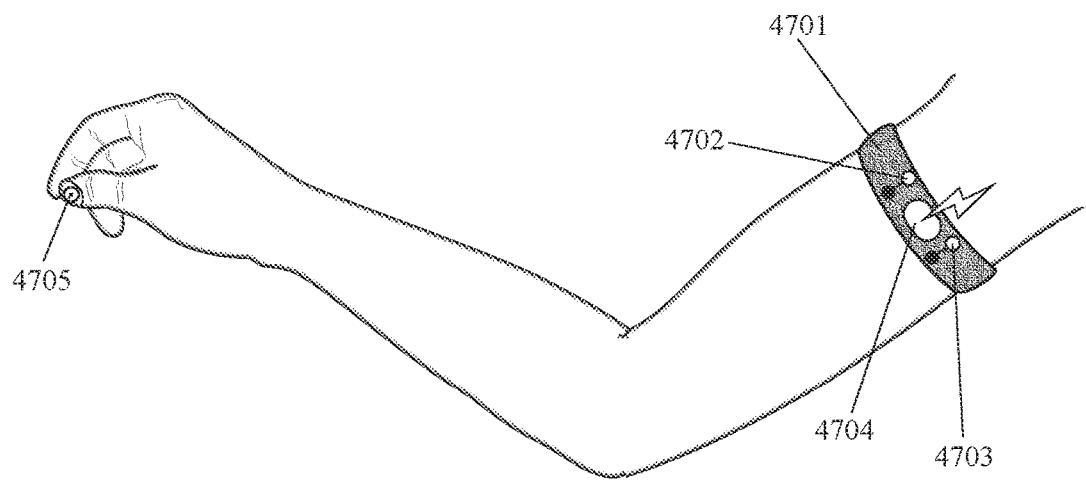
FIGS. 47 and 48 show an armband with EMG sensors and inertial motion sensors attached to finger nails.
Figure 48:
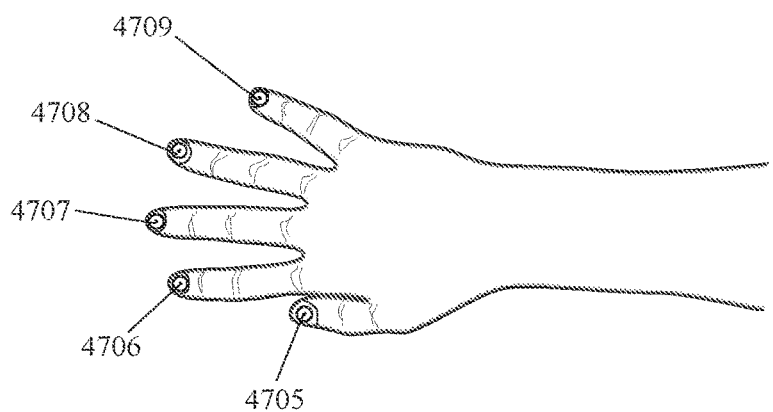

FIGS. 47 and 48 show two views of a wearable system for measuring finger motion and recognizing hand gestures. This system includes: an arm band comprising one or more electromyographic (EMG) sensors; and one or more motion sensors which are configured to be attached to one or more finger nails, respectively. FIG. 47 shows a full-arm side view of this system. FIG. 48 shows a lower-arm top-down view of this system, looking at the upper (dorsal) surface of a hand.

FIGS. 47 and 48 show a wearable system for measuring finger motion and recognizing hand gestures comprising: arm band 4701; one or more electromyographic (EMG) sensors (4702 and 4703); data processor and transmitter 4704; and a one or more motion sensors (4705, 4706, 4707, 4708, and 4708) which are configured to be attached to one or more finger nails, respectively. Data collected by the one or more electromyographic (EMG) sensors and the one or more motion sensors are analyzed together to measure finger motion and recognize hand gestures.

Electromyography (EMG) is a method of measuring changes in electromagnetic energy which are produced by the activity of muscles and/or the nerves which innervate those muscles. These changes in electromagnetic energy are called electromyographic signals ("EMG signals"). Muscles are controlled by motor neurons. Electrical signals transmitted by these motor neurons cause innervated muscles to contract. The electrical signals transmitted by nerves are called action potentials. These action potentials are particularly active during muscle fiber contraction. The electrical potential associated with muscle contraction is generally proportional to the strength of contraction. Accordingly, EMG signals are generally stronger during more-rigorous muscle contraction.

Electromyographic sensors ("EMG sensors") are electromagnetic energy sensors which are placed in proximity to one or more muscles and/or nerves in order to measure the electromagnetic energy created by these muscles and/or nerves during muscle activation. The combination of a motor neuron and the muscle fibers which that neuron innervates is called a motor unit. An EMG sensor at a particular location can measure the accumulated electromagnetic energy from multiple nearby motor units, especially if the EMG sensor is a surface EMG sensor that does not penetrate the person's skin. In an example, an EMG signal can be a composite of action potentials from multiple motor units. Decomposing a composite EMG signal to infer the action potentials (and motions) or individual motor units can be challenging, but can be possible because different motor units can have different electromagnetic signal patterns.

In an example, an EMG sensor can be a bipolar EMG sensor. A bipolar EMG sensor comprises a ground electrode and a sensor electrode. In an example, multiple mono-pole EMGs can share a common ground (or reference) electrode. In an example, two electrodes can be coupled with an amplifier which increases the voltage difference between them. In an example, the output of the amplifier can be sent to an analog-to-digital converter. In an example, changes in electromagnetic energy can be measured by one or more parameters selected from the group consisting of: voltage, resistance, impedance, amperage, current, phase, and wave pattern.

In an example, an EMG sensor can be a surface EMG sensor ("sEMG") which is in direct contact with a person's skin in proximity to the muscles and/or nerves being measured. A surface EMG sensor measures the combined electromagnetic energy which reaches a person's skin from underlying electrical potentials that travel along one or more nearby contracting muscles. As contraction of muscle fibers increases and/or more muscle fibers contract, the resulting electrical potential increases and can be measure from the surface of the person's skin. Contraction of a muscle fiber is followed by relaxation of that fiber. The sequential contraction and relation of a muscle fiber comprises a muscle "twitch." Muscles include fast twitch fibers and slow twitch fibers with different force dynamics.

In an example, an EMG sensor can be a contactless EMG sensor which is close to the person's skin but not in direct contact. In an example, electromagnetic current can be created within an EMG sensor by conduction. In an example, electromagnetic current can be created within an EMG sensor by induction. In an example, electromagnetic current can be created with an EMG sensor by capacitance.

In an example, a motion sensor can be an accelerometer. In an example, a motion sensor can be a combination of an accelerometer and a gyroscope. In an example, a motion sensor can be directly attached to a finger nail. In an example, a motion sensor can be directly attached to a finger nail by adhesion. In an example, a motion sensor can be removably attached to a base member, wherein a base member is directly attached to a finger nail. In an example, a base member can be an artificial finger nail. In an example, a motion sensor can fit into an opening, track, groove, or hole in a base member. In an example, a motion sensor can be attached to a base member by a means selected from the group consisting of: snap, clip, clasp, hook, plug, pin, magnet, and hook-and-eye fabric.

In an example, there can be one motion sensor on the finger nail of each of a person's fingers and thumb. In another example, motion sensors can be worn on only a subset of the finger nails of a person's fingers and thumb. In an example, a first motion sensor can be worn on the finger nail of a person's index finger and a second motion sensor can be worn on the finger nail of person's thumb. In an example, a motion sensor may be worn only on the finger mail of a person's index finger. In an example, a motion sensor may be worn only on the finger nail of a person's ring finger. Other relevant design variations discussed with respect to other examples in this disclosure, or related disclosures incorporated by reference, can also apply to the example shown here.

Figure 49:
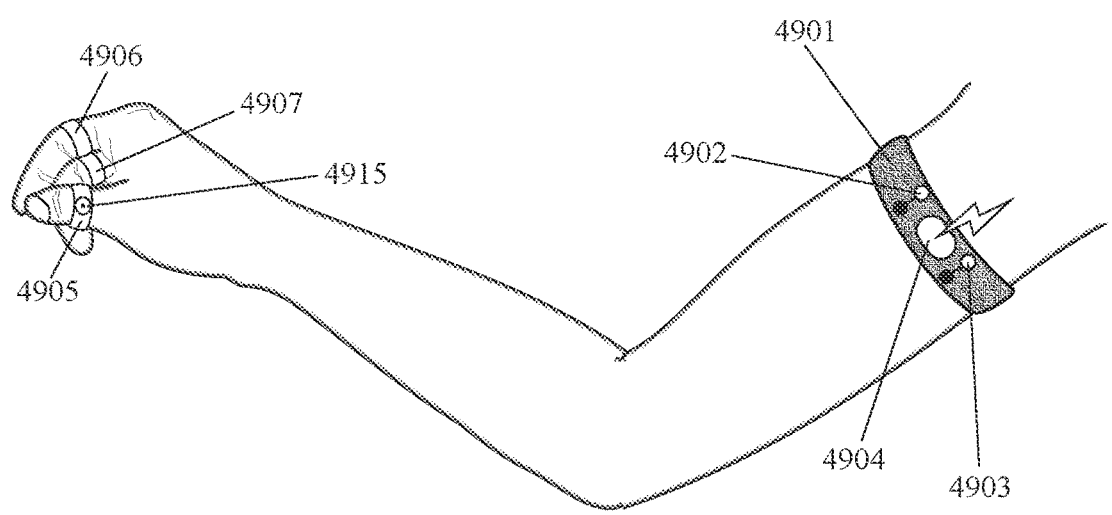
FIGS. 49 and 50 show an armband with EMG sensors and finger rings with inertial motion sensors.
Figure 50:
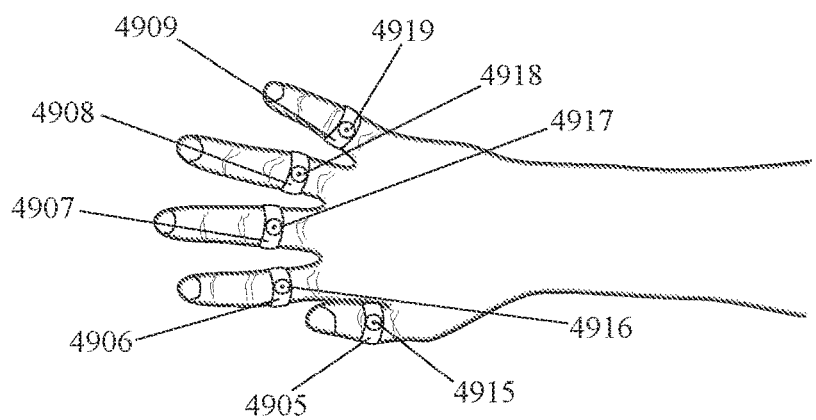

FIGS. 49 and 50 show two views of another wearable system for measuring finger motion and recognizing hand gestures. This system includes: an arm band comprising one or more electromyographic (EMG) sensors; one or more finger rings; and one or more motion sensors which are part of the one or more finger rings, respectively. FIG. 49 shows a full-arm side view of this system. FIG. 50 shows a lower-arm top-down view of this system, looking at the upper (dorsal) surface of a hand.

FIGS. 49 and 50 show a wearable system for measuring finger motion and recognizing hand gestures comprising: arm band 4901; one or more electromyographic (EMG) sensors (4902 and 4903); data processor and transmitter 4904; one or more finger rings (4905, 4906, 4907, 4908, and 4909); and one or more motion sensors (4915, 4916, 4917, 4918, and 4919) which are part of the one or more finger rings, respectively. Data collected by the one or more electromyographic (EMG) sensors and the motion sensors are analyzed together to measure finger motion and recognize hand gestures.

In an example, there can be one finger ring with a motion sensor worn on each of a person's fingers and thumb. In another example, finger rings with motion sensors can be worn on only a subset of the finger nails of a person's fingers and thumb. In an example, a first finger ring with a motion sensor can be worn on a person's index finger and a second finger ring with a motion sensor can be worn on the person's thumb. In an example, a finger ring with a motion sensor may be worn only on a person's index finger. In an example, a finger ring with a motion sensor may be worn only on a person's ring finger.

In an example, one or more finger rings can be worn around the proximal phalanx of a finger, the intermediate phalanx of a finger, and/or the distal phalanx of a finger. In an example, more than one finger ring can be worn on multiple phalanges of the same finger. In an example, first and second finger rings can be worn on the distal phalanx and the intermediate phalanx of a finger, respectively. In an example, there can be three rings, one each on the distal phalanx, the intermediate phalanx, and the proximal phalanx of a finger. Other relevant design variations discussed with respect to other examples in this disclosure, or related disclosures incorporated by reference, can also apply to the example shown here.

Figure 51:
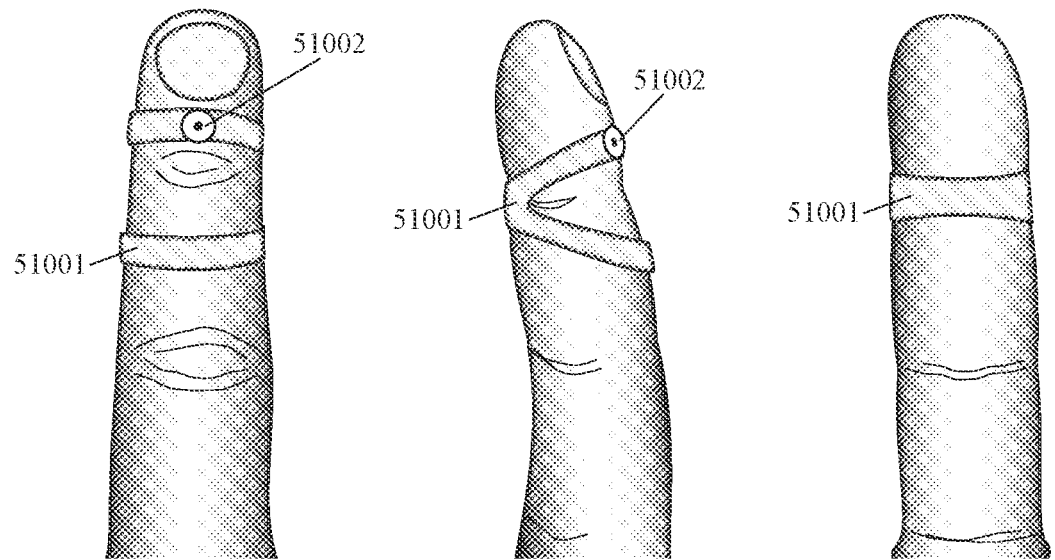
FIG. 51 shows a bifurcating joint-spanning band with a motion sensor.

FIG. 51 shows another example of how this invention can be embodied in a wearable device for measuring finger motion and recognizing hand gestures. The left third of FIG. 51 shows this device from a top-down perspective, looking at the upper (dorsal) surface of a person's finger. The middle third of FIG. 51 shows this same device from a side perspective, with the finger having been rotated 90 degrees clockwise. The right third of FIG. 51 shows this same device from a bottom-up perspective, looking at the lower (ventral) surface of the finger.

The device shown in FIG. 51 includes a bifurcating band which is worn around the distal interphalangeal joint and a motion sensor which is held onto the finger by the bifurcating band. Specifically, FIG. 51 shows a wearable device for measuring finger motion and recognizing hand gestures comprising: bifurcating band 51001 which is configured to be worn around the distal interphalangeal joint of a finger; and motion sensor 51002 which is held onto the finger by the bifurcating band.

In an example, a bifurcating band can be a bifurcating elastic and/or stretchable band made from an elastic and/or stretchable fabric. In an example, a bifurcating band can be made from metal or polymer, but be configured to be expandable and/or stretchable. In an example, a bifurcating band can be sufficiently elastic that it can be slid over the end of a person's finger, but be sufficiently resilient to stay on the finger once so placed. In an example, a bifurcating band can be breathable and/or have a number of holes.

In an example, a bifurcating band can be a single loop (and/or band) as it spans the lower (ventral) surface of a finger, but be two loops (and/or bands) as it spans the upper (dorsal) surface of the finger. In an example, a bifurcating band can converge into a single loop (and/or band) as it spans the lower (ventral) surface of a finger and can diverge into two loops (and/or bands) as it spans the upper (dorsal) surface of the finger. In an example, a bifurcating band can span the center of a distal interphalangeal joint as it spans the lower (ventral) surface of a finger and can span the distal and intermediate phalanges as it spans the upper (dorsal) surface of the finger. In an example, a bifurcating band can have a "V" or "U" shape as viewed from the side. In an example, a bifurcating band can have a double band shape as viewed from the top down.

In an example, a motion sensor can be an accelerometer. In an example, a motion sensor can be a combination of an accelerometer and a gyroscope. In an example, a motion sensor can be held on the upper (dorsal) surface of a finger by the bifurcating band. In an example, a motion sensor can be held on the distal phalanx by the bifurcating band. In an example, a motion sensor can be held on the intermediate phalanx by the bifurcating band. In an example, a motion sensor can be an integral part of a bifurcating band. In an example, a motion sensor can be removably attached to a bifurcating band.

In an example, there can be one of these devices on each of a person's fingers and thumb. In another example, such devices may be worn on only a subset of a person's fingers and thumb. In an example, a first such device can be worn on a person's index finger and a second such device can be worn on a person's thumb. In an example, such a device may be worn only on a person's index finger. In an example, such a device may be worn only on a person's ring finger. Other relevant design variations discussed with respect to other examples in this disclosure, or related disclosures incorporated by reference, can also apply to the example shown here.

Figure 52:
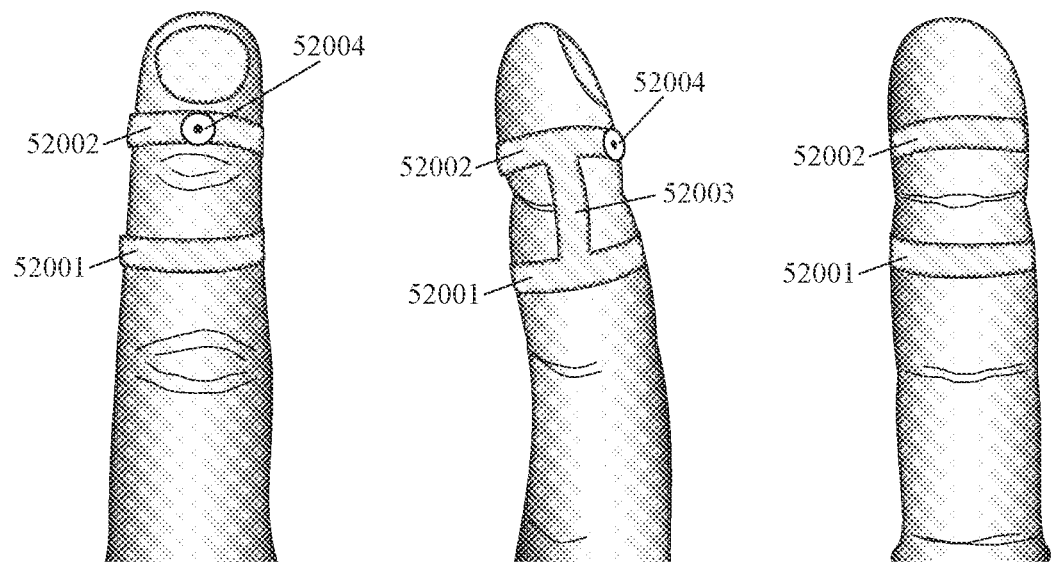
FIG. 52 shows dual connected bands with a motion sensor.

FIG. 52 shows another example of how this invention can be embodied in a wearable device for measuring finger motion and recognizing hand gestures. The left third of FIG. 52 shows this device from a top-down perspective, looking at the upper (dorsal) surface of a person's finger. The middle third of FIG. 52 shows this same device from a side perspective, with the finger having been rotated 90 degrees clockwise. The right third of FIG. 52 shows this same device from a bottom-up perspective, looking at the lower (ventral) surface of the finger.

The device shown in FIG. 52 includes: a first band which is configured to be worn around the distal phalanx; a second band which is configured to be worn around the intermediate phalanx; two longitudinal strips along the right and left sides of the distal interphalangeal joint, respectively, which connect the first and second bands; and a motion sensor which is held onto the distal phalanx by the first band. Specifically, FIG. 52 shows a wearable device for measuring finger motion and recognizing hand gestures comprising: first band 52001 which is configured to be worn around the intermediate phalanx; second band 52002 which is configured to be worn around the distal phalanx; two longitudinal strips (including 52003 shown) along the right and left sides of the distal interphalangeal joint, respectively, which connect the first and second bands; and motion sensor 52004 which is held onto the distal phalanx by the first band.

In an example, a first and/or second band can be an elastic and/or stretchable band made from an elastic and/or stretchable fabric. In an example, a first and/or second band can be made from metal or polymer, but be configured to be expandable and/or stretchable. In an example, a first and/or second band can be sufficiently elastic that it can be slid over the end of a person's finger, but sufficiently resilient to stay on the finger once so placed. In an example, a first and/or second band can be breathable and/or have a number of holes.

In an example, a motion sensor can be an accelerometer. In an example, a motion sensor can be a combination of an accelerometer and a gyroscope. In an example, a motion sensor can be held on the upper (dorsal) surface of the distal phalanx by the second band. In an example, a motion sensor can be an integral part of the second band. In an example, a motion sensor can be removably attached to the second band.

In an example, there can be one of these devices on each of a person's fingers and thumb. In another example, such devices may be worn on only a subset of a person's fingers and thumb. In an example, a first such device can be worn on a person's index finger and a second such device can be worn on a person's thumb. In an example, such a device may be worn only on a person's index finger. In an example, such a device may be worn only on a person's ring finger. Other relevant design variations discussed with respect to other examples in this disclosure, or related disclosures incorporated by reference, can also apply to the example shown here.

Figure 53:
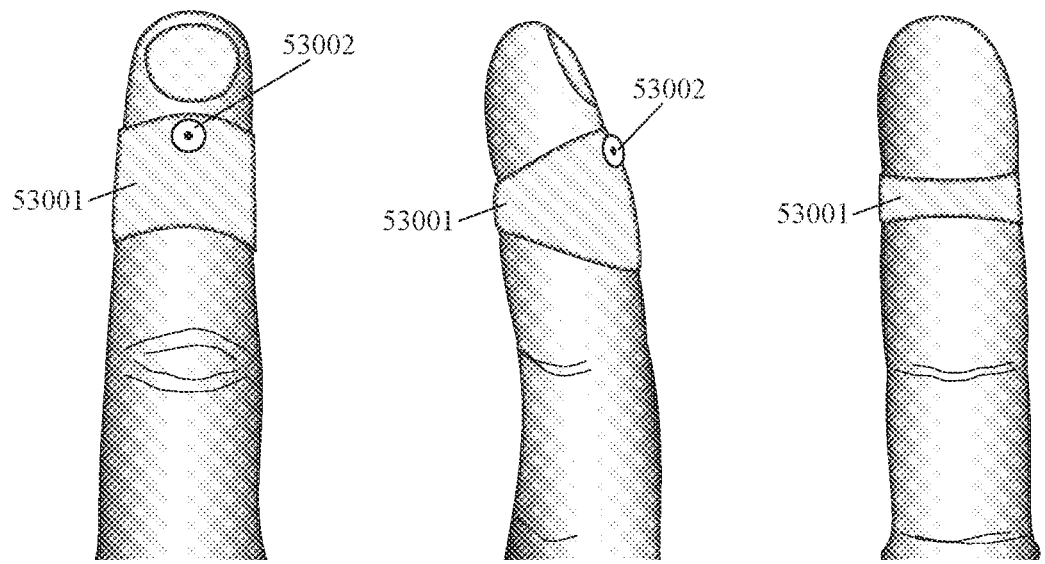
FIG. 53 shows an elastic band with a wider dorsal portion and a motion sensor.

FIG. 53 shows another example of how this invention can be embodied in a wearable device for measuring finger motion and recognizing hand gestures. The left third of FIG. 53 shows this device from a top-down perspective, looking at the upper (dorsal) surface of a person's finger. The middle third of FIG. 53 shows this same device from a side perspective, with the finger having been rotated 90 degrees clockwise. The right third of FIG. 53 shows this same device from a bottom-up perspective, looking at the lower (ventral) surface of the finger.

The device shown in FIG. 53 includes: an elastic and/or stretchable band which is configured to be worn around the distal interphalangeal joint, wherein this band has a first width as it spans the upper (dorsal) surface of the finger, wherein this band has a second width as it spans the lower (ventral) surface of the finger, and wherein the first width is greater than the second width; and a motion sensor which is held onto the distal phalanx by the elastic and/or stretchable band.

Specifically, FIG. 53 shows a wearable device for measuring finger motion and recognizing hand gestures comprising: elastic and/or stretchable band 53001 which is configured to be worn around a distal interphalangeal joint, wherein this band has a first width as it spans the upper (dorsal) surface of a finger, wherein this band has a second width as it spans the lower (ventral) surface of the finger, and wherein the first width is greater than the second width; and motion sensor 54002 which is held onto the distal phalanx by the elastic and/or stretchable band.

In an example, the first width can be at least 50% greater than the second width. In an example, the first width can be at least twice the second width. In an example, an elastic and/or stretchable band can span the center of a distal interphalangeal joint as it spans the lower (ventral) surface of a finger and can span portion of the distal and intermediate phalanges as it spans the upper (dorsal) surface of the finger.

In an example, an elastic and/or stretchable band can be made from an elastic and/or stretchable fabric. In an example, an elastic and/or stretchable band can be made from metal or polymer, but be configured to be expandable and/or stretchable. In an example, an elastic and/or stretchable band can be sufficiently elastic that it can be slid over the end of a person's finger, but be sufficiently resilient to stay on the finger once so placed. In an example, an elastic and/or stretchable band can be breathable and/or have a number of holes.

In an example, a motion sensor can be an accelerometer. In an example, a motion sensor can be a combination of an accelerometer and a gyroscope. In an example, a motion sensor can be held on the upper (dorsal) surface of the distal phalanx by the elastic and/or stretchable band. In an example, a motion sensor can be an integral part of the band. In an example, a motion sensor can be removably attached to the band.

In an example, there can be one of these devices on each of a person's fingers and thumb. In another example, such devices may be worn on only a subset of a person's fingers and thumb. In an example, a first such device can be worn on a person's index finger and a second such device can be worn on a person's thumb. In an example, such a device may be worn only on a person's index finger. In an example, such a device may be worn only on a person's ring finger. Other relevant design variations discussed with respect to other examples in this disclosure, or related disclosures incorporated by reference, can also apply to the example shown here.

FIG. 54 shows another example of how this invention can be embodied in a wearable device for measuring finger motion and recognizing hand gestures. This example is like the one shown in FIG. 53 except that the band has one or more openings or holes. The left third of FIG. 54 shows this device from a top-down perspective, looking at the upper (dorsal) surface of a person's finger. The middle third of FIG. 54 shows this same device from a side perspective, with the finger having been rotated 90 degrees clockwise. The right third of FIG. 54 shows this same device from a bottom-up perspective, looking at the lower (ventral) surface of the finger.

The device shown in FIG. 54 includes: an elastic and/or stretchable band which is configured to be worn around the distal interphalangeal joint, wherein this band has a first width as it spans the upper (dorsal) surface of the finger, wherein this band has a second width as it spans the lower (ventral) surface of the finger, wherein the first width is greater than the second width, and wherein the elastic and/or stretchable band further comprises one or more holes or openings; and a motion sensor which is held onto the distal phalanx by the elastic and/or stretchable band.

Specifically, FIG. 54 shows a wearable device for measuring finger motion and recognizing hand gestures comprising: elastic and/or stretchable band 54001 which is configured to be worn around the distal interphalangeal joint, wherein this band has a first width as it spans the upper (dorsal) surface of the finger, wherein this band has a second width as it spans the lower (ventral) surface of the finger, wherein the first width is greater than the second width, and wherein the elastic and/or stretchable band further comprises one or more holes or openings; and motion sensor 54002 which is held onto the distal phalanx by the elastic and/or stretchable band. Other relevant design variations discussed with respect to other examples in this disclosure, or related disclosures incorporated by reference, can also apply to the example shown here.

In an example, this invention can be embodied in a wearable device for measuring finger motion comprising: a bi-loop arcuate member which further comprises: a distal loop which is configured to encircle the intermediate phalanx of a finger; a proximal loop which is configured to encircle the proximal phalanx of the finger; and a joint-spanning strip which is configured to span the proximal interphalangeal joint of the finger, wherein the joint-spanning strip spans from the distal loop to the proximal loop, and wherein the joint-spanning strip bends when the proximal interphalangeal joint bends; and a bend sensor which is part of, or attached to, the joint-spanning strip, wherein the bend sensor is configured to span at least a portion of the proximal interphalangeal joint, and wherein changes in energy transmitted through, or generated by, the bend sensor are used to measure the motion and/or configuration of the proximal interphalangeal joint.

In an example, a joint-spanning strip can span the dorsal surface of the proximal interphalangeal joint. In an example, distal and proximal loops can encircle the intermediate phalanx and the proximal phalanx, respectively, around the longitudinal middles of these phalanges. In an example, distal and proximal loops can be rings. In an example, changes in electrical energy generated by movement of the bend sensor can be analyzed to model the motion and/or configuration of the proximal interphalangeal joint. In an example, changes in the flow of electrical energy through the bend sensor are analyzed to model the motion and/or configuration of the proximal interphalangeal joint. In an example, changes in the flow of light energy through the bend sensor can be analyzed to model the motion and/or configuration of the proximal interphalangeal joint.

In an example, this invention can be embodied in a wearable device for measuring finger motion comprising: a bi-loop arcuate member which further comprises: a distal loop which is configured to encircle the intermediate phalanx of a finger; a proximal loop which is configured to encircle the proximal phalanx of the finger; and a joint-spanning strip which is configured to span the proximal interphalangeal joint of the finger, wherein the joint-spanning strip spans from the distal loop to the proximal loop, and wherein the joint-spanning strip bends when the proximal interphalangeal joint bends; a bend sensor which is part of, or attached to, the joint-spanning strip, wherein the bend sensor is configured to span at least a portion of the proximal interphalangeal joint, and wherein changes in energy transmitted through, or generated by, the bend sensor are used to measure the motion and/or configuration of the proximal interphalangeal joint; and an inertial motion sensor.

In an example, a inertial motion sensor can be part of, or attached to, the bi-loop arcuate member. In an example, a inertial motion sensor can be configured to be removably attached to a finger nail. In an example, a joint-spanning strip can be configured to span the dorsal surface of the proximal interphalangeal joint. In an example, changes in electrical energy generated by movement of the bend sensor and also movement of the inertial motion sensor can be jointly analyzed to model the motion and/or configuration of the proximal interphalangeal joint. In an example, changes in the flow of electrical energy through the bend sensor and also movement of the inertial motion sensor can be jointly analyzed to model the motion and/or configuration of the proximal interphalangeal joint.

In an example, this invention can be embodied in a wearable device for measuring finger motion comprising an inertial motion sensor which is configured to be removably attached to a finger nail. In an example, a inertial motion sensor can be directly attached to a finger nail by adhesion. In an example, this device further comprises a base member can be attached to the finger nail and to which the inertial motion sensor is removably attached. In an example, a base member can comprise a groove, opening, and/or hole into which the inertial motion sensor is removably inserted. In an example, a base member can comprise a snap, clip, and/or clasp which is used to removably attach the inertial motion sensor. In an example, a base member can comprise a hook, pin, button, plug, and/or magnet which is used to removably attach the inertial motion sensor. In an example, this device can further comprise a first base member which is configured to be attached to a finger nail and a second base member which is configured to be attached to the finger nail, wherein the inertial motion sensor is removably inserted between the first base member and the second base member.

I claim:

1. A wearable device for measuring finger motion comprising:
   a bi-loop arcuate member further comprises: a distal loop configured to encircle an intermediate phalanx of a finger; a proximal loop configured to encircle a proximal phalanx of the finger; and a joint-spanning strip configured to span a proximal interphalangeal joint of the finger,
   wherein the joint-spanning strip spans from the distal loop to the proximal loop, and wherein the joint-spanning strip bends when the proximal interphalangeal joint bends; wherein the joint-spanning strip is configured to span a dorsal surface of the proximal interphalangeal joint, wherein the distal and proximal loops are less elastic and/or stretchable than the joint-spanning strip, and wherein the distal and proximal loops are configured to encircle the intermediate phalanx and the proximal phalanx of the finger around the longitudinal middle of the phalanges of the finger; and
   a bend sensor attached to the joint-spanning strip, wherein the bend sensor is configured to span the proximal interphalangeal joint of the finger,
   wherein the bend sensor is an electromagnetic energy band sensor, wherein the bend sensor configured to detect bending as the finger moves, and wherein the detected bending changes flow of electromagnetic energy, and wherein the changes of the flow of the electromagnetic energy are used to measure the motion and configuration of the proximal interphalangeal joint of the finger.

2. The device in claim 1, wherein the distal and proximal loops are rings.

3. A wearable device for measuring finger motion comprising:
   a bi-loop arcuate member further comprises: a distal loop configured to encircle an intermediate phalanx of a finger; a proximal loop configured to encircle a proximal phalanx of the finger; and a joint-spanning strip configured to span a proximal interphalangeal joint of the finger, wherein the joint-spanning strip spans from the distal loop to the proximal loop, wherein the joint-spanning strip bends when the proximal interphalangeal joint bends, wherein the joint-spanning strip is configured to span a dorsal surface of the proximal interphalangeal joint, wherein the distal and proximal loops are less elastic and/or stretchable than the joint-spanning strip, and wherein the distal and proximal loops are configured to encircle the intermediate phalanx and the proximal phalanx of the finger around the longitudinal middle of the phalanges of the finger; and
   a bend sensor attached to the joint-spanning strip, wherein the bend sensor is configured to span at least a portion of the proximal interphalangeal joint,
   wherein the bend sensor is an electromagnetic energy band sensor, wherein the bend sensor configured to detect bending as the finger moves, and wherein the detected bending changes flow of electromagnetic energy, and wherein the changes of the flow of the electromagnetic energy are used to measure the motion and configuration of the proximal interphalangeal joint of the finger; and an inertial motion sensor.

4. The device in claim 3, wherein the inertial motion sensor is part of, or attached to, the bi-loop arcuate member.

5. The device in claim 3, wherein the inertial motion sensor is configured to be removably attached to a finger nail.

6. The device in claim 3, wherein the changes in electromagnetic energy generated by movement of the bend sensor and movement of the inertial motion sensor are jointly analyzed to model the motion and configuration of the proximal interphalangeal joint.

7. The device in claim 3, wherein the changes in the flow of electromagnetic energy through the bend sensor and movement of the inertial motion sensor are jointly analyzed to model the motion and configuration of the proximal interphalangeal joint.

8. A wearable device for measuring finger motion comprising: a bi-loop arcuate member further comprises: a distal loop configured to encircle an intermediate phalanx of a finger; a proximal loop configured to encircle a proximal phalanx of the finger; and a joint-spanning strip configured to span a proximal interphalangeal joint of the finger, wherein the joint-spanning strip spans from the distal loop to the proximal loop, and wherein the joint-spanning strip bends when the proximal interphalangeal joint bends; wherein the joint-spanning strip is configured to span a dorsal surface of the proximal interphalangeal joint, wherein the distal and proximal loops are less elastic and/or stretchable than the joint-spanning strip, and wherein the distal and proximal loops are configured to encircle the intermediate phalanx and the proximal phalanx of the finger around the longitudinal middle of the phalanges of the finger; and a bend sensor attached to the joint-spanning strip, wherein the bend sensor is configured to span the proximal interphalangeal joint of the finger, wherein the bend sensor is an electromagnetic energy band sensor, wherein the bend sensor configured to detect bending as the finger moves, and wherein the detected bending changes flow of electromagnetic energy, and wherein the changes of the flow of the electromagnetic energy are used to measure the motion and configuration of the proximal interphalangeal joint of the finger; and an inertial motion sensor configured to be removably attached to a finger nail.

9. The device in claim 8, wherein the inertial motion sensor is directly attached to a finger nail by adhesion.

10. The device in claim 8, wherein the device further comprises a base member configured to be attached to the finger nail and to the inertial motion sensor is removably attached.

11. The device in claim 10, wherein the base member comprises a groove, opening, and/or hole, wherein the inertial motion sensor is removably inserted into the base member through at least one of the groove, opening, and hole.

12. The device in claim 10, wherein the base member comprises a snap, clip, and/or clasp, wherein at least one of the snap, clip and clasp is used to removably attach the inertial motion sensor to the base member.

13. The device in claim 10, wherein the base member comprises a hook, pin, button, plug, and/or magnet, wherein at least one of the hook, pin, button, plug and magnet is used to removably attach the inertial motion sensor to the base member.

14. The device in claim 8, wherein the device further comprises a first base member configured to be attached to a finger nail and a second base member configured to be attached to the finger nail, wherein the inertial motion sensor is removably inserted between the first base member and the second base member.

* * * * *